(12) United States Patent
Balakin et al.

(10) Patent No.: US 10,213,626 B2
(45) Date of Patent: Feb. 26, 2019

(54) TREATMENT DELIVERY CONTROL SYSTEM AND METHOD OF OPERATION THEREOF

(71) Applicants: Vladimir Balakin, Protvino (RU); Stephen L. Spotts, Argyle, TX (US)

(72) Inventors: Vladimir Balakin, Protvino (RU); Stephen L. Spotts, Argyle, TX (US)

( * ) Notice: Subject to any disclaimer, the term of this patent is extended or adjusted under 35 U.S.C. 154(b) by 0 days.

(21) Appl. No.: 15/152,479

(22) Filed: May 11, 2016

(65) Prior Publication Data

US 2016/0250503 A1 Sep. 1, 2016

Related U.S. Application Data

(63) Continuation-in-part of application No. 14/216,788, filed on Mar. 17, 2014, which is a continuation-in-part of application No. 13/087,096, filed on Apr. 14, 2011, now Pat. No. 9,044,600, said application No. 14/216,788 is a continuation-in-part of application No. 13/788,890, filed on Mar. 7, 2013, now Pat. No. 8,907,309, application No. 15/152,479, filed on May 11, 2016, which is a continuation-in-part of application No. 14/952,817, filed on Nov. 25,
(Continued)

(51) Int. Cl.
| | |
|---|---|
| *A61N 5/10* | (2006.01) |
| *A61B 6/03* | (2006.01) |
| *G21K 1/093* | (2006.01) |
| *G21K 5/04* | (2006.01) |
| *G21K 1/087* | (2006.01) |
| *H01J 35/14* | (2006.01) |

(52) U.S. Cl.
CPC ............. *A61N 5/1077* (2013.01); *A61B 6/03* (2013.01); *A61N 5/1044* (2013.01); *A61N 5/1067* (2013.01); *A61N 5/1082* (2013.01); *G21K 1/087* (2013.01); *G21K 1/093* (2013.01); *G21K 5/04* (2013.01); *A61N 5/107* (2013.01); *A61N 2005/1074* (2013.01); *A61N 2005/1087* (2013.01); *A61N 2005/1097* (2013.01); *H01J 35/14* (2013.01)

(58) Field of Classification Search
USPC ........................................................ 250/492.3
See application file for complete search history.

(56) References Cited

U.S. PATENT DOCUMENTS

2004/0162457 A1* 8/2004 Maggiore ................ A61N 5/10
600/1

* cited by examiner

*Primary Examiner* — Kiet T Nguyen
(74) *Attorney, Agent, or Firm* — Kevin Hazen

(57) ABSTRACT

The invention relates to a method and apparatus for control of a charged particle cancer therapy system. A treatment delivery control system is used to directly control multiple subsystems of the cancer therapy system without direct communication between selected subsystems, which enhances safety, simplifies quality assurance and quality control, and facilitates programming. For example, the treatment delivery control system directly controls one or more of: an imaging system, a positioning system, an injection system, a radio-frequency quadrupole system, a ring accelerator or synchrotron, an extraction system, a beam line, an irradiation nozzle, a gantry, a display system, a targeting system, and a verification system. Generally, the control system integrates subsystems and/or integrates output of one or more of the above described cancer therapy system elements with inputs of one or more of the above described cancer therapy system elements.

10 Claims, 45 Drawing Sheets

Related U.S. Application Data

2015, which is a continuation-in-part of application No. 14/293,861, filed on Jun. 2, 2014, now Pat. No. 9,498,649, which is a continuation-in-part of application No. 12/985,039, filed on Jan. 5, 2011, now Pat. No. 8,598,543, application No. 15/152,479, filed on May 11, 2016, which is a continuation-in-part of application No. 14/860,577, filed on Sep. 21, 2015, now Pat. No. 9,543,106, which is a continuation of application No. 14/223,289, filed on Mar. 24, 2014, now Pat. No. 9,177,751, which is a continuation-in-part of application No. 14/216,788, filed on Mar. 17, 2014, which is a continuation-in-part of application No. 12/985,039, filed on Jan. 5, 2011, now Pat. No. 8,598,543, application No. 15/152,479, filed on May 11, 2016, which is a continuation-in-part of application No. 15/073,471, filed on Mar. 17, 2016.

(60) Provisional application No. 61/324,776, filed on Apr. 16, 2010, provisional application No. 62/304,839, filed on Mar. 7, 2016.

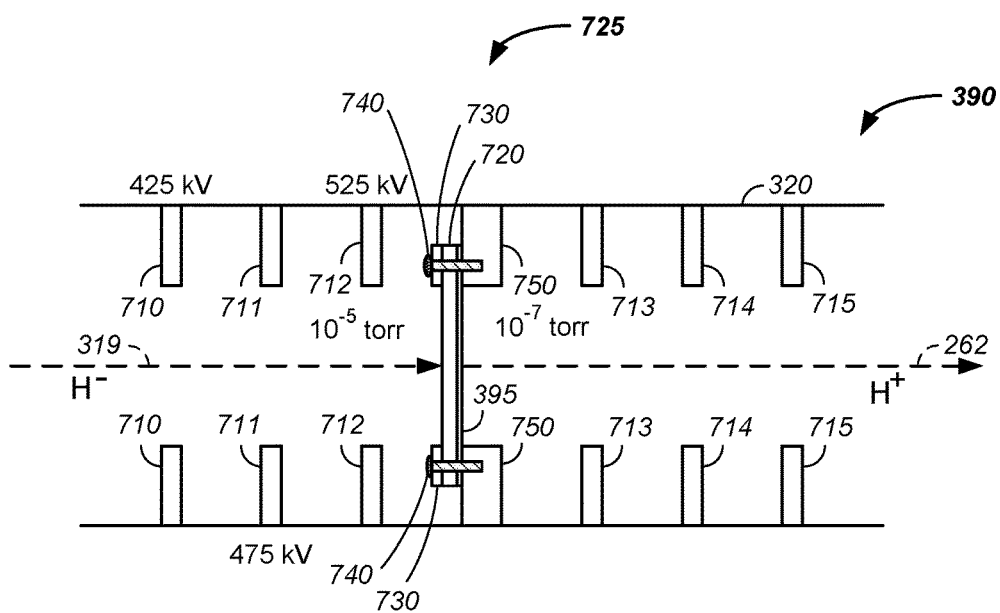
FIG. 7A
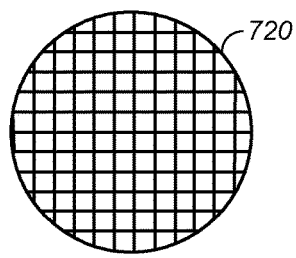 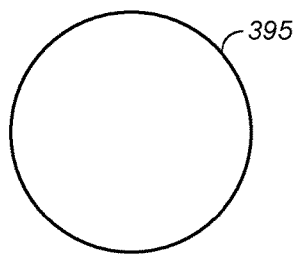
FIG. 7B  FIG. 7C

TREATMENT DELIVERY CONTROL SYSTEM AND METHOD OF OPERATION THEREOF

CROSS-REFERENCES TO RELATED APPLICATIONS

This application:
is a continuation-in-part of U.S. patent application Ser. No. 14/216,788 filed Mar. 17, 2014,
  which is a continuation-in-part of U.S. patent application Ser. No. 13/087,096 filed Apr. 14, 2011, which claims benefit of U.S. provisional patent application No. 61/324,776 filed Apr. 16, 2010; and
  is a continuation-in-part of U.S. patent application Ser. No. 13/788,890 filed Mar. 7, 2013;
is a continuation-in-part of U.S. patent application Ser. No. 14/952,817 filed Nov. 25, 2015 is a continuation-in-part of U.S. patent application Ser. No. 14/293,861 filed Jun. 2, 2014, which is a continuation-in-part of U.S. patent application Ser. No. 12/985,039 filed Jan. 5, 2011, which claims the benefit of U.S. provisional patent application No. 61/324,776, filed Apr. 16, 2010;
is a continuation-in-part of U.S. patent application Ser. No. 14/860,577 filed Sep. 21, 2015, which is a continuation of U.S. patent application Ser. No. 14/223,289 filed Mar. 24, 2014, which is a continuation-in-part of U.S. patent application Ser. No. 14/216,788 filed Mar. 17, 2014, which is a continuation-in-part of U.S. patent application Ser. No. 12/985,039 filed Jan. 5, 2011, which claims the benefit of U.S. provisional patent application No. 61/324,776, filed Apr. 16, 2010; and
is a continuation-in-part U.S. patent application Ser. No. 15/073,471 filed Mar. 17, 2016, which claims benefit of U.S. provisional patent application No. 62/304,839 filed Mar. 7, 2016,
all of which are incorporated herein in their entirety by this reference thereto.

BACKGROUND OF THE INVENTION

Field of the Invention

This invention relates generally to treatment of solid cancers. More particularly, the invention relates to a treatment delivery control system for controlling subsystems of a multi-axis and/or multi-field charged particle cancer therapy method and apparatus.

Discussion of the Prior Art

Cancer Treatment

Proton therapy works by aiming energetic ionizing particles, such as protons accelerated with a particle accelerator, onto a target tumor. These particles damage the DNA of cells, ultimately causing their death. Cancerous cells, because of their high rate of division and their reduced ability to repair damaged DNA, are particularly vulnerable to attack on their DNA.

Synchrotron

Patents related to the current invention are summarized here.

Proton Beam Therapy System

F. Cole, et. al. of Loma Linda University Medical Center "Multi-Station Proton Beam Therapy System", U.S. Pat. No. 4,870,287 (Sep. 26, 1989) describe a proton beam therapy system for selectively generating and transporting proton beams from a single proton source and accelerator to a selected treatment room of a plurality of patient treatment rooms.

Imaging

P. Adamee, et. al. "Charged Particle Beam Apparatus and Method for Operating the Same", U.S. Pat. No. 7,274,018 (Sep. 25, 2007) and P. Adamee, et. al. "Charged Particle Beam Apparatus and Method for Operating the Same", U.S. Pat. No. 7,045,781 (May 16, 2006) describe a charged particle beam apparatus configured for serial and/or parallel imaging of an object.

K. Hiramoto, et. al. "Ion Beam Therapy System and its Couch Positioning System", U.S. Pat. No. 7,193,227 (Mar. 20, 2007) describe an ion beam therapy system having an X-ray imaging system moving in conjunction with a rotating gantry.

C. Maurer, et. al. "Apparatus and Method for Registration of Images to Physical Space Using a Weighted Combination of Points and Surfaces", U.S. Pat. No. 6,560,354 (May 6, 2003) described a process of X-ray computed tomography registered to physical measurements taken on the patient's body, where different body parts are given different weights. Weights are used in an iterative registration process to determine a rigid body transformation process, where the transformation function is used to assist surgical or stereotactic procedures.

M. Blair, et. al. "Proton Beam Digital Imaging System", U.S. Pat. No. 5,825,845 (Oct. 20, 1998) describe a proton beam digital imaging system having an X-ray source that is movable into a treatment beam line that can produce an X-ray beam through a region of the body. By comparison of the relative positions of the center of the beam in the patient orientation image and the isocentre in the master prescription image with respect to selected monuments, the amount and direction of movement of the patient to make the best beam center correspond to the target isocentre is determined.

S. Nishihara, et. al. "Therapeutic Apparatus", U.S. Pat. No. 5,039,867 (Aug. 13, 1991) describe a method and apparatus for positioning a therapeutic beam in which a first distance is determined on the basis of a first image, a second distance is determined on the basis of a second image, and the patient is moved to a therapy beam irradiation position on the basis of the first and second distances.

Problem

There exists in the art of charged particle irradiation therapy a need to accurately and precisely deliver an effective and uniform radiation dose to all positions of a tumor. There further exists a need for accurately, precisely, and timely locating and targeting a tumor in a patient. There still further exists a need in the art to control the charged particle cancer therapy system in terms of patient translation position, patient rotation position, specified energy, specified intensity, timing of charged particle delivery, and/or distribution of radiation striking healthy tissue. There yet still further exists a need for an integrated control system to control and/or to directly control subsystems of a cancer treatment process for enhanced efficacy and safety. Preferably, the system would operate in conjunction with a negative ion beam source, synchrotron, patient positioning, imaging, and/or targeting method and apparatus.

SUMMARY OF THE INVENTION

The invention comprises a charged particle treatment delivery control system.

DESCRIPTION OF THE FIGURES

A more complete understanding of the present invention is derived by referring to the detailed description and claims when considered in connection with the Figures, wherein like reference numbers refer to similar items throughout the Figures.

FIG. 7A illustrates a negative ion beam path vacuum system; FIG. 7B illustrates a support structure and foil; FIG. 7C illustrates a support structure;

Figure 1:
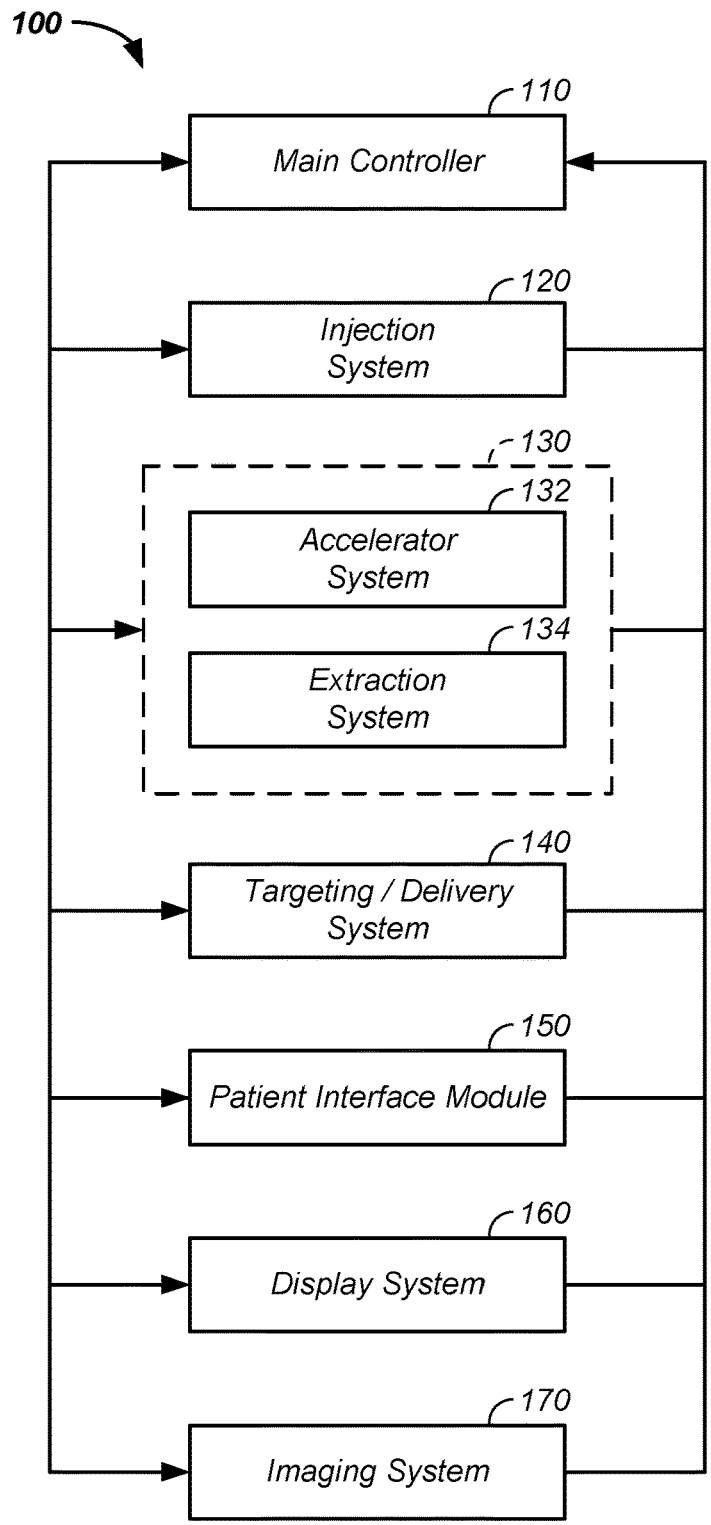
FIG. 1 illustrates component connections of a charged particle beam therapy system.

Elements and steps in the figures are illustrated for simplicity and clarity and have not necessarily been rendered according to any particular sequence. For example, steps that are performed concurrently or in different order are illustrated in the figures to help improve understanding of embodiments of the present invention.

DETAILED DESCRIPTION OF THE INVENTION

The invention relates generally to a charged particle treatment delivery control system and method of operation therefor.

In one embodiment, a treatment delivery control system (TDCS) or main controller is used to control multiple aspects of the cancer therapy system, including one or more of: an imaging system, such as a CT or PET; a positioner, such as a couch or patient interface module; an injector or injection system; a radio-frequency quadrupole system; a ring accelerator or synchrotron; an extraction system; an irradiation plan; and a display system. The TDCS is preferably a control system for automated cancer therapy once the patient is positioned. The TDCS integrates output of one or more of the below described cancer therapy system elements with inputs of one or more of the below described cancer therapy system elements. More generally, the TDCS controls or manages input and/or output of imaging, an irradiation plan, and charged particle delivery.

In another embodiment, the charged particle tomography apparatus is used in combination with a charged particle cancer therapy system. For example, tomographic imaging of a cancerous tumor is performed using charged particles generated with an injector, accelerator, and guided with a delivery system. The cancer therapy system uses the same injector, accelerator, and guided delivery system in delivering charged particles to the cancerous tumor. For example, the tomography apparatus and cancer therapy system use a common raster beam method and apparatus for treatment of solid cancers. More particularly, the invention comprises a multi-axis and/or multi-field raster beam charged particle accelerator used in tomography and cancer therapy. Optionally, the system independently controls patient translation position, patient rotation position, two-dimensional beam trajectory, delivered radiation beam energy, delivered radiation beam intensity, beam velocity, timing of charged particle delivery, and/or distribution of radiation striking healthy tissue. The system operates in conjunction with a negative ion beam source, synchrotron, patient positioning, imaging, and/or targeting method and apparatus to deliver an effective and uniform dose of radiation to a tumor while distributing radiation striking healthy tissue.

In various embodiments, the charged particle tomography system optionally includes any of:
- charged particle imaging at the same time or within seconds of delivery of charged particles for cancer therapy;
- ability to image the tumor by rotation of the patient;
- ability to collect tens or hundreds of rotationally independent images to construct the three-dimensional image of the tumor and the patient;
- adaptive charged particle therapy; and/or
- imaging of the patient in an upright position.

Herein, common elements of the tomography system are first described using a cancer therapy system. Any of the cancer therapy elements are optionally used in the later described charged particle tomography system.

Used in combination with the invention, novel design features of a charged particle beam cancer therapy system are described. Particularly, a negative ion beam source with novel features in the negative ion source, ion source vacuum system, ion beam focusing lens, and tandem accelerator is described. Additionally, the synchrotron includes: turning magnets, edge focusing magnets, magnetic field concentration magnets, winding and correction coils, flat magnetic field incident surfaces, and extraction elements, which minimize the overall size of the synchrotron, provide a tightly controlled proton beam, directly reduce the size of required magnetic fields, directly reduce required operating power, and allow continual acceleration of protons in a synchrotron even during a process of extracting protons from the synchrotron. The ion beam source system and synchrotron are preferably computer integrated with a patient imaging system and a patient interface including respiration monitoring sensors and patient positioning elements. Further, the system is integrated with intensity control of a charged particle beam, acceleration, extraction, and/or targeting method and apparatus. More particularly, intensity, energy, and timing control of a charged particle stream of a synchrotron is coordinated with patient positioning and tumor treatment. The synchrotron control elements allow tight control of the charged particle beam, which compliments the tight control of patient positioning to yield efficient treatment of a solid tumor with reduced tissue damage to surrounding healthy tissue. In addition, the system reduces the overall size of the synchrotron, provides a tightly controlled proton beam, directly reduces the size of required magnetic fields, directly reduces required operating power, and allows continual acceleration of protons in a synchrotron even during a process of extracting protons from the synchrotron. All of these systems are preferably used in conjunction with an X-ray system capable of collecting X-rays of a patient: (1) in a positioning, immobilization, and automated repositioning system for proton treatment; (2) at a specified moment of the patient's respiration cycle; and (3) using coordinated translation and rotation of the patient. Combined, the systems provide for efficient, accurate, and precise noninvasive tumor treatment with minimal damage to surrounding healthy tissue.

In various embodiments, the charged particle cancer therapy system incorporates any of:
- an injection system having a central magnetic member and a magnetic field separating high and low temperature plasma regions;
- a dual vacuum system creating a first partial pressure region on a plasma generation system side of a foil in a tandem accelerator and a second lower partial pressure region on the synchrotron side of the foil;
- a negative ion beam focusing system having a conductive mesh axially crossing the negative ion beam;
- a synchrotron having four straight sections and four turning sections;
- a synchrotron having no hexapole magnets;
- four bending magnets in each turning section of the synchrotron;
- a winding coil wrapping multiple bending magnets;
- a plurality of bending magnets that are beveled and charged particle focusing in each turning section;
- a magnetic field concentrating geometry approaching the gap through which the charged particles travel;
- correction coils for rapid magnetic field changes;
- magnetic field feedback sensors providing signal to the correction coils;
- integrated RF-amplifier microcircuits providing currents through loops about accelerating coils;
- a low density foil for charged particle extraction;
- a feedback sensor for measuring particle extraction allowing intensity control;
- a synchrotron independently controlling charged particle energy and intensity;
- a layer, after synchrotron extraction and before the tumor, for imaging the particle beam x-, y-axis position;
- a rotatable platform for turning the subject allowing multi-field imaging and/or multi-field proton therapy;
- a radiation plan dispersing ingress Bragg profile energy 360 degrees about the tumor;
- a long lifetime X-ray source;
- an X-ray source proximate the charged particle beam path;
- a multi-field X-ray system;
- positioning, immobilizing, and repositioning systems;
- respiratory sensors;
- simultaneous and independent control of:
  - x-axis beam control;
  - y-axis beam control;
  - irradiation beam energy;
  - irradiation beam intensity;
  - patient translation; and/or
  - patient rotation; and
- a system timing charged particle therapy to one or more of:
  - patient translation;
  - patient rotation; and
  - patient respiration.

In another embodiment, safety systems for a charged particle system are implemented. For example, the safety system includes any of: multiple X-ray images from multiple directions, a three-dimensional X-ray image, a proton beam approximating a path of an X-ray beam, tight control of a proton beam cross-sectional area with magnets, ability to control proton beam energy, ability to control proton beam energy, a set of patient movement constrains, a patient controlled charged particle interrupt system, distribution of radiation around a tumor, and timed irradiation in terms of respiration.

In yet another embodiment, the tumor is imaged from multiple directions in phase with patient respiration. For example, a plurality of two-dimensional pictures are collected that are all in the about the same phase of respiration. The two-dimensional pictures are combined to produce a three-dimensional picture of the tumor relative to the patient. One or more safety features are optionally used in the charged particle cancer therapy system independently and/or in combination with the three-dimensional imaging system, as described infra.

In still yet another embodiment, the system independently controls patient translation position, patient rotation position, two-dimensional beam trajectory, delivered radiation beam energy, delivered radiation beam intensity, timing of charged particle delivery, beam velocity, and/or distribution of radiation striking healthy tissue. The system operates in conjunction with a negative ion beam source, synchrotron, patient positioning, imaging, and/or targeting method and apparatus to deliver an effective and uniform dose of radiation to a tumor while distributing radiation striking healthy tissue.

Charged Particle Beam Therapy

Throughout this document, a charged particle beam therapy system, such as a proton beam, hydrogen ion beam, or carbon ion beam, is described. Herein, the charged particle beam therapy system is described using a proton beam. However, the aspects taught and described in terms of a proton beam are not intended to be limiting to that of a proton beam and are illustrative of a charged particle beam system. Any of the techniques described herein are equally applicable to any charged particle beam system.

Referring now to FIG. 1, a charged particle beam system 100 is illustrated. The charged particle beam preferably comprises a number of subsystems including any of: a main controller 110; an injection system 120; a synchrotron 130 that typically includes: (1) an accelerator system 132 and (2) an extraction system 134; a scanning/targeting/delivery system 140; a patient interface module 150; a display system 160; and/or an imaging system 170.

An exemplary method of use of the charged particle beam system 100 is provided. The main controller 110 controls one or more of the subsystems to accurately and precisely deliver protons to a tumor of a patient. For example, the main controller 110 obtains an image, such as a portion of a body and/or of a tumor, from the imaging system 170. The main controller 110 also obtains position and/or timing information from the patient interface module 150. The main controller 110 then optionally controls the injection system 120 to inject a proton into a synchrotron 130. The synchrotron typically contains at least an accelerator system 132 and an extraction system 134. The main controller 110 preferably controls the proton beam within the accelerator system, such as by controlling speed, trajectory, and timing of the proton beam. The main controller then controls extraction of a proton beam from the accelerator through the extraction system 134. For example, the controller controls timing, energy, and/or intensity of the extracted beam. The controller 110 also preferably controls targeting of the proton beam through the scanning/targeting/delivery system 140 to the patient interface module 150. One or more components of the patient interface module 150, such as translational and rotational position of the patient, are preferably controlled by the main controller 110. Further, display elements of the display system 160 are preferably controlled via the main controller 110. Displays, such as display screens, are typically provided to one or more operators and/or to one or more patients. In one embodiment, the main controller 110 times the delivery of the proton beam from all systems, such that protons are delivered in an optimal therapeutic manner to the tumor of the patient.

Herein, the main controller 110 refers to a single system controlling the charged particle beam system 100, to a single controller controlling a plurality of subsystems controlling the charged particle beam system 100, or to a plurality of individual controllers controlling one or more sub-systems of the charged particle beam system 100.

Figure 2:
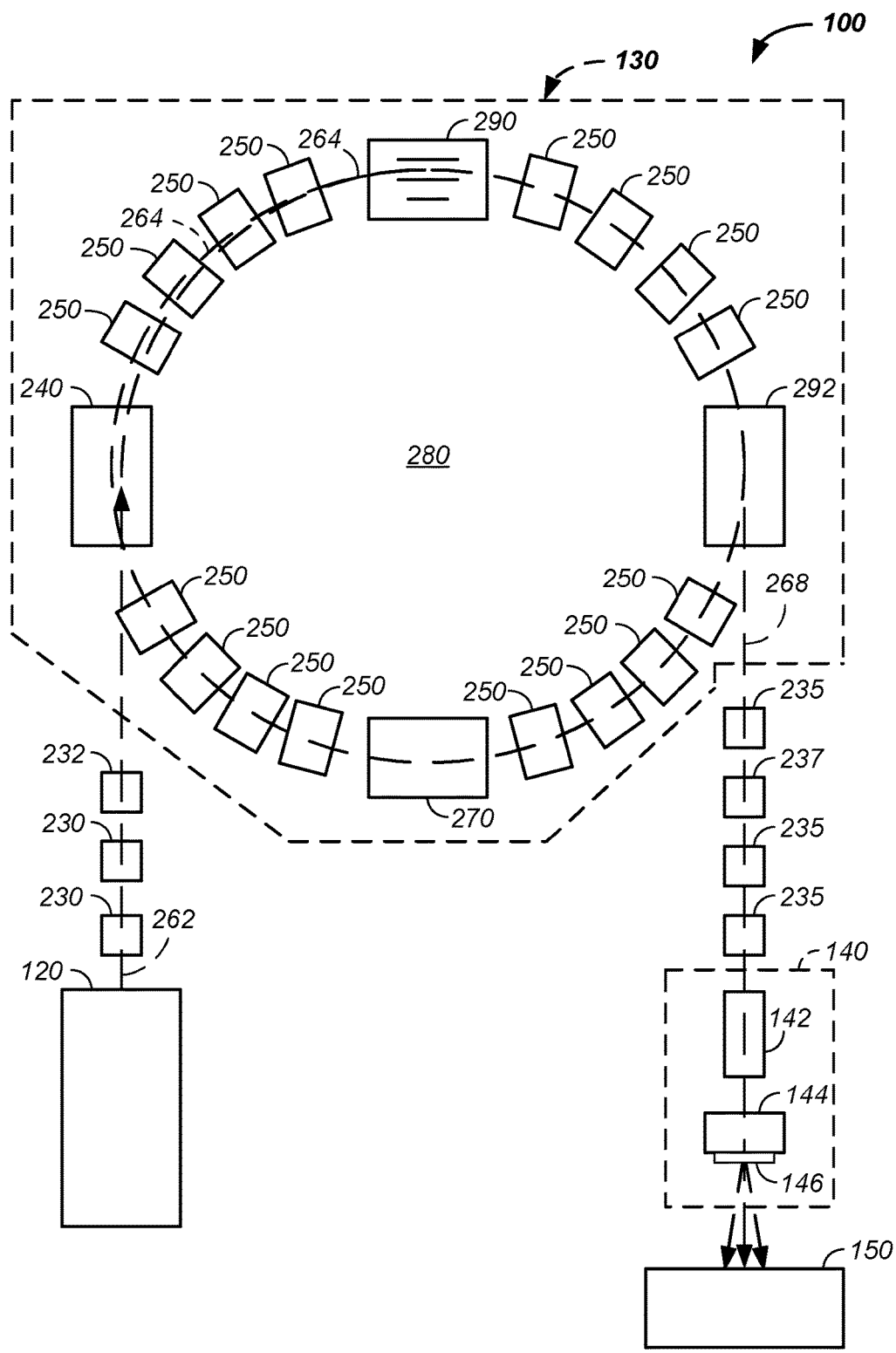
FIG. 2 illustrates a charged particle therapy system.

Referring now to FIG. 2, an illustrative exemplary embodiment of one version of the charged particle beam system 100 is provided. The number, position, and described type of components is illustrative and non-limiting in nature. In the illustrated embodiment, the injection system 120 or ion source or charged particle beam source generates protons. The protons are delivered into a vacuum tube that runs into, through, and out of the synchrotron. The generated protons are delivered along an initial path 262. Focusing magnets 230, such as quadrupole magnets or injection quadrupole magnets, are used to focus the proton beam path. A quadrupole magnet is a focusing magnet. An injector bending magnet 232 bends the proton beam toward the plane of the synchrotron 130. The focused protons having an initial energy are introduced into an injector magnet 240, which is preferably an injection Lamberson magnet. Typically, the initial beam path 262 is along an axis off of, such as above, a circulating plane of the synchrotron 130. The injector bending magnet 232 and injector magnet 240 combine to move the protons into the synchrotron 130. Main bending magnets, dipole magnets, turning magnets, or circulating magnets 250 are used to turn the protons along a circulating beam path 264. A dipole magnet is a bending magnet. The main bending magnets 250 bend the initial beam path 262 into a circulating beam path 264. In this example, the main bending magnets 250 or circulating magnets are represented as four sets of four magnets to maintain the circulating beam path 264 into a stable circulating beam path. However, any number of magnets or sets of magnets are optionally used to move the protons around a single orbit in the circulation process. The protons pass through an accelerator 270. The accelerator accelerates the protons in the circulating beam path 264. As the protons are accelerated, the fields applied by the magnets are increased. Particularly, the speed of the protons achieved by the accelerator 270 are synchronized with magnetic fields of the main bending magnets 250 or circulating magnets to maintain stable circulation of the protons about a central point or region 280 of the synchrotron. At separate points in time the accelerator 270/main bending magnet 250 combination is used to accelerate and/or decelerate the circulating protons while maintaining the protons in the circulating path or orbit. An extraction element of the inflector/deflector system 290 is used in combination with a Lamberson extraction magnet 292 to remove protons from their circulating beam path 264 within the synchrotron 130. One example of a deflector component is a Lamberson magnet. Typically the deflector moves the protons from the circulating plane to an axis off of the circulating plane, such as above the circulating plane. Extracted protons are preferably directed and/or focused using an extraction bending magnet 237 and extraction focusing magnets 235, such as quadrupole magnets along a transport path 268 into the scanning/targeting/delivery system 140. Two components of a scanning system 140 or targeting system typically include a first axis control 142, such as a vertical control, and a second axis control 144, such as a horizontal control. In one embodiment, the first axis control 142 allows for about 100 mm of vertical or y-axis scanning of the proton beam 268 and the second axis control 144 allows for about 700 mm of horizontal or x-axis scanning of the proton beam 268. A nozzle system 146 is used for imaging the proton beam and/or as a vacuum barrier between the low pressure beam path of the synchrotron and the atmosphere. Protons are delivered with control to the patient interface module 150 and to a tumor of a patient. All of the above listed elements are optional and may be used in various permutations and combinations. Each of the above listed elements are further described, infra.

Ion Beam Generation System

An ion beam generation system generates a negative ion beam, such as a hydrogen anion or H− beam; preferably focuses the negative ion beam; converts the negative ion beam to a positive ion beam, such as a proton or H+ beam; and injects the positive ion beam 262 into the synchrotron 130. Portions of the ion beam path are preferably under partial vacuum. Each of these systems are further described, infra.

Figure 3:
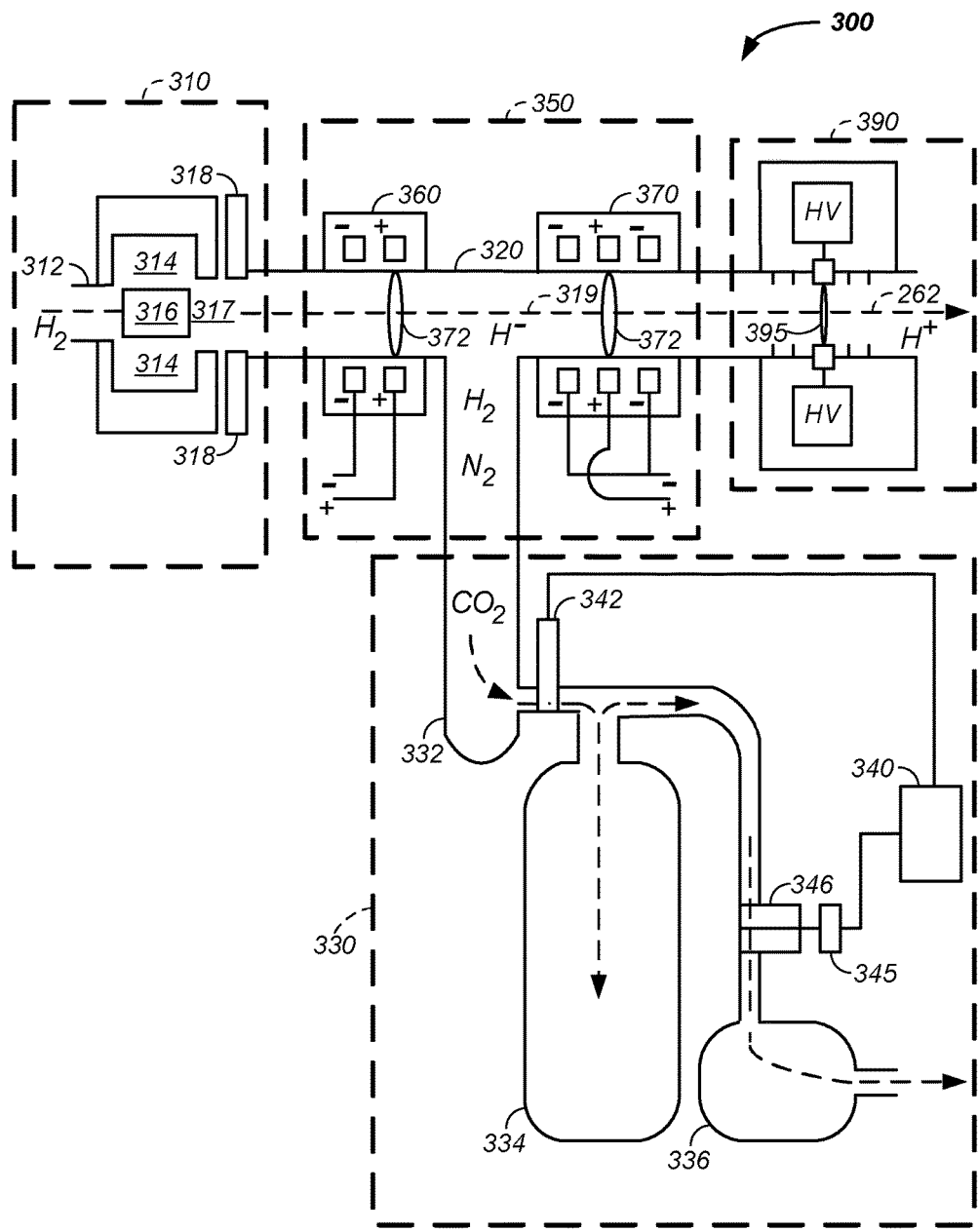
FIG. 3 illustrates an ion beam generation system.

Referring now to FIG. 3, an exemplary ion beam generation system 300 is illustrated. As illustrated, the ion beam generation system 300 has four major subsections: a negative ion source 310, a first partial vacuum system 330, an optional ion beam focusing system 350, and a tandem accelerator 390.

Still referring to FIG. 3, the negative ion source 310 preferably includes an inlet port 312 for injection of hydrogen gas into a high temperature plasma chamber 314. In one embodiment, the plasma chamber includes a magnetic material 316, which provides a magnetic field 317 between the high temperature plasma chamber 314 and a low temperature plasma region on the opposite side of the magnetic field barrier. An extraction pulse is applied to a negative ion extraction electrode 318 to pull the negative ion beam into a negative ion beam path 319, which proceeds through the first partial vacuum system 330, through the ion beam focusing system 350, and into the tandem accelerator 390.

Still referring to FIG. 3, the first partial vacuum system 330 is an enclosed system running from the hydrogen gas inlet port 312 to a foil 395 in the tandem accelerator 390. The foil 395 is preferably sealed directly or indirectly to the edges of the vacuum tube 320 providing for a higher pressure, such as about $10^{-5}$ torr, to be maintained on the first partial vacuum system side of the foil 395 and a lower pressure, such as about $10^{-7}$ torr, to be maintained on the synchrotron side of the foil. By only pumping first partial vacuum system 330 and by only semi-continuously operating the ion beam source vacuum based on sensor readings, the lifetime of the semi-continuously operating pump is extended. The sensor readings are further described, infra.

Still referring to FIG. 3, the first partial vacuum system 330 preferably includes: a first pump 332, such as a continuously operating pump and/or a turbo molecular pump; a large holding volume 334; and a semi-continuously operating pump 336. Preferably, a pump controller 340 receives a signal from a pressure sensor 342 monitoring pressure in the large holding volume 334. Upon a signal representative of a sufficient pressure in the large holding volume 334, the pump controller 340 instructs an actuator 345 to open a valve 346 between the large holding volume and the semi-continuously operating pump 336 and instructs the semi-continuously operating pump to turn on and pump to atmosphere residual gases out of the vacuum line 320 about the charged particle stream. In this fashion, the lifetime of the semi-continuously operating pump is extended by only operating semi-continuously and as needed. In one example, the semi-continuously operating pump 336 operates for a few minutes every few hours, such as 5 minutes every 4 hours, thereby extending a pump with a lifetime of about 2,000 hours to about 96,000 hours.

Further, by isolating the inlet gas from the synchrotron vacuum system, the synchrotron vacuum pumps, such as turbo molecular pumps can operate over a longer lifetime as the synchrotron vacuum pumps have fewer gas molecules to deal with. For example, the inlet gas is primarily hydrogen gas but may contain impurities, such as nitrogen and carbon dioxide. By isolating the inlet gases in the negative ion source system 310, first partial vacuum system 330, ion beam focusing system 350, and negative ion beam side of the tandem accelerator 390, the synchrotron vacuum pumps can operate at lower pressures with longer lifetimes, which increases operating efficiency of the synchrotron 130.

Still referring to FIG. 3, the optimal ion beam focusing system 350 preferably includes two or more electrodes where one electrode of each electrode pair partially obstructs the ion beam path with conductive paths 372, such as a conductive mesh. In the illustrated example, two ion beam focusing system sections are illustrated, a two electrode ion beam focusing section 360 and a three electrode ion beam focusing section 370. For a given electrode pair, electric field lines, running between the conductive mesh of a first electrode and a second electrode, provide inward forces focusing the negative ion beam. Multiple such electrode pairs provide multiple negative ion beam focusing regions. Preferably the two electrode ion focusing section 360 and the three electrode ion focusing section 370 are placed after the negative ion source and before the tandem accelerator and/or cover a space of about 0.5, 1, or 2 meters along the ion beam path 319. Ion beam focusing systems are further described, infra.

Still referring to FIG. 3, the tandem accelerator 390 preferably includes a foil 395, such as a carbon foil. The negative ions in the negative ion beam path 319 are converted to positive ions, such as protons, and the initial ion beam path 262 results. The foil 395 is preferably sealed directly or indirectly to the edges of the vacuum tube 320 providing for a higher pressure, such as about $10^{-5}$ torr, to be maintained on the side of the foil 395 having the negative ion beam path 319 and a lower pressure, such as about $10^{-7}$ torr, to be maintained on the side of the foil 390 having the proton ion beam path 262. Having the foil 395 physically separating the vacuum chamber 320 into two pressure regions allows for a system having fewer and/or smaller pumps to maintain the lower pressure system in the synchrotron 130 as the inlet hydrogen and its residuals are extracted in a separate contained and isolated space by the first partial vacuum system 330.

Negative Ion Source

Figure 4:
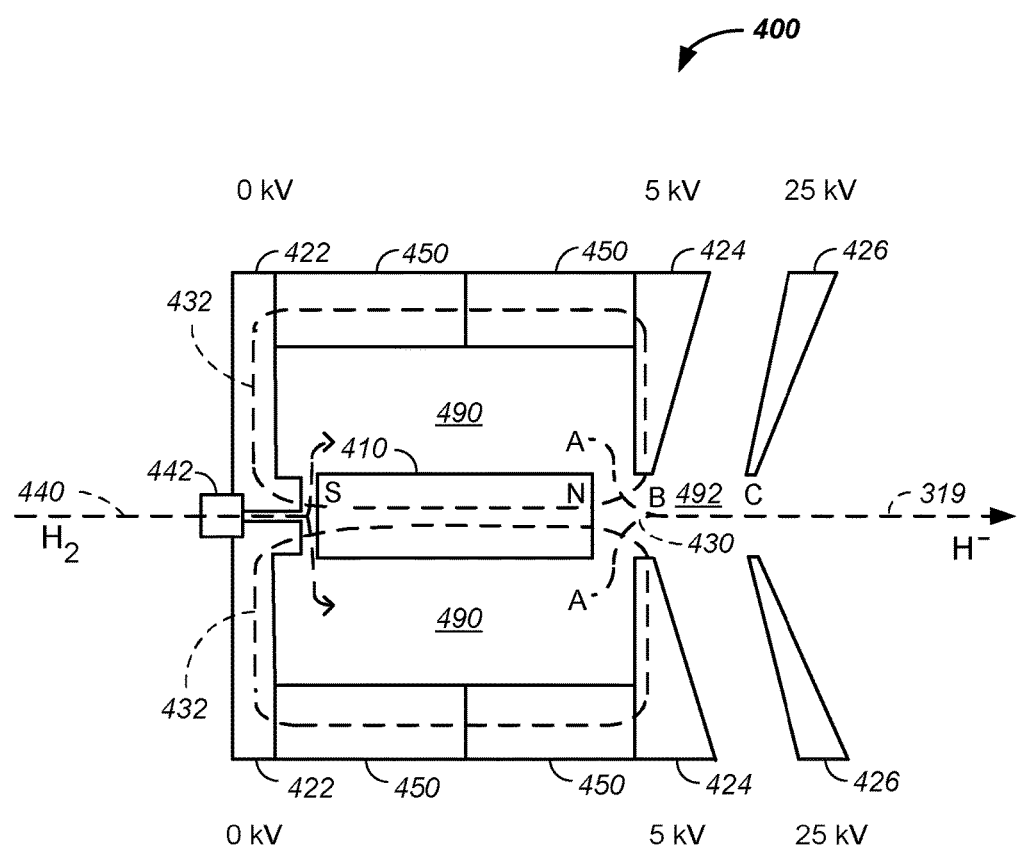
FIG. 4 illustrates a negative ion beam source.

An example of the negative ion source 310 is further described herein. Referring now to FIG. 4, a cross-section of an exemplary negative ion source system 400 is provided. The negative ion beam 319 is created in multiple stages. During a first stage, hydrogen gas is injected into a chamber. During a second stage, a negative ion is created by application of a first high voltage pulse, which creates a plasma about the hydrogen gas to create negative ions. During a third stage, a magnetic field filter is applied to components of the plasma. During a fourth stage, the negative ions are extracted from a low temperature plasma region, on the opposite side of the magnetic field barrier, by application of a second high voltage pulse. Each of the four stages are further described, infra. While the chamber is illustrated as a cross-section of a cylinder, the cylinder is exemplary only and any geometry applies to the magnetic loop containment walls, described infra.

In the first stage, hydrogen gas 440 is injected through the inlet port 312 into a high temperature plasma region 490.

The injection port 312 is open for a short period of time, such as less than about 1, 5, or 10 microseconds to minimize vacuum pump requirements to maintain vacuum chamber 320 requirements. The high temperature plasma region is maintained at reduced pressure by the partial vacuum system 330. The injection of the hydrogen gas is optionally controlled by the main controller 110, which is responsive to imaging system 170 information and patient interface module 150 information, such as patient positioning and period in a respiration cycle.

In the second stage, a high temperature plasma region is created by applying a first high voltage pulse across a first electrode 422 and a second electrode 424. For example a 5 kV pulse is applied for about 20 microseconds with 5 kV at the second electrode 424 and about 0 kV applied at the first electrode 422. Hydrogen in the chamber is broken, in the high temperature plasma region 490, into component parts, such as any of: atomic hydrogen, $H^0$, a proton, $H^+$, an electron, $e^-$, and a hydrogen anion, $H^-$.

In the third stage, the high temperature plasma region 490 is at least partially separated from a low temperature plasma region 492 by the magnetic field 317 or in this specific example a magnetic field barrier 430. High energy electrons are restricted from passing through the magnetic field barrier 430. In this manner, the magnetic field barrier 430 acts as a filter between, zone A and zone B, in the negative ion source. Preferably, a central magnetic material 410, which is an example of the magnetic material 316, is placed within the high temperature plasma region 490, such as along a central axis of the high temperature plasma region 490. Preferably, the first electrode 422 and second electrode 424 are composed of magnetic materials, such as iron. Preferably, the outer walls 450 of the high temperature plasma region, such as cylinder walls, are composed of a magnetic material, such as a permanent magnet, ferric or iron based material, or a ferrite dielectric ring magnet. In this manner a magnetic field loop is created by: the central magnetic material 410, first electrode 422, the outer walls 450, the second electrode 424, and the magnetic field barrier 430. Again, the magnetic field barrier 430 restricts high energy electrons from passing through the magnetic field barrier 430. Low energy electrons interact with atomic hydrogen, $H^0$, to create a hydrogen anion, $H^-$, in the low temperature plasma region 492.

In the fourth stage, a second high voltage pulse or extraction pulse is applied at a third electrode 426. The second high voltage pulse is preferentially applied during the later period of application of the first high voltage pulse. For example, an extraction pulse of about 25 kV is applied for about the last 5 microseconds of the first creation pulse of about 20 microseconds. The potential difference, of about 20 kV, between the third electrode 426 and second electrode 424 extracts the negative ion, $H^-$, from the low temperature plasma region 492 and initiates the negative ion beam 319, from zone B to zone C.

The magnetic field barrier 430 is optionally created in number of ways. An example of creation of the magnetic field barrier 430 using coils is provided. In this example, the elements described, supra, in relation to FIG. 4 are maintained with several differences. First, the magnetic field is created using coils. An isolating material is preferably provided between the first electrode 422 and the cylinder walls 450 as well as between the second electrode 424 and the cylinder walls 450. The central material 410 and/or cylinder walls 450 are optionally metallic. In this manner, the coils create a magnetic field loop through the first electrode 422, isolating material, outer walls 450, second electrode 424, magnetic field barrier 430, and the central material 410. Essentially, the coils generate a magnetic field in place of production of the magnetic field by the magnetic material 410. The magnetic field barrier 430 operates as described, supra. Generally, any manner that creates the magnetic field barrier 430 between the high temperature plasma region 490 and low temperature plasma region 492 is functionally applicable to the ion beam extraction system 400, described herein.

Ion Beam Focusing System

Figure 5:
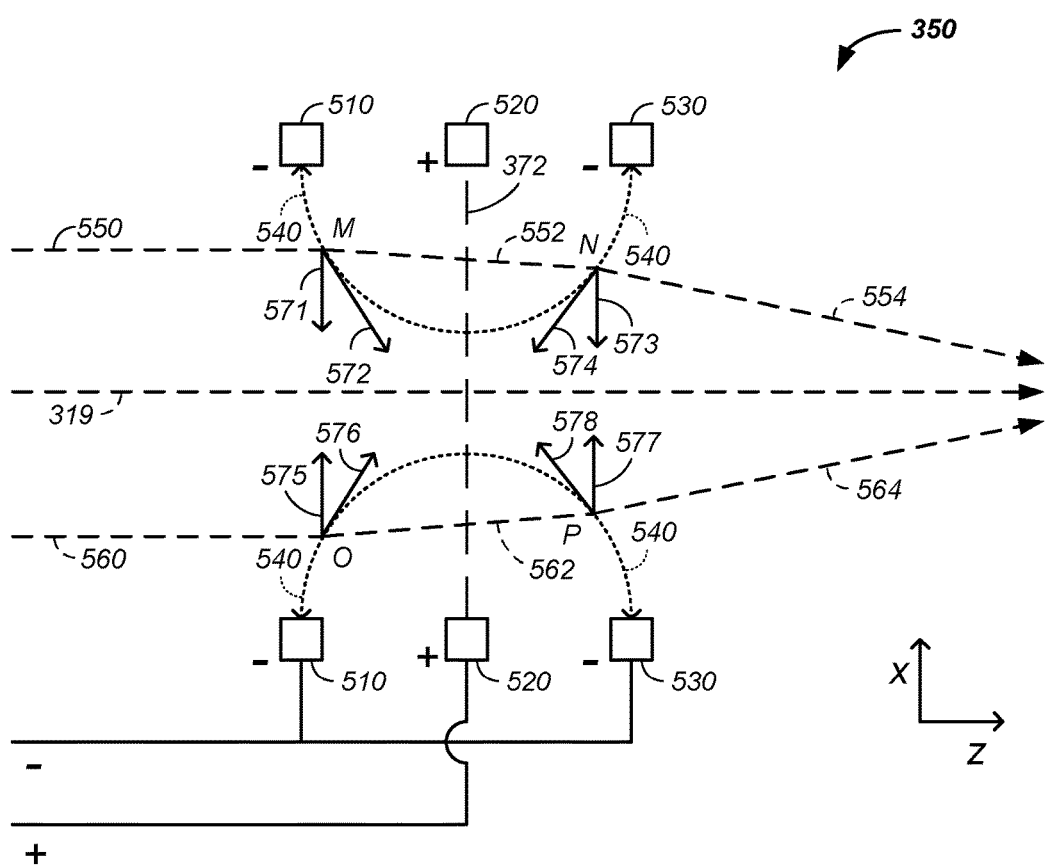
FIG. 5 illustrates an ion beam focusing system.
Figure 6A:
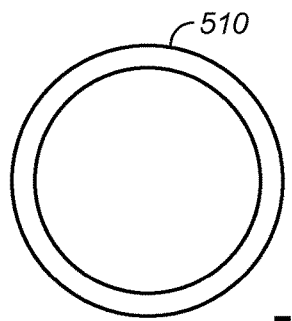
FIGS. 6(A-D) illustrate focusing electrodes about a negative ion beam path.
Figure 6B:
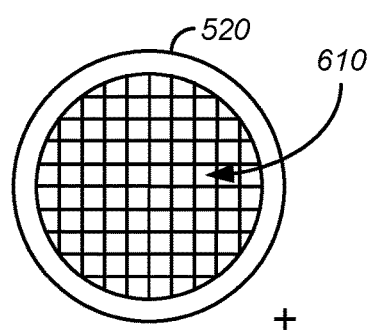
Figure 6C:
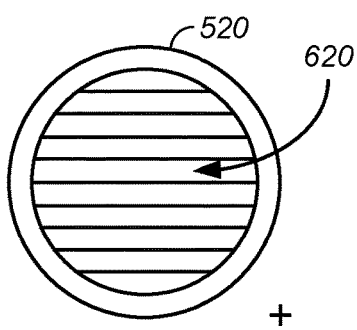
Figure 6D:
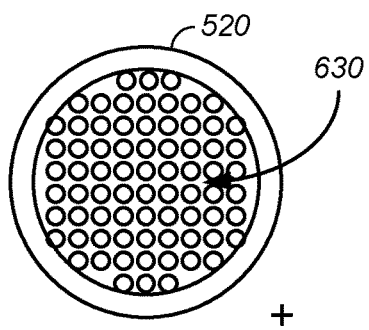

Referring now to FIG. 5, the ion beam focusing system 350 is further described. In this example, three electrodes are used. In this example, a first electrode 510 and third electrode 530 are both negatively charged and each is a ring electrode circumferentially enclosing or at least partially enclosing the negative ion beam path 319. A second electrode 520 is positively charged and is also a ring electrode at least partially and preferably substantially circumferentially enclosing the negative ion beam path. In addition, the second electrode includes one or more conducting paths 372 running through the negative ion beam path 319. For example, the conducting paths are a wire mesh, a conducting grid, or a series of substantially parallel conducting lines running across the second electrode. In use, electric field lines run from the conducting paths of the positively charged electrode to the negatively charged electrodes. For example, in use the electric field lines 540 run from the conducting paths 372 in the negative ion beam path 319 to the negatively charged electrodes 510, 530. Two ray trace lines 550, 560 of the negative ion beam path are used to illustrate focusing forces. In the first ray trace line 550, the negative ion beam encounters a first electric field line at point M. Negatively charged ions in the negative ion beam 550 encounter forces running up the electric field line 572, illustrated with an x-axis component vector 571. The x-axis component force vectors 571 alters the trajectory of the first ray trace line to a inward focused vector 552, which encounters a second electric field line at point N. Again, the negative ion beam 552 encounters forces running up the electric field line 574, illustrated as having an inward force vector with an x-axis component 573, which alters the inward focused vector 552 to a more inward focused vector 554. Similarly, in the second ray trace line 560, the negative ion beam encounters a first electric field line at point O. Negatively charged ions in the negative ion beam encounter forces running up the electric field line 576, illustrated as having a force vector with an x-axis force 575. The inward force vector 575 alters the trajectory of the second ray trace line 560 to an inward focused vector 562, which encounters a second electric field line at point P. Again, the negative ion beam encounters forces running up the electric field line 578, illustrated as having force vector with an x-axis component 577, which alters the inward focused vector 562 to a more inward focused vector 564. The net result is a focusing effect on the negative ion beam. Each of the force vectors 572, 574, 576, 578 optionally has x and/or y force vector components resulting in a 3-dimensional focusing of the negative ion beam path. Naturally, the force vectors are illustrative in nature, many electric field lines are encountered, and the focusing effect is observed at each encounter resulting in integral focusing. The example is used to illustrate the focusing effect.

Still referring to FIG. 5, optionally any number of electrodes are used, such as 2, 3, 4, 5, 6, 7, 8, or 9 electrodes, to focus the negative ion beam path where every other electrode, in a given focusing section, is either positively or negatively charged. For example, three focusing sections are optionally used. In the first ion focusing section 360, a pair of electrodes is used where the first electrode encountered along the negative ion beam path is negatively charged and the second electrode is positively charged, resulting in focusing of the negative ion beam path. In the second ion focusing section 370, two pairs of electrodes are used, where a common positively charged electrode with a conductive mesh running through the negatively ion beam path 319 is used. Thus, in the second ion focusing section 370, the first electrode encountered along the negative ion beam path is negatively charged and the second electrode is positively charged, resulting in focusing of the negative ion beam path. Further, in the second ion focusing section, moving along the negative ion beam path, a second focusing effect is observed between the second positively charged electrode and a third negatively charged electrode. In this example, a third ion focusing section is used that again has three electrodes, which acts in the fashion of the second ion focusing section, described supra.

Referring now to FIGS. 6(A-D), the central region of the electrodes in the ion beam focusing system 350 is further described. Referring now to FIG. 6A, the central region of the negatively charged ring electrode 510 is preferably void of conductive material. Referring now to FIGS. 6(B-D), the central region of positively charged electrode ring 520 preferably contains conductive paths 372. Preferably, the conductive paths 372 or conductive material within the positively charged electrode ring 520 blocks about 1, 2, 5, or 10 percent of the area and more preferably blocks about five percent of the cross-sectional area of the negative ion beam path 319. Referring now to FIG. 6B, one option is a conductive mesh 610. Referring now to FIG. 6C, a second option is a series of conductive lines 620 running substantially in parallel across the positively charged electrode ring 520 that surrounds a portion of the negative ion beam path 319. Referring now to FIG. 6D, a third option is to have a foil 630 or metallic layer cover all of the cross-sectional area of the negative ion beam path with holes punched through the material, where the holes take up about 90-99 percent and more preferably about 95 percent of the area of the foil. More generally, the pair of electrodes 510, 520 are configured to provide electric field lines that provide focusing force vectors to the negative ion beam 319 when the ions in the negative ion beam 319 translate through the electric field lines, as described supra.

In an example of a two electrode negative beam ion focusing system having a first cross-sectional diameter, $d_1$, the negative ions are focused to a second cross-sectional diameter, $d_2$, where $d_1 > d_2$. Similarly, in an example of a three electrode negative beam ion focusing system having a first ion beam cross-sectional diameter, $d_1$, the negative ions are focused using the three electrode system to a third negative ion beam cross-sectional diameter, $d_3$, where $d_1 > d_3$. For like potentials on the electrodes, the three electrode system provides tighter or stronger focusing compared to the two-electrode system, $d_3 < d_2$.

In the examples provided, supra, of a multi-electrode ion beam focusing system, the electrodes are rings. More generally, the electrodes are of any geometry sufficient to provide electric field lines that provide focusing force vectors to the negative ion beam when the ions in the negative ion beam 319 translate through the electric field lines, as described supra. For example, one negative ring electrode is optionally replaced by a number of negatively charged electrodes, such as about 2, 3, 4, 6, 8, 10, or more electrodes placed about the outer region of a cross-sectional area of the negative ion beam probe. Generally, more electrodes are required to converge or diverge a faster or higher energy beam.

In another embodiment, by reversing the polarity of electrodes in the above example, the negative ion beam is made to diverge. Thus, the negative ion beam path 319 is optionally focused and/or expanded using combinations of electrode pairs. For example, if the electrode having the mesh across the negative ion beam path is made negative, then the negative ion beam path is made to defocus. Hence, combinations of electrode pairs are used for focusing and defocusing a negative ion beam path, such as where a first pair includes a positively charged mesh for focusing and a where a second pair includes a negatively charged mesh for defocusing.

Tandem Accelerator

Referring now to FIG. 7A, the tandem accelerator 390 is further described. The tandem accelerator accelerates ions using a series of electrodes 710, 711, 712, 713, 714, 715. For example, negative ions, such as H$^-$, in the negative ion beam path are accelerated using a series of electrodes having progressively higher voltages relative to the voltage of the extraction electrode 426, or third electrode 426, of the negative ion beam source 310. For instance, the tandem accelerator 390 optionally has electrodes ranging from the 25 kV of the extraction electrode 426 to about 525 kV near the foil 395 in the tandem accelerator 390. Upon passing through the foil 395, the negative ion, H$^-$, loses two electrons to yield a proton, H$^+$, according to equation 1.

$$H^- \to H^+ + 2e^- \qquad (eq.\ 1)$$

The proton is further accelerated in the tandem accelerator using appropriate voltages at a multitude of further electrodes 713, 714, 715. The protons are then injected into the synchrotron 130 as described, supra.

Still referring to FIG. 7A, the foil 395 in the tandem accelerator 390 is further described. The foil 395 is preferably a very thin carbon film of about thirty to two hundred angstroms in thickness. The foil thickness is designed to both: (1) not block the ion beam and (2) allow the transfer of electrons yielding protons to form the proton beam path 262. The foil 395 is preferably substantially in contact with a support layer 720, such as a support grid. The support layer 720 provides mechanical strength to the foil 395 to combine to form a vacuum blocking element 725. The foil 395 blocks nitrogen, carbon dioxide, hydrogen, and other gases from passing and thus acts as a vacuum barrier. In one embodiment, the foil 395 is preferably sealed directly or indirectly to the edges of the vacuum tube 320 providing for a higher pressure, such as about $10^{-5}$ torr, to be maintained on the side of the foil 395 having the negative ion beam path 319 and a lower pressure, such as about $10^{-7}$ torr, to be maintained on the side of the foil 395 having the proton ion beam path 262. Having the foil 395 physically separating the vacuum chamber 320 into two pressure regions allows for a vacuum system having fewer and/or smaller pumps to maintain the lower pressure system in the synchrotron 130 as the inlet hydrogen and its residuals are extracted in a separate contained and isolated space by the first partial vacuum system 330. The foil 395 and support layer 720 are preferably attached to the structure 750 of the tandem accelerator 390 or vacuum tube 320 to form a pressure barrier using any mechanical means, such as a metal, plastic, or ceramic ring 730 compressed to the walls with an attachment screw 740. Any mechanical means for separating and sealing the two vacuum chamber sides with the foil 395 are equally applicable to this system. Referring now to FIG.

7B and FIG. 7C, the support structure 720 and foil 395 are, respectively, individually viewed in the x-, y-plane.

Figure 8:
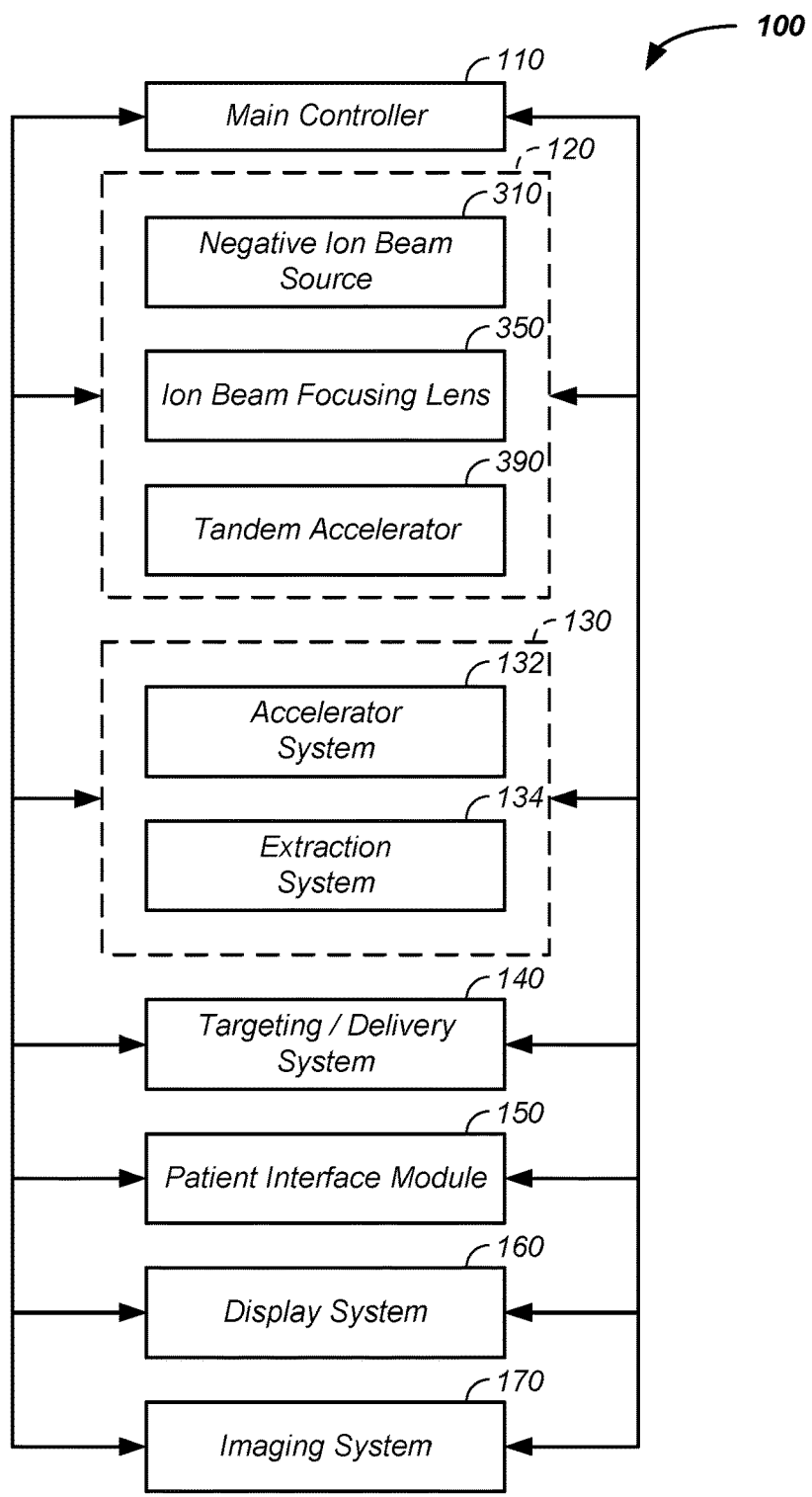
FIG. 8 is a particle beam therapy control flowchart.

Referring now to FIG. 8, another exemplary method of use of the charged particle beam system 100 is provided. The main controller 110, or one or more sub-controllers, controls one or more of the subsystems to accurately and precisely deliver protons to a tumor of a patient. For example, the main controller sends a message to the patient indicating when or how to breathe. The main controller 110 obtains a sensor reading from the patient interface module, such as a temperature breath sensor or a force reading indicative of where in a respiration cycle the subject is. Coordinated at a specific and reproducible point in the respiration cycle, the main controller collects an image, such as a portion of a body and/or of a tumor, from the imaging system 170. The main controller 110 also obtains position and/or timing information from the patient interface module 150. The main controller 110 then optionally controls the injection system 120 to inject hydrogen gas into a negative ion beam source 310 and controls timing of extraction of the negative ion from the negative ion beam source 310. Optionally, the main controller controls ion beam focusing using the ion beam focusing lens system 350; acceleration of the proton beam with the tandem accelerator 390; and/or injection of the proton into the synchrotron 130. The synchrotron typically contains at least an accelerator system 132 and an extraction system 134. The synchrotron preferably contains one or more of: turning magnets, edge focusing magnets, magnetic field concentration magnets, winding and correction coils, and flat magnetic field incident surfaces, some of which contain elements under control by the main controller 110. The main controller preferably controls the proton beam within the accelerator system, such as by controlling speed, trajectory, and/or timing of the proton beam. The main controller then controls extraction of a proton beam from the accelerator through the extraction system 134. For example, the controller controls timing, energy, and/or intensity of the extracted beam. The main controller 110 also preferably controls targeting of the proton beam through the targeting/delivery system 140 to the patient interface module 150. One or more components of the patient interface module 150 are preferably controlled by the main controller 110, such as vertical position of the patient, rotational position of the patient, and patient chair positioning/stabilization/immobilization/control elements. Further, display elements of the display system 160 are preferably controlled via the main controller 110. Displays, such as display screens, are typically provided to one or more operators and/or to one or more patients. In one embodiment, the main controller 110 times the delivery of the proton beam from all systems, such that protons are delivered in an optimal therapeutic manner to the tumor of the patient.

A radio frequency quadrupole (RFQ) accelerator 4850 is optionally used as an injector of charged particles to the synchrotron. For example, the RFQ accelerator is a 1.6 MeV RFQ accelerator used as an injector for a synchrotron and a buncher/debuncher cavity as necessary. The RFQ accelerator optionally operates at 425±0.05 MHz, has an ion injector output energy of about 30 keV, has an RFQ output energy of nominally 1/60±0.01 MeV, has a maximum pulsed output current of f10 mA, an output beam pulse flat-top width of 1-5 microseconds, and a beam pulse repetition rate of 0.1 to 20 Hz.

Synchrotron

Herein, the term synchrotron is used to refer to a system maintaining the charged particle beam in a circulating path. Further, the charged particle beam is referred to herein as circulating along a circulating path about a central point of the synchrotron. The circulating path is alternatively referred to as an orbiting path; however, the orbiting path does not refer to a perfect circle or ellipse, rather it refers to cycling of the protons around a central point or region 280.

Circulating System

Figure 9:
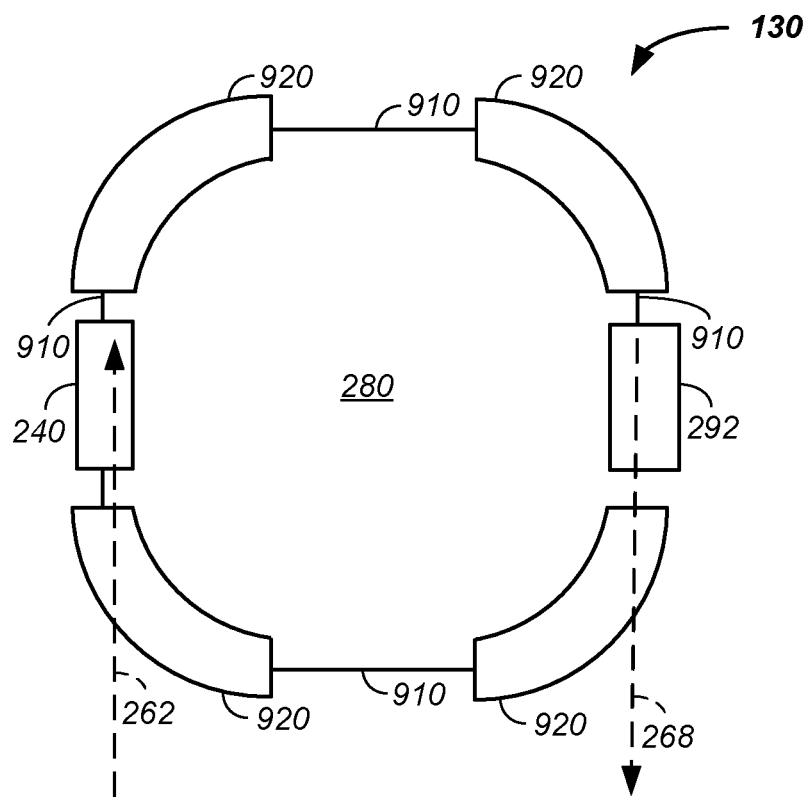
FIG. 9 illustrates straight and turning sections of a synchrotron.

Referring now to FIG. 9, the synchrotron 130 preferably comprises a combination of straight sections 910 and ion beam turning sections 920. Hence, the circulating path of the protons is not circular in a synchrotron, but is rather a polygon with rounded corners.

In one illustrative embodiment, the synchrotron 130, which is also referred to as an accelerator system, has four straight sections or elements and four turning sections. Examples of straight sections 910 include the: inflector 240, accelerator 270, extraction system 290, and deflector 292. Along with the four straight sections are four ion beam turning sections 920, which are also referred to as magnet sections or turning sections. Turning sections are further described, infra.

Referring still to FIG. 9, an exemplary synchrotron is illustrated. In this example, protons delivered along the initial proton beam path 262 are inflected into the circulating beam path with the inflector 240 and after acceleration are extracted via a deflector 292 to the beam transport path 268. In this example, the synchrotron 130 comprises four straight sections 910 and four bending or turning sections 920 where each of the four turning sections use one or more magnets to turn the proton beam about ninety degrees. As is further described, infra, the ability to closely space the turning sections and efficiently turn the proton beam results in shorter straight sections. Shorter straight sections allow for a synchrotron design without the use of focusing quadrupoles in the circulating beam path of the synchrotron. The removal of the focusing quadrupoles from the circulating proton beam path results in a more compact design. In this example, the illustrated synchrotron has about a five meter diameter versus eight meter and larger cross-sectional diameters for systems using a quadrupole focusing magnet in the circulating proton beam path.

Figure 10:
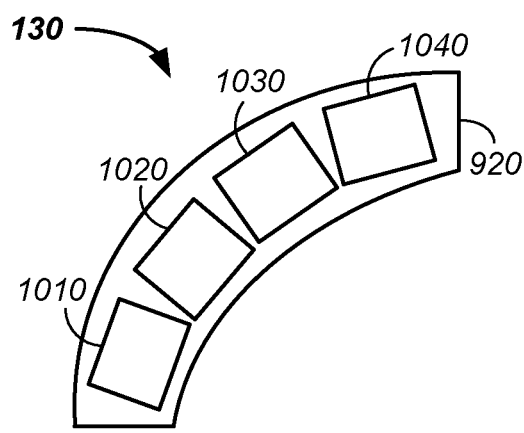
FIG. 10 illustrates bending magnets of a synchrotron.

Referring now to FIG. 10, additional description of the first bending or turning section 920 is provided. Each of the turning sections preferably comprise multiple magnets, such as about 2, 4, 6, 8, 10, or 12 magnets. In this example, four turning magnets 1010, 1020, 1030, 1040 in the first turning section 920 are used to illustrate key principles, which are the same regardless of the number of magnets in a turning section 920. The turning magnets 1010, 1020, 1030, 1040 are particular types of main bending or circulating magnets 250.

In physics, the Lorentz force is the force on a point charge due to electromagnetic fields. The Lorentz force is given by equation 2 in terms of magnetic fields with the electron field terms not included.

$$F = q(v \times B) \tag{eq. 2}$$

In equation 2, F is the force in newtons; q is the electric charge in coulombs; B is the magnetic field in Teslas; and v is the instantaneous velocity of the particles in meters per second.

Figure 11:
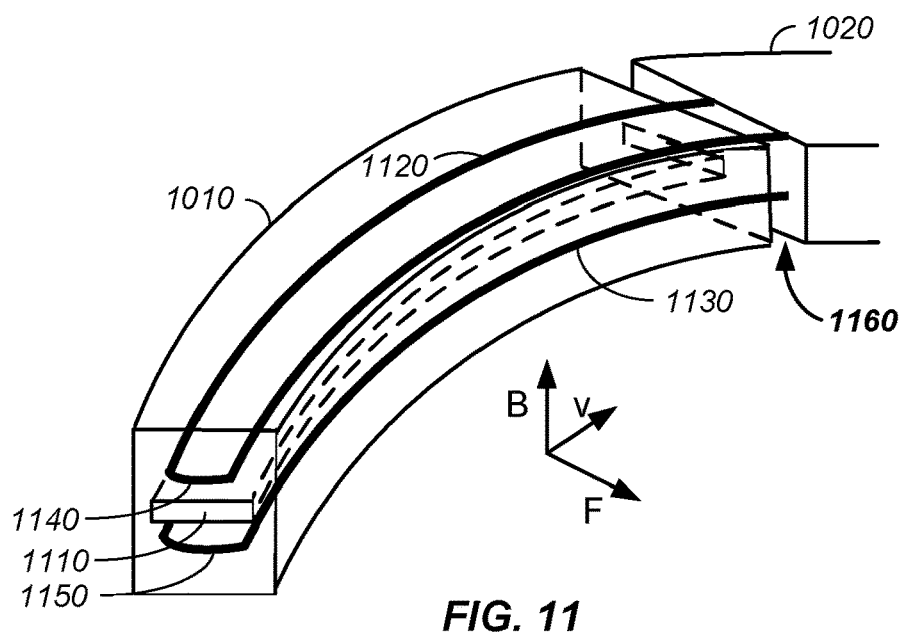
FIG. 11 provides a perspective view of a bending magnet.

Referring now to FIG. 11, an example of a single magnet bending or turning section 1010 is expanded. The turning section includes a gap 1110 through which protons circulate. The gap 1110 is preferably a flat gap, allowing for a magnetic field across the gap 1110 that is more uniform, even, and intense. A magnetic field enters the gap 1110 through a magnetic field incident surface and exits the gap 1110 through a magnetic field exiting surface. The gap 1110 runs in a vacuum tube between two magnet halves. The gap 1110 is controlled by at least two parameters: (1) the gap 1110 is kept as large as possible to minimize loss of protons and (2) the gap 1110 is kept as small as possible to minimize magnet sizes and the associated size and power requirements of the magnet power supplies. The flat nature of the gap 1110 allows for a compressed and more uniform magnetic field across the gap 1110. One example of a gap dimension is to accommodate a vertical proton beam size of about two centimeters with a horizontal beam size of about five to six centimeters.

As described, supra, a larger gap size requires a larger power supply. For instance, if the gap 1110 size doubles in vertical size, then the power supply requirements increase by about a factor of four. The flatness of the gap 1110 is also important. For example, the flat nature of the gap 1110 allows for an increase in energy of the extracted protons from about 250 to about 330 MeV. More particularly, if the gap 1110 has an extremely flat surface, then the limits of a magnetic field of an iron magnet are reachable. An exemplary precision of the flat surface of the gap 1110 is a polish of less than about five microns and preferably with a polish of about one to three microns. Unevenness in the surface results in imperfections in the applied magnetic field. The polished flat surface spreads unevenness of the applied magnetic field.

Still referring to FIG. 11, the charged particle beam moves through the gap 1110 with an instantaneous velocity, v. A first magnetic coil 1120 and a second magnetic coil 1130 run above and below the gap 1110, respectively. Current running through the coils 1120, 1130 results in a magnetic field, B, running through the single magnet turning section 1010. In this example, the magnetic field, B, runs upward, which results in a force, F, pushing the charged particle beam inward toward a central point of the synchrotron, which turns the charged particle beam in an arc.

Still referring to FIG. 11, a portion of an optional second magnet bending or turning section 1020 is illustrated. The coils 1120, 1130 typically have return elements 1140, 1150 or turns at the end of one magnet, such as at the end of the first magnet turning section 1010. The turns 1140, 1150 take space. The space reduces the percentage of the path about one orbit of the synchrotron that is covered by the turning magnets. This leads to portions of the circulating path where the protons are not turned and/or focused and allows for portions of the circulating path where the proton path defocuses. Thus, the space results in a larger synchrotron. Therefore, the space between magnet turning sections 1160 is preferably minimized. The second turning magnet is used to illustrate that the coils 1120, 1130 optionally run along a plurality of magnets, such as 2, 3, 4, 5, 6, or more magnets. Coils 1120, 1130 running across multiple turning section magnets allows for two turning section magnets to be spatially positioned closer to each other due to the removal of the steric constraint of the turns, which reduces and/or minimizes the space 1160 between two turning section magnets.

Figure 13:
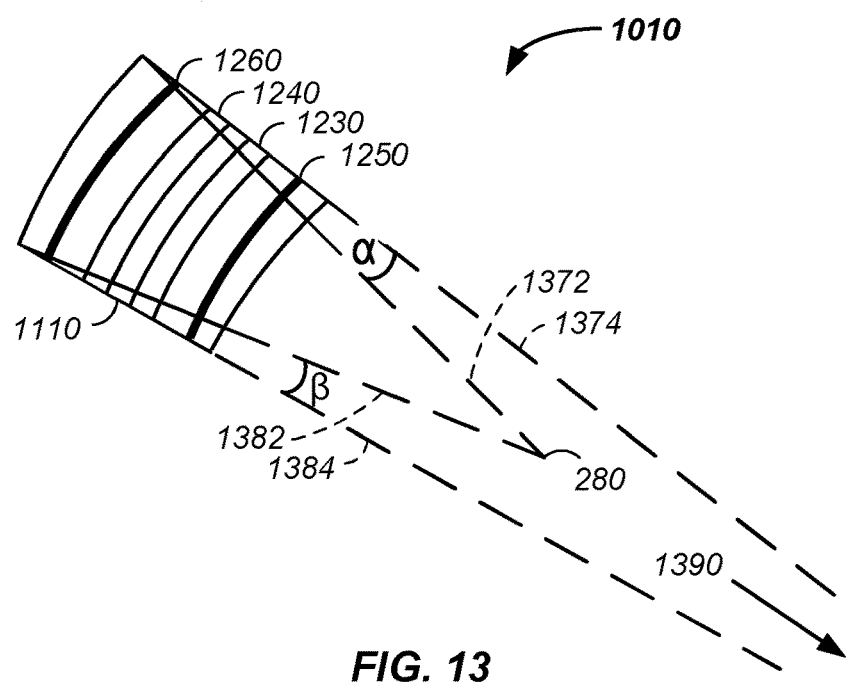
FIG. 13 illustrates a cross-sectional view of a bending magnet.
Figure 12:
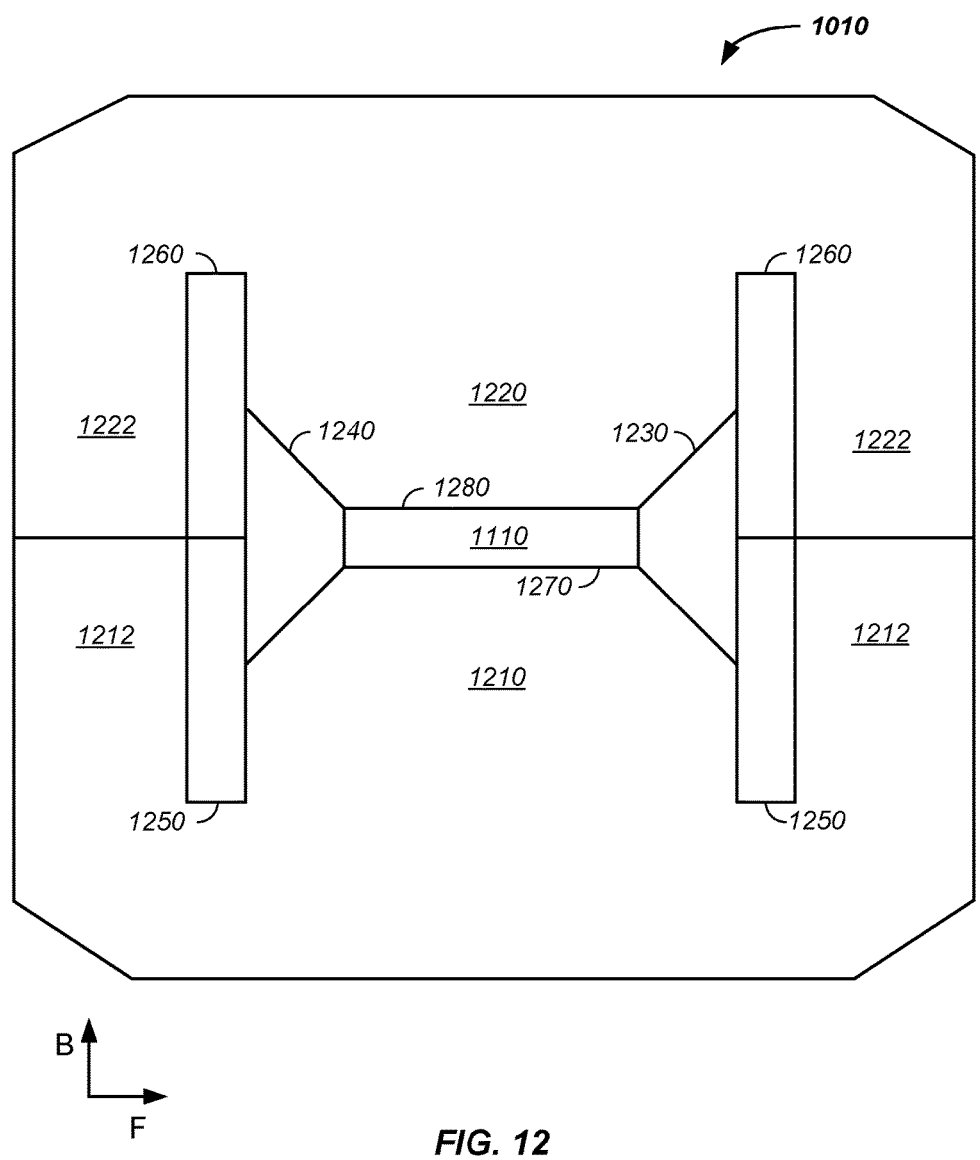
FIG. 12 illustrates a cross-sectional view of a bending magnet.

Referring now to FIG. 12 and FIG. 13, two illustrative 90 degree rotated cross-sections of single magnet bending or turning sections 1010 are presented. The magnet assembly has a first magnet 1210 and a second magnet 1220. A magnetic field induced by coils, described infra, runs between the first magnet 1210 to the second magnet 1220 across the gap 1110. Return magnetic fields run through a first yoke 1212 and second yoke 1222. The combined cross-section area of the return yokes roughly approximates the cross-sectional area of the first magnet 1210 or second magnet 1220. The charged particles run through the vacuum tube in the gap 1110. As illustrated, protons run into FIG. 12 through the gap 1110 and the magnetic field, illustrated as vector B, applies a force F to the protons pushing the protons towards the center of the synchrotron, which is off page to the right in FIG. 12. The magnetic field is created using windings. A first coil is used to form a first winding coil 1250 and a second coil of wire is used to form a second winding coil 1260. Isolating or concentrating gaps 1230, 1240, such as air gaps, isolate the iron based yokes from the gap 1110. The gap 1110 is approximately flat to yield a uniform magnetic field across the gap 1110, as described supra.

Still referring to FIG. 13, the ends of a single bending or turning magnet are preferably beveled. Nearly perpendicular or right angle edges of a turning magnet 1010 are represented by dashed lines 1374, 1384. The dashed lines 1374, 1384 intersect at a point 1390 beyond the center of the synchrotron 280. Preferably, the edge of the turning magnet is beveled at angles alpha, $\alpha$, and beta, $\beta$, which are angles formed by a first line 1372, 1382 going from an edge of the turning magnet 1010 and the center 280 and a second line 1374, 1384 going from the same edge of the turning magnet and the intersecting point 1390. The angle alpha is used to describe the effect and the description of angle alpha applies to angle beta, but angle alpha is optionally different from angle beta. The angle alpha provides an edge focusing effect. Beveling the edge of the turning magnet 1010 at angle alpha focuses the proton beam.

Multiple turning magnets provide multiple magnet edges that each have edge focusing effects in the synchrotron 130. If only one turning magnet is used, then the beam is only focused once for angle alpha or twice for angle alpha and angle beta. However, by using smaller turning magnets, more turning magnets fit into the turning sections 920 of the synchrotron 130. For example, if four magnets are used in a turning section 920 of the synchrotron, then for a single turning section there are eight possible edge focusing effect surfaces, two edges per magnet. The eight focusing surfaces yield a smaller cross-sectional beam size, which allows the use of a smaller gap.

The use of multiple edge focusing effects in the turning magnets results in not only a smaller gap 1110, but also the use of smaller magnets and smaller power supplies. For a synchrotron 130 having four turning sections 920 where each turning sections has four turning magnets and each turning magnet has two focusing edges, a total of thirty-two focusing edges exist for each orbit of the protons in the circulating path of the synchrotron 130. Similarly, if 2, 6, or 8 magnets are used in a given turning section, or if 2, 3, 5, or 6 turning sections are used, then the number of edge focusing surfaces expands or contracts according to equation 3.

$$TFE = NTS * \frac{M}{NTS} * \frac{FE}{M} \qquad (\text{eq. 3})$$

where TFE is the number of total focusing edges, NTS is the number of turning sections, M is the number of magnets, and FE is the number of focusing edges. Naturally, not all magnets are necessarily beveled and some magnets are optionally beveled on only one edge.

The inventors have determined that multiple smaller magnets have benefits over fewer larger magnets. For example, the use of 16 small magnets yields 32 focusing edges whereas the use of 4 larger magnets yields only 8 focusing edges. The use of a synchrotron having more focusing edges results in a circulating path of the synchrotron built without the use of focusing quadrupole magnets. All prior art synchrotrons use quadrupoles in the circulating path of the synchrotron. Further, the use of quadrupoles in the circulating path necessitates additional straight sections in the circulating path of the synchrotron. Thus, the use of quadrupoles in the circulating path of a synchrotron results in synchrotrons having larger diameters, larger circulating beam pathlengths, and/or larger circumferences.

In various embodiments of the system described herein, the synchrotron has any combination of:

- at least four and preferably six, eight, ten, or more edge focusing edges per 90 degrees of turn of the charged particle beam in a synchrotron having four turning sections;
- at least about sixteen and preferably about twenty-four, thirty-two, or more edge focusing edges per orbit of the charged particle beam in the synchrotron;
- only four turning sections where each of the turning sections includes at least four and preferably eight edge focusing edges;
- an equal number of straight sections and turning sections;
- exactly four turning sections;
- at least four focusing edges per turning section;
- no quadrupoles in the circulating path of the synchrotron;
- a rounded corner rectangular polygon configuration;
- a circumference of less than sixty meters;
- a circumference of less than sixty meters and thirty-two edge focusing surfaces; and/or
- any of about eight, sixteen, twenty-four, or thirty-two non-quadrupole magnets per circulating path of the synchrotron, where the non-quadrupole magnets include edge focusing edges.

Flat Gap Surface

While the gap surface is described in terms of the first turning magnet 1010, the discussion applies to each of the turning magnets in the synchrotron. Similarly, while the gap 1110 surface is described in terms of the magnetic field incident surface 1270, the discussion additionally optionally applies to the magnetic field exiting surface 1280.

Referring again to FIG. 12, the incident magnetic field surface 1270 of the first magnet 1210 is further described. FIG. 12 is not to scale and is illustrative in nature. Local imperfections or unevenness in quality of the finish of the incident surface 1270 results in inhomogeneities or imperfections in the magnetic field applied to the gap 1110. The magnetic field incident surface 1270 and/or exiting surface 1280 of the first magnet 1210 is preferably about flat, such as to within about a zero to three micron finish polish or less preferably to about a ten micron finish polish. By being very flat, the polished surface spreads the unevenness of the applied magnetic field across the gap 1110. The very flat surface, such as about 0, 1, 2, 4, 6, 8, 10, 15, or 20 micron finish, allows for a smaller gap size, a smaller applied magnetic field, smaller power supplies, and tighter control of the proton beam cross-sectional area.

Figure 14:
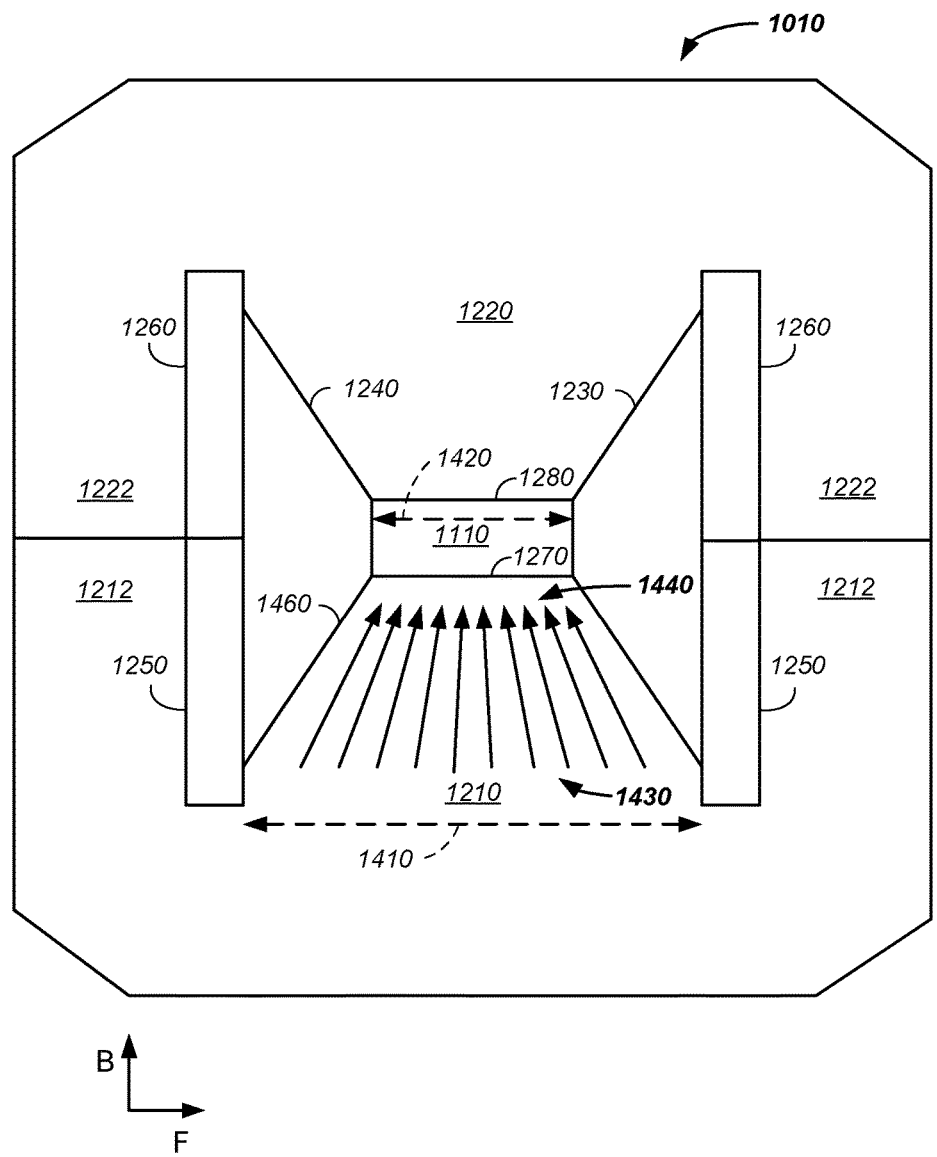
FIG. 14 illustrates magnetic field concentration in a bending magnet.

Referring now to FIG. 14, additional optional magnet elements, of the magnet cross-section illustratively represented in FIG. 12, are described. The first magnet 1210 preferably contains an initial cross-sectional distance 1410 of the iron based core. The contours of the magnetic field are shaped by the magnets 1210, 1220 and the yokes 1212, 1222. The iron based core tapers to a second cross-sectional distance 1420. The shape of the magnetic field vector 1440 is illustrative only. The magnetic field in the magnet preferentially stays in the iron based core as opposed to the gaps 1230, 1240. As the cross-sectional distance decreases from the initial cross-sectional distance 1410 to the final cross-sectional distance 1420, the magnetic field concentrates. The change in shape of the magnet from the longer distance 1410 to the smaller distance 1420 acts as an amplifier. The concentration of the magnetic field is illustrated by representing an initial density of magnetic field vectors 1430 in the initial cross-section 1410 to a concentrated density of magnetic field vectors 1440 in the final cross-section 1420. The concentration of the magnetic field due to the geometry of the turning magnets results in fewer winding coils 1250, 1260 being required and also a smaller power supply to the coils being required.

In one example, the initial cross-section distance 1410 is about fifteen centimeters and the final cross-section distance 1420 is about ten centimeters. Using the provided numbers, the concentration of the magnetic field is about 15/10 or 1.5 times at the incident surface 1270 of the gap 1110, though the relationship is not linear. The taper 1460 has a slope, such as about twenty, forty, or sixty degrees. The concentration of the magnetic field, such as by 1.5 times, leads to a corresponding decrease in power consumption requirements to the magnets.

Figure 15:
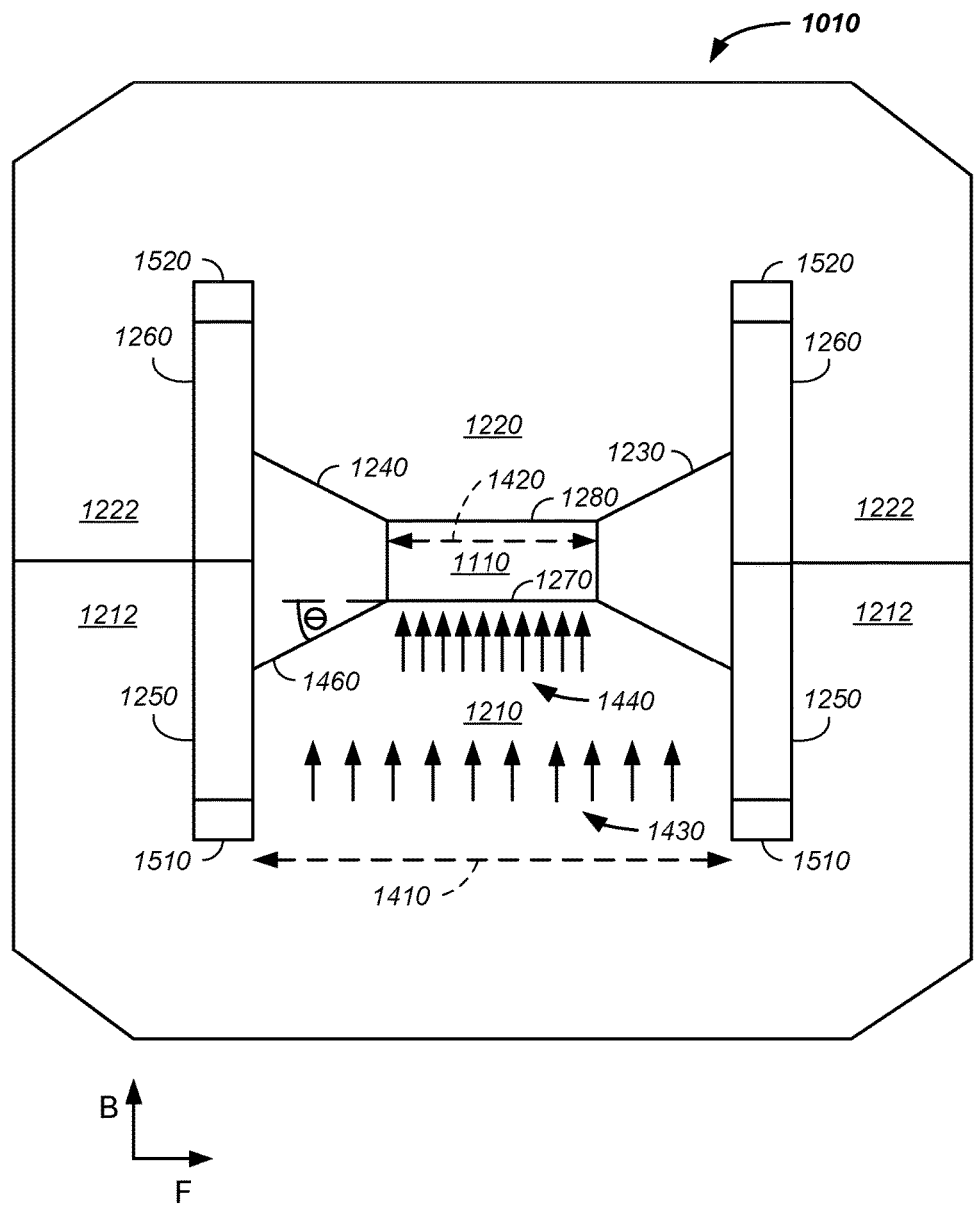
FIG. 15 illustrates correction coils in a bending magnet.

Referring now to FIG. 15, an additional example of geometry of the magnet used to concentrate the magnetic field is illustrated. As illustrated in FIG. 14, the first magnet 1210 preferably contains an initial cross-sectional distance 1410 of the iron based core. The contours of the magnetic field are shaped by the magnets 1210, 1220 and the yokes 1212, 1222. In this example, the core tapers to a second cross-sectional distance 1420 with a smaller angle theta, $\theta$. As described, supra, the magnetic field in the magnet preferentially stays in the iron based core as opposed to the gaps 1230, 1240. As the cross-sectional distance decreases from the initial cross-sectional distance 1410 to the final cross-sectional distance 1420, the magnetic field concentrates. The smaller angle, theta, results in a greater amplification of the magnetic field in going from the longer distance 1410 to the smaller distance 1420. The concentration of the magnetic field is illustrated by representing an initial density of magnetic field vectors 1430 in the initial cross-section 1410 to a concentrated density of magnetic field vectors 1440 in the final cross-section 1420. The concentration of the magnetic field due to the geometry of the turning magnets results in fewer winding coils 1250, 1260 being required and also a smaller power supply to the winding coils 1250, 1260 being required.

Still referring to FIG. 15, optional correction coils 1510, 1520 are illustrated that are used to correct the strength of one or more turning magnets. The correction coils 1520, 1530 supplement the winding coils 1250, 1260. The correction coils 1510, 1520 have correction coil power supplies that are separate from winding coil power supplies used with the winding coils 1250, 1260. The correction coil power supplies typically operate at a fraction of the power required compared to the winding coil power supplies, such as about 1, 2, 3, 5, 7, or 10 percent of the power and more preferably about 1 or 2 percent of the power used with the winding coils 1250, 1260. The smaller operating power applied to the correction coils 1510, 1520 allows for more accurate and/or precise control of the correction coils. The correction coils are used to adjust for imperfection in the turning magnets. Optionally, separate correction coils are used for each turning magnet allowing individual tuning of the magnetic field for each turning magnet, which eases quality requirements in the manufacture of each turning magnet.

Figure 16:
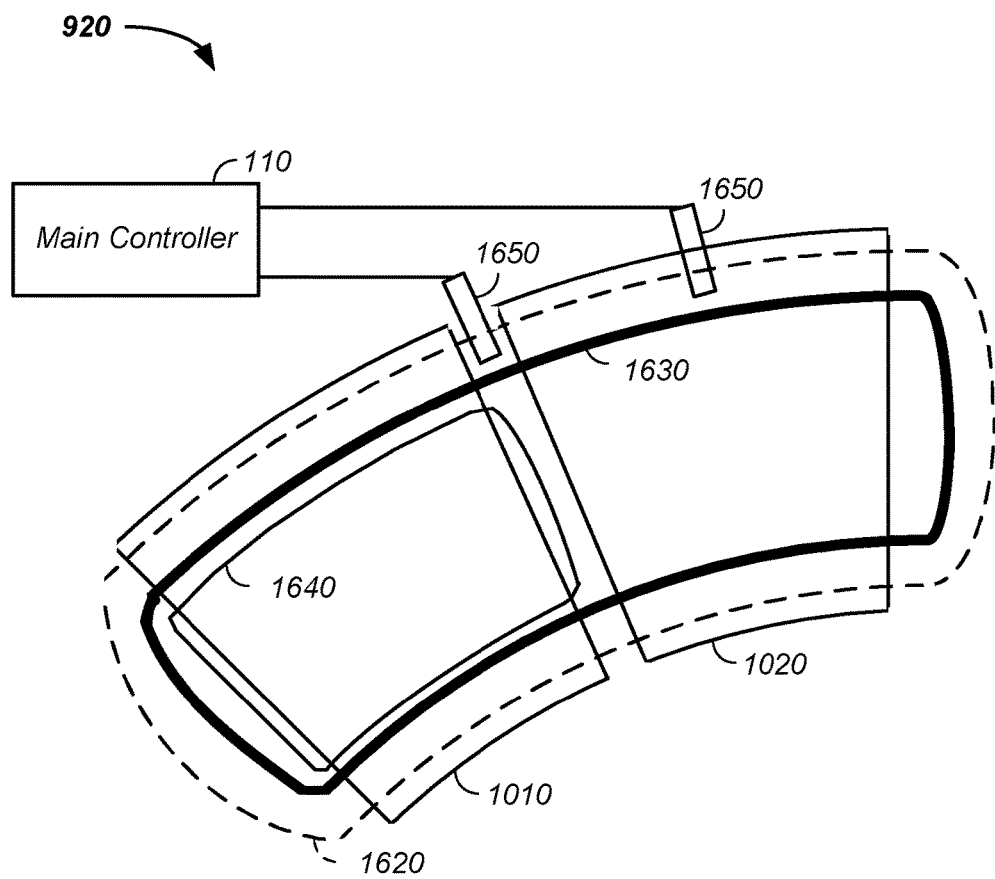
FIG. 16 illustrates a magnetic turning section of a synchrotron.

Referring now to FIG. 16, an example of winding coils 1630 and correction coils 1620 about a plurality of turning magnets 1010, 1020 in an ion beam turning section 920 is illustrated. The winding coils preferably cover 1, 2, or 4 turning magnets. One or more high precision magnetic field sensors 1650 are placed into the synchrotron and are used to measure the magnetic field at or near the proton beam path. For example, the magnetic sensors are optionally placed between turning magnets and/or within a turning magnet, such as at or near the gap 1110 or at or near the magnet core or yoke. The sensors are part of a feedback system to the correction coils, which is optionally run by the main controller. Thus, the system preferably stabilizes the magnetic field in the synchrotron rather than stabilizing the current applied to the magnets. Stabilization of the magnetic field allows the synchrotron to come to a new energy level quickly. This allows the system to be controlled to an operator or algorithm selected energy level with each pulse of the synchrotron and/or with each breath of the patient.

The winding and/or correction coils correct one, two, three, or four turning magnets, and preferably correct a magnetic field generated by two turning magnets. Optionally, a correction coil 1640 winds a single magnet section 1010 or a correction coil 1620 winds two or more magnet turning sections 1010, 1020. A winding or correction coil covering multiple magnets reduces space between magnets as fewer winding or correction coil ends are required, which occupy space. Reduction of space between turning magnets allows operation of the turning magnets with smaller power supplies and optionally without quadrupole magnet focusing sections.

Space 1160 at the end of a turning magnets 1010, 1040 is optionally further reduced by changing the cross-sectional shape of the winding coils. For example, when the winding coils are running longitudinally along the length of the circulating path or along the length of the turning magnet, the cross-sectional dimension is thick and when the winding coils turn at the end of a turning magnet to run axially across the winding coil, then the cross-sectional area of the winding coils is preferably thin. For example, the cross-sectional area of winding coils as measured by an m×n matrix is 3×2 running longitudinally along the turning magnet and 6×1 running axially at the end of the turning magnet, thereby reducing the width of the coils, n, while keeping the number of coils constant. Preferably, the turn from the longitudinal to axial direction of the winding coil approximates ninety degrees by cutting each winding and welding each longitudinal section to the connecting axial section at about a ninety degree angle. The nearly perpendicular weld further reduces space requirements of the turn in the winding coil, which reduces space in circulating orbit not experiencing focusing and turning forces, which reduces the size of the synchrotron.

Still referring to FIG. 16 and now additionally referring to FIG. 2, FIG. 9, and FIG. 10, an optional modular magnet system is described. As illustrated in FIG. 2, the synchrotron 130 optionally uses sixteen main bending magnets 250. As illustrated in FIG. 9 and FIG. 10, in one case, the sixteen main bending magnets are organized into four beam turning sections 920, where each of the four beam turning sections, as described supra, contain a group of four turning magnets 1010, 1020, 1030, 1040. Now referring to FIG. 16, the winding coil 1630 is illustrated as optionally connecting a sub-group of two turning magnets 1010, 1020. The sub-group of two turning magnets optionally uses a common winding coil for the two turning magnets. The sub-group using a common coil for two magnets is optionally repeated twice in one turning section to form four magnets, is repeated eight times in the synchrotron to form eight groups of two magnets, where two sub-groups of two turning magnets are used in each turning section 920, and/or is repeated n times where n is a positive integer. Generally, the sub-group of two magnets wound with a common winding coil is a building block used to build a synchrotron. Having one sub-group of magnets that is used multiple times in the synchrotron reduces manufacturing costs, simplifies quality control and/or quality assurance procedures, and simplifies inspection.

Figure 17A:
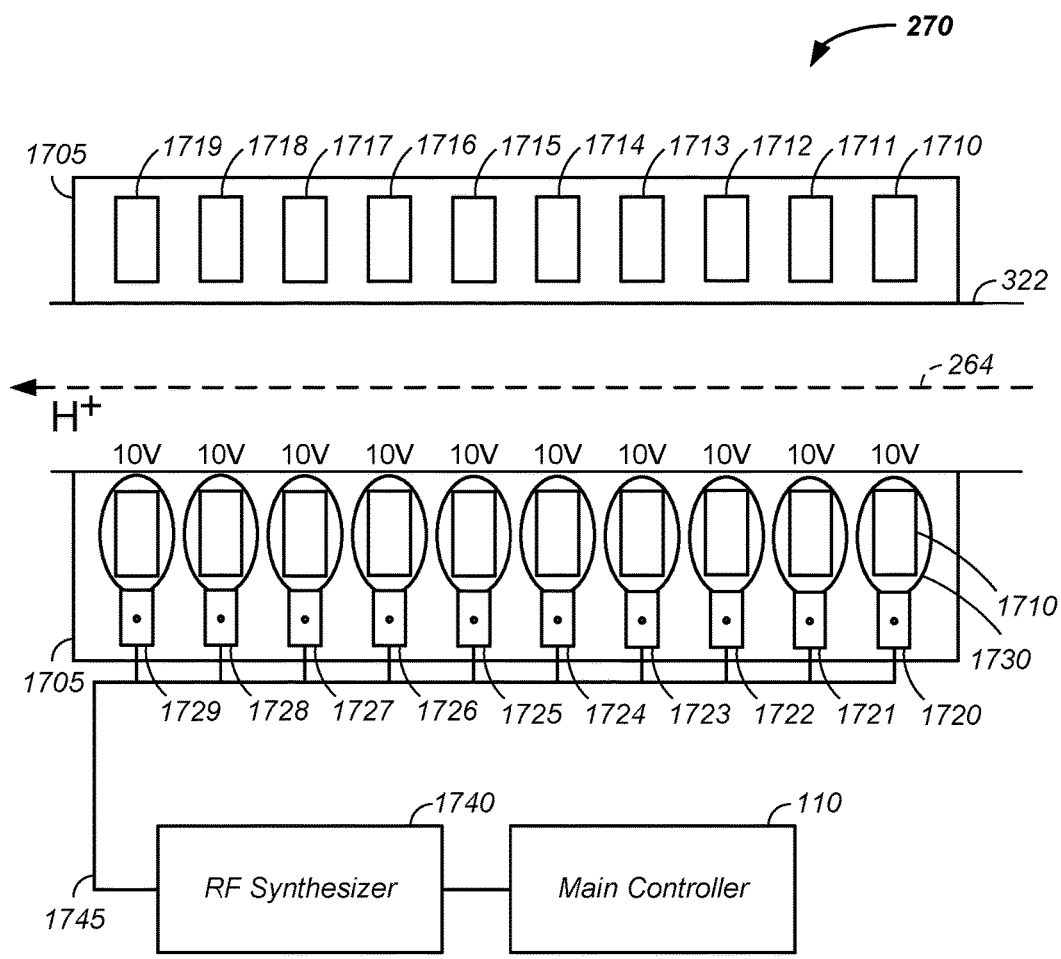
FIG. 17A and FIG. 17B illustrate an RF accelerator and an RF accelerator subsystem, respectively.
Figure 17B:
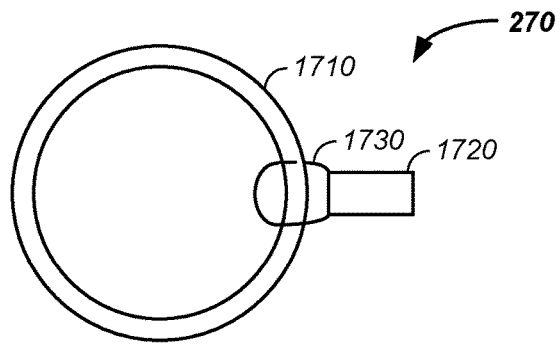

Referring now to FIG. 17A and FIG. 17B, the accelerator system 270, such as a radio-frequency (RF) accelerator system, is further described. The accelerator includes a series of coils 1710-1719, such as iron or ferrite coils, each circumferentially enclosing the vacuum system 320 through which the proton beam 264 passes in the synchrotron 130. Referring now to FIG. 17B, the first coil 1710 is further described. A loop of standard wire 1730 completes at least one turn about the first coil 1710. The loop attaches to a microcircuit 1720.

Referring again to FIG. 17A, an RF synthesizer 1740, which is preferably connected to the main controller 110, provides a low voltage RF signal that is synchronized to the period of circulation of protons in the proton beam path 264. The RF synthesizer 1740, microcircuit 1720, loop 1730, and coil 1710 combine to provide an accelerating voltage to the protons in the proton beam path 264. For example, the RF synthesizer 1740 sends a signal to the microcircuit 1720, which amplifies the low voltage RF signal and yields an acceleration voltage, such as about 10 volts. The actual acceleration voltage for a single microcircuit/loop/coil combination is about five, ten, fifteen, or twenty volts, but is preferably about ten volts. Preferably, the RF-amplifier microcircuit and accelerating coil are integrated.

Still referring to FIG. 17A, the integrated RF-amplifier microcircuit and accelerating coil presented in FIG. 17B is repeated, as illustrated as the set of coils 1711-1719 surrounding the vacuum tube 320. For example, the RF-synthesizer 1740, under main controller 130 direction, sends an RF-signal to the microcircuits 1720-1729 connected to coils 1710-1719, respectively. Each of the microcircuit/loop/coil combinations generates a proton accelerating voltage, such as about ten volts each. Hence, a set of five coil combinations generates about fifty volts for proton acceleration. Preferably about five to twenty microcircuit/loop/coil combinations are used and more preferably about nine or ten microcircuit/loop/coil combinations are used in the accelerator system 270.

As a further clarifying example, the RF synthesizer 1740 sends an RF-signal, with a period equal to a period of circulation of a proton about the synchrotron 130, to a set of ten microcircuit/loop/coil combinations, which results in about 100 volts for acceleration of the protons in the proton beam path 264. The 100 volts is generated at a range of frequencies, such as at about one MHz for a low energy proton beam to about fifteen MHz for a high energy proton beam. The RF-signal is optionally set at an integer multiple of a period of circulation of the proton about the synchrotron circulating path. Each of the microcircuit/loop/coil combinations are optionally independently controlled in terms of acceleration voltage and frequency.

Integration of the RF-amplifier microcircuit and accelerating coil, in each microcircuit/loop/coil combination, results in three considerable advantages. First, for synchrotrons, the prior art does not use microcircuits integrated with the accelerating coils but rather uses a set of long cables to provide power to a corresponding set of coils. The long cables have an impedance/resistance, which is problematic for high frequency RF control. As a result, the prior art system is not operable at high frequencies, such as above about ten MHz. The integrated RF-amplifier microcircuit/ accelerating coil system is operable at above about ten MHz and even fifteen MHz where the impedance and/or resistance of the long cables in the prior art systems results in poor control or failure in proton acceleration. Second, the long cable system, operating at lower frequencies, costs about $50,000 and the integrated microcircuit system costs about $1000, which is fifty times less expensive. Third, the microcircuit/loop/coil combinations in conjunction with the RF-amplifier system results in a compact low power consumption design allowing production and use of a proton cancer therapy system in a small space, as described supra, and in a cost effective manner.

Referring again to FIG. 16, an example of a winding coil 1630 that covers two turning magnets 1010, 1020 is provided. Optionally, a first winding coil 1640 covers two magnets 1010, 1020 and a second winding coil, not illustrated, covers another two magnets 1030, 1040. As described, supra, this system reduces space between turning section allowing more magnetic field to be applied per radian of turn. A first correction coil 1640 is illustrated that is used to correct the magnetic field for the first turning magnet 1010. A second correction coil 1620 is illustrated that is used to correct the magnetic field for a winding coil 1630 about two turning magnets. Individual correction coils for each turning magnet are preferred and individual correction coils yield the most precise and/or accurate magnetic field in each turning section. Particularly, an individual correction coil is preferably used to compensate for imperfections in the individual magnet of a given turning section. Hence, with a series of magnetic field sensors, corresponding magnetic fields are individually adjustable in a series of feedback loops, via a magnetic field monitoring system, as an independent coil is used for each turning section. Alternatively, a multiple magnet correction coil is used to correct the magnetic field for a plurality of turning section magnets.

Proton Beam Extraction

Figure 18:
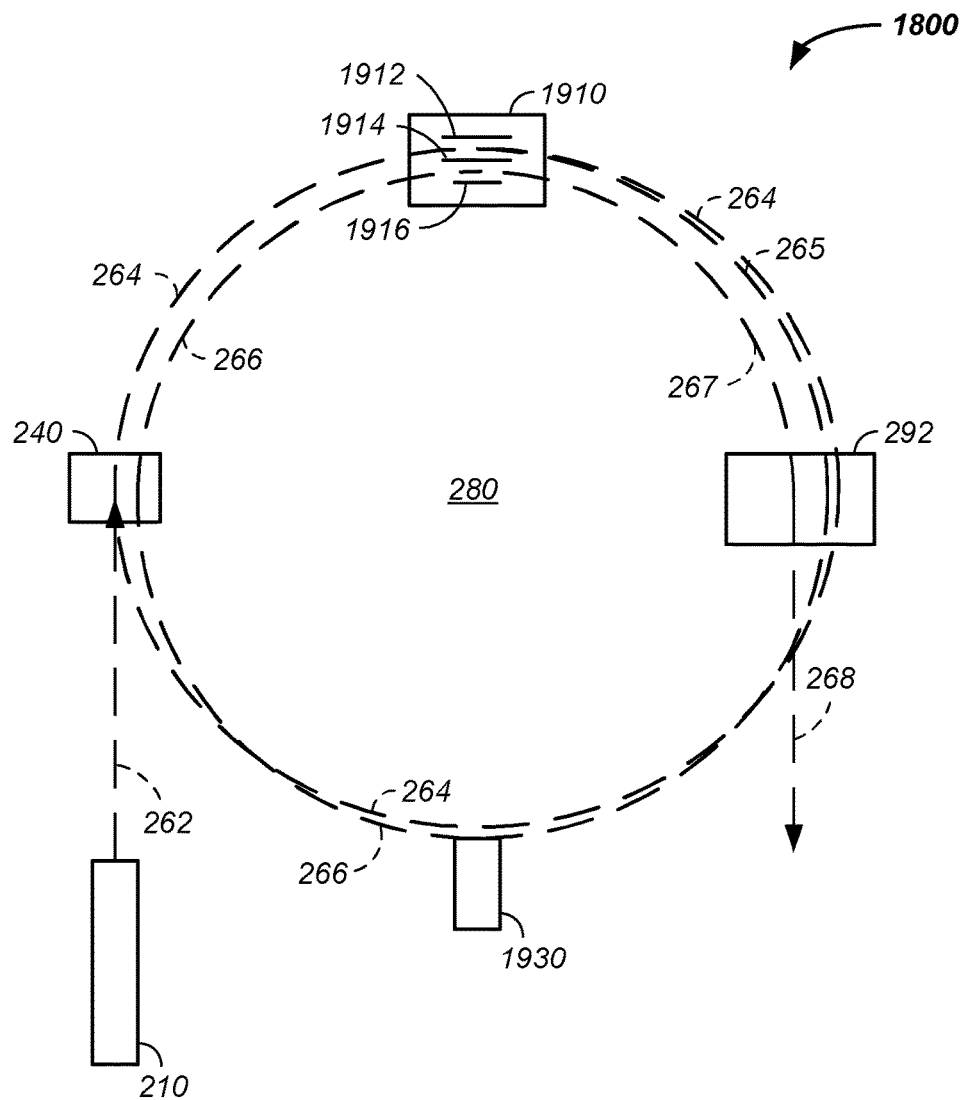
FIG. 18 illustrates a charged particle extraction system.

Referring now to FIG. 18, an exemplary proton beam extraction process 1800 from the synchrotron 130 is illustrated. For clarity, FIG. 18 removes elements represented in FIG. 2, such as the turning magnets, which allows for greater clarity of presentation of the proton beam path as a function of time. Generally, protons are extracted from the synchrotron 130 by slowing the protons. As described, supra, the protons were initially accelerated in a circulating path 264, which is maintained with a plurality of main bending magnets 250. The circulating path is referred to herein as an original central beamline 264. The protons repeatedly cycle around a central point in the synchrotron 280. The proton path traverses through a radio frequency (RF) cavity system 1910. To initiate extraction, an RF field is applied across a first blade 1912 and a second blade 1914, in the RF cavity system 1910. The first blade 1912 and second blade 1914 are referred to herein as a first pair of blades.

In the proton extraction process, an RF voltage is applied across the first pair of blades, where the first blade 1912 of the first pair of blades is on one side of the circulating proton beam path 264 and the second blade 1914 of the first pair of blades is on an opposite side of the circulating proton beam path 264. The applied RF field applies energy to the circulating charged-particle beam. The applied RF field alters the orbiting or circulating beam path slightly of the protons from the original central beamline 264 to an altered circulating beam path 265. Upon a second pass of the protons through the RF cavity system, the RF field further moves the protons off of the original proton beamline 264. For example, if the original beamline is considered as a circular path, then the altered beamline is slightly elliptical. The applied RF field is timed to apply outward or inward movement to a given band of protons circulating in the synchrotron accelerator. Each orbit of the protons is slightly more off axis compared to the original circulating beam path 264. Successive passes of the protons through the RF cavity system are forced further and further from the original central beamline 264 by altering the direction and/or intensity of the RF field with each successive pass of the proton beam through the RF field.

The RF voltage is frequency modulated at a frequency about equal to the period of one proton cycling around the synchrotron for one revolution or at a frequency than is an integral multiplier of the period of one proton cycling about the synchrotron. The applied RF frequency modulated voltage excites a betatron oscillation. For example, the oscillation is a sine wave motion of the protons. The process of timing the RF field to a given proton beam within the RF cavity system is repeated thousands of times with each successive pass of the protons being moved approximately one micrometer further off of the original central beamline 264. For clarity, the approximately 1000 changing beam paths with each successive path of a given band of protons through the RF field are illustrated as the altered beam path 265.

With a sufficient sine wave betatron amplitude, the altered circulating beam path 265 touches and/or traverses a material 1930, such as a foil or a sheet of foil. The foil is preferably a lightweight material, such as beryllium, a lithium hydride, a carbon sheet, or a material having low nuclear charge components. Herein, a material of low nuclear charge is a material composed of atoms consisting essentially of atoms having six or fewer protons. The foil is preferably about 10 to 150 microns thick, is more preferably about 30 to 100 microns thick, and is still more preferably about 40 to 60 microns thick. In one example, the foil is beryllium with a thickness of about 50 microns. When the protons traverse through the foil, energy of the protons is lost and the speed of the protons is reduced. Typically, a current is also generated, described infra. Protons moving at a slower speed travel in the synchrotron with a reduced radius of curvature 266 compared to either the original central beamline 264 or the altered circulating path 265. The reduced radius of curvature 266 path is also referred to herein as a path having a smaller diameter of trajectory or a path having protons with reduced energy. The reduced radius of curvature 266 is typically about two millimeters less than a radius of curvature of the last pass of the protons along the altered proton beam path 265.

The thickness of the material 1930 is optionally adjusted to created a change in the radius of curvature, such as about ½, 1, 2, 3, or 4 mm less than the last pass of the protons 265 or original radius of curvature 264. Protons moving with the smaller radius of curvature travel between a second pair of blades. In one case, the second pair of blades is physically distinct and/or is separated from the first pair of blades. In a second case, one of the first pair of blades is also a member of the second pair of blades. For example, the second pair of blades is the second blade 1914 and a third blade 1916 in the RF cavity system 1910. A high voltage DC signal, such as about 1 to 5 kV, is then applied across the second pair of blades, which directs the protons out of the synchrotron through an extraction magnet 292, such as a Lamberson extraction magnet, into a transport path 268.

Control of acceleration of the charged particle beam path in the synchrotron with the accelerator and/or applied fields of the turning magnets in combination with the above described extraction system allows for control of the intensity of the extracted proton beam, where intensity is a proton flux per unit time or the number of protons extracted as a function of time. For example, when a current is measured beyond a threshold, the RF field modulation in the RF cavity system is terminated or reinitiated to establish a subsequent cycle of proton beam extraction. This process is repeated to yield many cycles of proton beam extraction from the synchrotron accelerator.

In another embodiment, instead of moving the charged particles to the material 1930, the material 1930 is mechanically moved to the circulating charged particles. Particularly, the material 1930 is mechanically or electromechanically translated into the path of the circulating charged particles to induce the extraction process, described supra.

In either case, because the extraction system does not depend on any change in magnetic field properties, it allows the synchrotron to continue to operate in acceleration or deceleration mode during the extraction process. Stated differently, the extraction process does not interfere with synchrotron acceleration. In stark contrast, traditional extraction systems introduce a new magnetic field, such as via a hexapole, during the extraction process. More particularly, traditional synchrotrons have a magnet, such as a hexapole magnet, that is off during an acceleration stage. During the extraction phase, the hexapole magnetic field is introduced to the circulating path of the synchrotron. The introduction of the magnetic field necessitates two distinct modes, an acceleration mode and an extraction mode, which are mutually exclusive in time. The herein described system allows for acceleration and/or deceleration of the proton during the extraction step without the use of a newly introduced magnetic field, such as by a hexapole magnet.

Charged Particle Beam Intensity Control

Control of applied field, such as a radio-frequency (RF) field, frequency and magnitude in the RF cavity system 1910 allows for intensity control of the extracted proton beam, where intensity is extracted proton flux per unit time or the number of protons extracted as a function of time.

Figure 19:
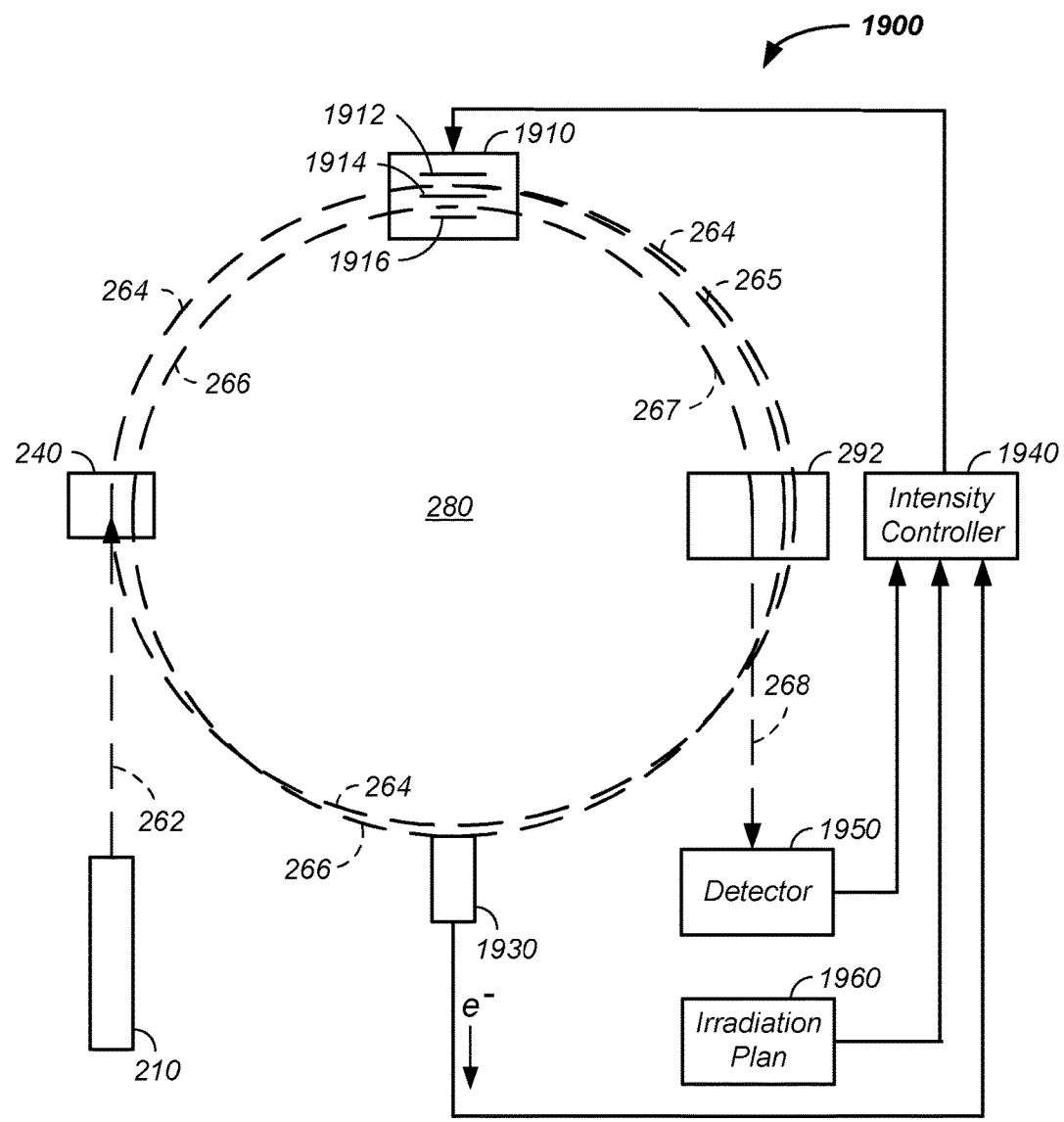
FIG. 19 illustrates a charged particle extraction and intensity control system.

Referring now to FIG. 19, an intensity control system 1900 is illustrated. In this example, an intensity control feedback loop is added to the extraction system, described supra. When protons in the proton beam hit the material 1930 electrons are given off resulting in a current. The resulting current is converted to a voltage and is used as part of a ion beam intensity monitoring system or as part of an ion beam feedback loop for controlling beam intensity. The voltage is optionally measured and sent to the main controller 110 or to an intensity controller subsystem 1940, which is preferably in communication or under the direction of the main controller 110. More particularly, when protons in the charged particle beam path pass through the material 1930, some of the protons lose a small fraction of their energy, such as about one-tenth of a percent, which results in a secondary electron. That is, protons in the charged particle beam push some electrons when passing through material 1930 giving the electrons enough energy to cause secondary emission. The resulting electron flow results in a current or signal that is proportional to the number of protons going through the target material 1930. The resulting current is preferably converted to voltage and amplified. The resulting signal is referred to as a measured intensity signal.

The amplified signal or measured intensity signal resulting from the protons passing through the material 1930 is optionally used in monitoring the intensity of the extracted protons and is preferably used in controlling the intensity of the extracted protons. For example, the measured intensity signal is compared to a goal signal, which is predetermined in an irradiation of the tumor plan. The difference between the measured intensity signal and the planned for goal signal is calculated. The difference is used as a control to the RF generator. Hence, the measured flow of current resulting from the protons passing through the material 1930 is used as a control in the RF generator to increase or decrease the number of protons undergoing betatron oscillation and striking the material 1930. Hence, the voltage determined off of the material 1930 is used as a measure of the orbital path and is used as a feedback control to control the RF cavity system.

In one example, the intensity controller subsystem 1940 preferably additionally receives input from: (1) a detector 1950, which provides a reading of the actual intensity of the proton beam and (2) an irradiation plan 1960. The irradiation plan provides the desired intensity of the proton beam for each x, y, energy, and/or rotational position of the patient/tumor as a function of time. Thus, the intensity controller 1940 receives the desired intensity from the irradiation plan 1950, the actual intensity from the detector 1950 and/or a measure of intensity from the material 1930, and adjusts the radio-frequency field in the RF cavity system 1910 to yield an intensity of the proton beam that matches the desired intensity from the irradiation plan 1960.

As described, supra, the photons striking the material 1930 is a step in the extraction of the protons from the synchrotron 130. Hence, the measured intensity signal is used to change the number of protons per unit time being extracted, which is referred to as intensity of the proton beam. The intensity of the proton beam is thus under algorithm control. Further, the intensity of the proton beam is controlled separately from the velocity of the protons in the synchrotron 130. Hence, intensity of the protons extracted and the energy of the protons extracted are independently variable.

For example, protons initially move at an equilibrium trajectory in the synchrotron 130. An RF field is used to excite the protons into a betatron oscillation. In one case, the frequency of the protons orbit is about 10 MHz. In one example, in about one millisecond or after about 10,000 orbits, the first protons hit an outer edge of the target material 130. The specific frequency is dependent upon the period of the orbit. Upon hitting the material 130, the protons push electrons through the foil to produce a current. The current is converted to voltage and amplified to yield a measured intensity signal. The measured intensity signal is used as a feedback input to control the applied RF magnitude, RF frequency, or RF field. Preferably, the measured intensity signal is compared to a target signal and a measure of the difference between the measured intensity signal and target signal is used to adjust the applied RF field in the RF cavity system 1910 in the extraction system to control the intensity of the protons in the extraction step. Stated again, the signal resulting from the protons striking and/or passing through the material 130 is used as an input in RF field modulation. An increase in the magnitude of the RF modulation results in protons hitting the foil or material 130 sooner. By increasing the RF, more protons are pushed into the foil, which results in an increased intensity, or more protons per unit time, of protons extracted from the synchrotron 130.

In another example, a detector 1950 external to the synchrotron 130 is used to determine the flux of protons extracted from the synchrotron and a signal from the external detector is used to alter the RF field or RF modulation in the RF cavity system 1910. Here the external detector generates an external signal, which is used in a manner similar to the measured intensity signal, described in the preceding paragraphs. Preferably, an algorithm or irradiation plan 1960 is used as an input to the intensity controller 1940, which controls the RF field modulation by directing the RF signal in the betatron oscillation generation in the RF cavity system 1910. The irradiation plan 1960 preferably includes the desired intensity of the charged particle beam as a function of time, energy of the charged particle beam as a function of time, for each patient rotation position, and/or for each x-, y-position of the charged particle beam.

In yet another example, when a current from material 130 resulting from protons passing through or hitting material is measured beyond a threshold, the RF field modulation in the RF cavity system is terminated or reinitiated to establish a subsequent cycle of proton beam extraction. This process is repeated to yield many cycles of proton beam extraction from the synchrotron accelerator.

In still yet another embodiment, intensity modulation of the extracted proton beam is controlled by the main controller 110. The main controller 110 optionally and/or additionally controls timing of extraction of the charged particle beam and energy of the extracted proton beam.

The benefits of the system include a multi-dimensional scanning system. Particularly, the system allows independence in: (1) energy of the protons extracted and (2) intensity of the protons extracted. That is, energy of the protons extracted is controlled by an energy control system and an intensity control system controls the intensity of the extracted protons. The energy control system and intensity control system are optionally independently controlled. Preferably, the main controller 110 controls the energy control system and the main controller 110 simultaneously controls the intensity control system to yield an extracted proton beam with controlled energy and controlled intensity where the controlled energy and controlled intensity are independently variable. Thus the irradiation spot hitting the tumor is under independent control of:

time;
  energy;
  intensity;
  x-axis position, where the x-axis represents horizontal movement of the proton beam relative to the patient, and
  y-axis position, where the y-axis represents vertical movement of the proton beam relative to the patient.

In addition, the patient is optionally independently translated and/or rotated relative to a translational axis of the proton beam at the same time.

Figure 20A:
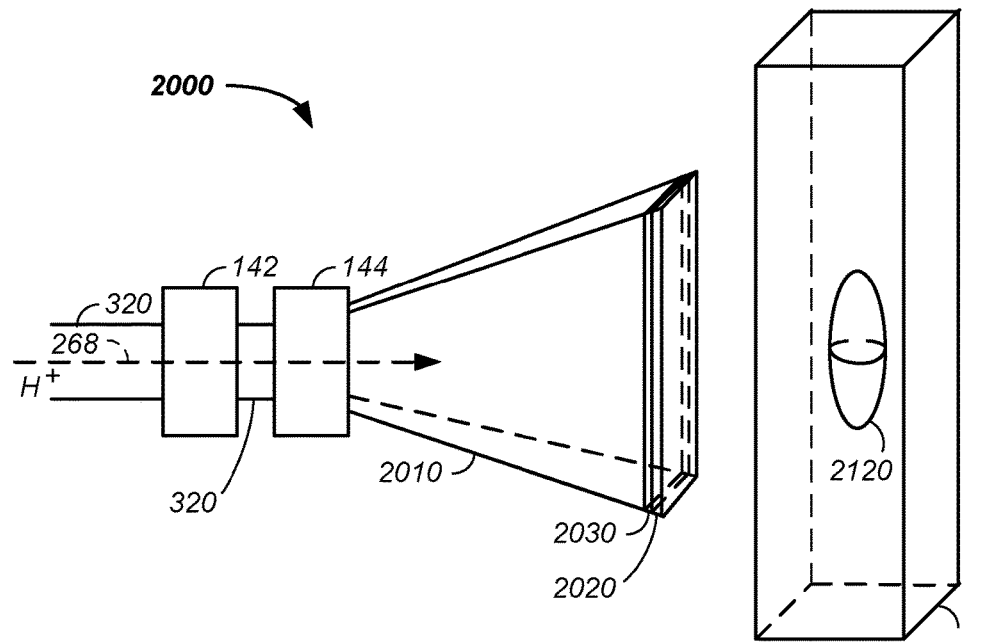
FIG. 20A and FIG. 20B illustrate proton beam position verification systems.
Figure 20B:
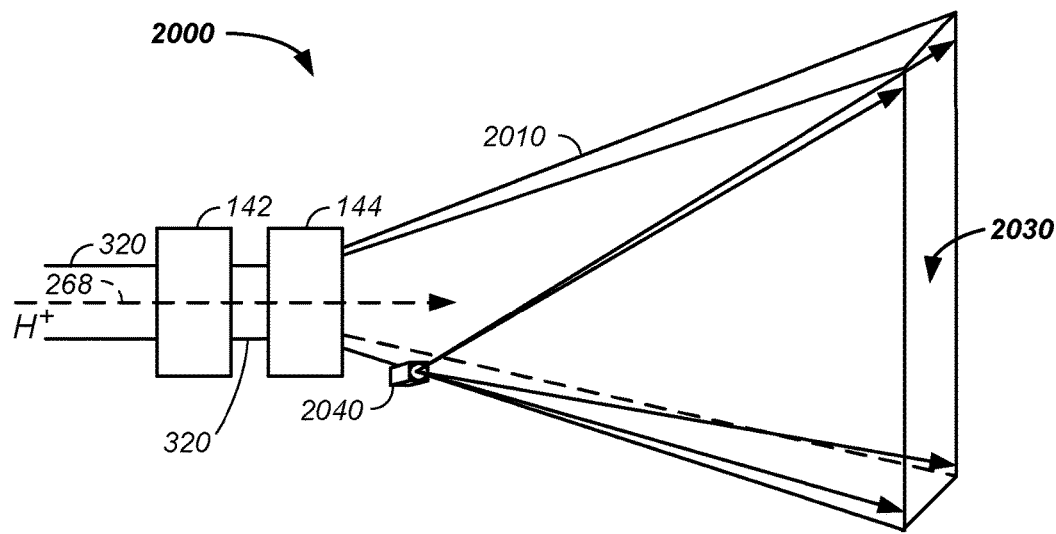

Referring now to FIG. 20A and FIG. 20B, a proton beam position verification system 2000 is described. A nozzle 2010 provides an outlet for the second reduced pressure vacuum system initiating at the foil 395 of the tandem accelerator 390 and running through the synchrotron 130 to a nozzle foil 2020 covering the end of the nozzle 2010. The nozzle expands in x-, y-cross-sectional area along the z-axis of the proton beam path 268 to allow the proton beam 268 to be scanned along the x- and y-axes by the vertical control element 142 and horizontal control element 144, respectively. The nozzle foil 2020 is preferably mechanically supported by the outer edges of an exit port of the nozzle 2010. An example of a nozzle foil 2020 is a sheet of about 0.1 inch thick aluminum foil. Generally, the nozzle foil separates atmosphere pressures on the patient side of the nozzle foil 2020 from the low pressure region, such as about $10^{-5}$ to $10^{-7}$ torr region, on the synchrotron 130 side of the nozzle foil 2020. The low pressure region is maintained to reduce scattering of the proton beam 264, 268.

Still referring to FIG. 20A and FIG. 20B, the proton beam verification system 2000 is a system that allows for monitoring of the actual proton beam position 268, 269 in real-time without destruction of the proton beam. The proton beam verification system 2000 preferably includes a proton beam position verification layer 2030, which is also referred to herein as a coating, luminescent, fluorescent, phosphorescent, radiance, or viewing layer. The verification layer or coating layer 2030 is preferably a coating or thin layer substantially in contact with an inside surface of the nozzle foil 2020, where the inside surface is on the synchrotron side of the nozzle foil 2020. Less preferably, the verification layer or coating layer 2030 is substantially in contact with an outer surface of the nozzle foil 2020, where the outer surface is on the patient treatment side of the nozzle foil 2020. Preferably, the nozzle foil 2020 provides a substrate surface for coating by the coating layer. Optionally, a binding layer is located between the coating layer 2030 and the nozzle foil 2020. Optionally a separate coating layer support element, on which the coating 2030 is mounted, is placed anywhere in the proton beam path 268.

Referring now to FIG. 20B, the coating 2030 yields a measurable spectroscopic response, spatially viewable by the detector 2040, as a result of transmission by the proton beam 268. The coating 2030 is preferably a phosphor, but is optionally any material that is viewable or imaged by a detector where the material changes spectroscopically as a result of the proton beam path 268 hitting or transmitting through the coating 2030. A detector or camera 2040 views the coating layer 2030 and determines the current position of the proton beam 269 by the spectroscopic differences resulting from protons passing through the coating layer. For example, the camera 2040 views the coating surface 2030 as the proton beam 268 is being scanned by the horizontal 144 and vertical 142 beam position control elements during treatment of the tumor 2120. The camera 2040 views the current position of the proton beam 269 as measured by spectroscopic response. The coating layer 2030 is preferably a phosphor or luminescent material that glows or emits photons for a short period of time, such as less than 5 seconds for a 50% intensity, as a result of excitation by the proton beam 268. Optionally, a plurality of cameras or detectors 2040 are used, where each detector views all or a portion of the coating layer 2030. For example, two detectors 2040 are used where a first detector views a first half of the coating layer and the second detector views a second half of the coating layer. Preferably, at least a portion of the detector 2040 is mounted into the nozzle 2010 to view the proton beam position after passing through the first axis and second axis controllers 142, 144. Preferably, the coating layer 2030 is positioned in the proton beam path 268 in a position prior to the protons striking the patient 2130.

Still referring to FIG. 20B, the main controller 130, connected to the camera or detector 2040 output, compares the actual proton beam position 269 with the planned proton beam position and/or a calibration reference to determine if the actual proton beam position 269 is within tolerance. The proton beam verification system 2000 preferably is used in at least two phases, a calibration phase and a proton beam treatment phase. The calibration phase is used to correlate, as a function of x-, y-position of the glowing response the actual x-, y-position of the proton beam at the patient interface. During the proton beam treatment phase, the proton beam position is monitored and compared to the calibration and/or treatment plan to verify accurate proton delivery to the tumor 2120 and/or as a proton beam shutoff safety indicator.

Patient Positioning

Figure 21A:
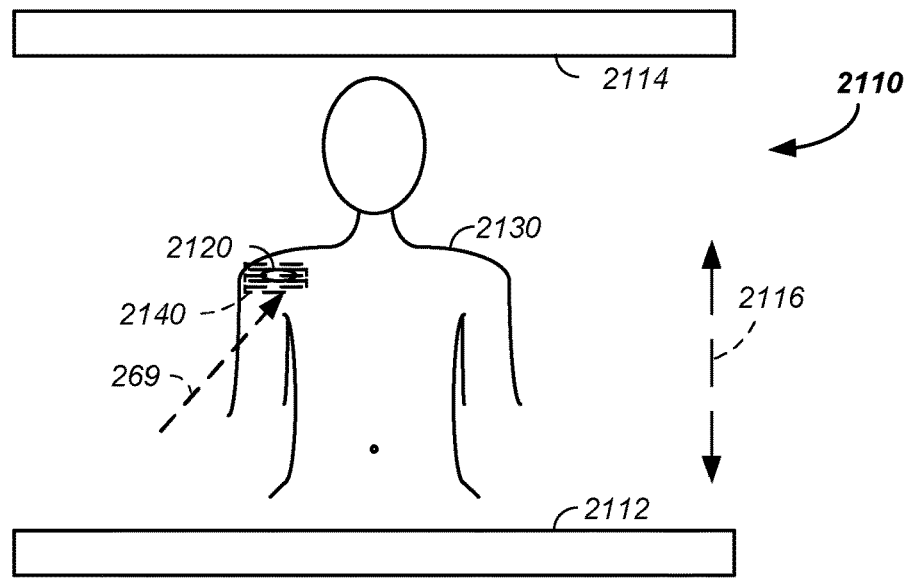
FIG. 21A and FIG. 21B illustrate a patient positioning system from: (A) a front view and (B) a top view, respectively.
Figure 21B:
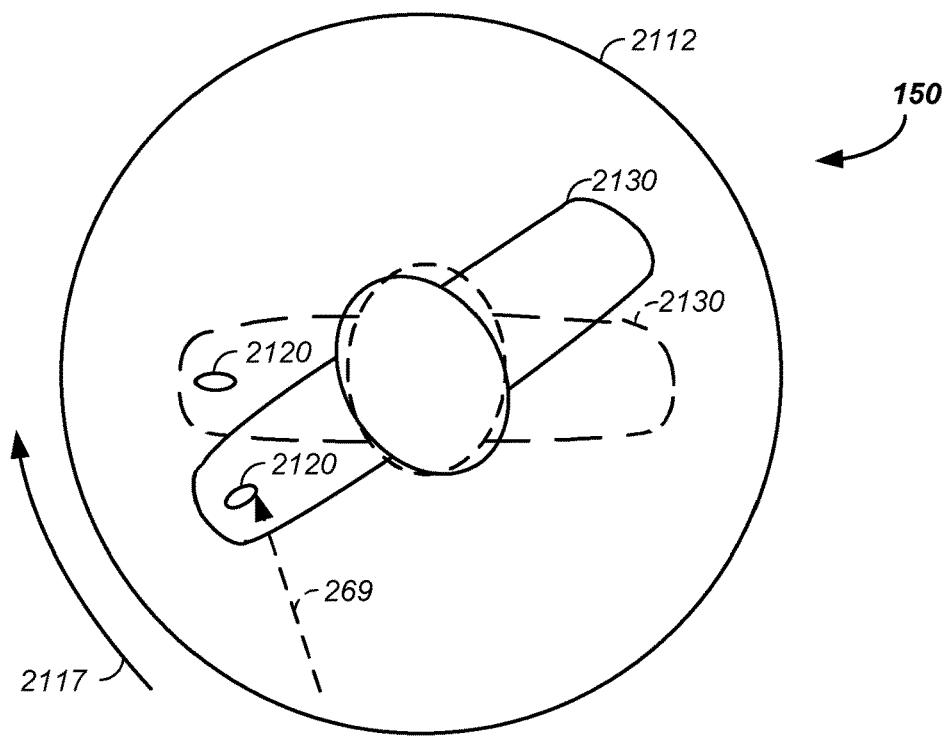

Referring now to FIG. 21A and FIG. 21B, the patient is preferably positioned on or within a patient translation and rotation positioning system 2110 of the patient interface module 150. The patient translation and rotation positioning system 2110 is used to translate the patient and/or rotate the patient into a zone where the proton beam can scan the tumor using a scanning system 140 or proton targeting system, described infra. Essentially, the patient positioning system 2110 performs large movements of the patient to place the tumor near the center of a proton beam path 268 and the proton scanning or targeting system 140 performs fine movements of the momentary beam position 269 in targeting the tumor 2120. To illustrate, FIG. 21A shows the momentary proton beam position 269 and a range of scannable positions 2140 using the proton scanning or targeting system 140, where the scannable positions 2140 are about the tumor 2120 of the patient 2130. In this example, the scannable positions are scanned along the x- and y-axes; however, scanning is optionally simultaneously performed along the z-axis as described infra. This illustratively shows that the y-axis movement of the patient occurs on a scale of the body, such as adjustment of about 1, 2, 3, or 4 feet, while the scannable region of the proton beam 268 covers a portion of the body, such as a region of about 1, 2, 4, 6, 8, 10, or 12 inches. The patient positioning system and its rotation and/or translation of the patient combines with the proton targeting system to yield precise and/or accurate delivery of the protons to the tumor.

Referring still to FIG. 21A and FIG. 21B, the patient positioning system 2110 optionally includes a bottom unit 2112 and a top unit 2114, such as discs or a platform. Referring now to FIG. 21A, the patient positioning unit 2110 is preferably y-axis adjustable 2116 to allow vertical shifting of the patient relative to the proton therapy beam 268. Preferably, the vertical motion of the patient positioning unit 2110 is about 10, 20, 30, or 50 centimeters per minute. Referring now to FIG. 21B, the patient positioning unit 2110 is also preferably rotatable 2117 about a rotation axis, such as about the y-axis running through the center of the bottom unit 2112 or about a y-axis running through the tumor 2120, to allow rotational control and positioning of the patient relative to the proton beam path 268. Preferably the rotational motion of the patient positioning unit 2110 is about 360 degrees per minute. Optionally, the patient positioning unit rotates about 45, 90, or 180 degrees. Optionally, the patient positioning unit 2110 rotates at a rate of about 45, 90, 180, 360, 720, or 1080 degrees per minute. The rotation of the positioning unit 2117 is illustrated about the rotation axis at two distinct times, $t_1$ and $t_2$. Protons are optionally delivered to the tumor 2120 at n times where each of the n times represent a different relative direction of the incident proton beam 269 hitting the patient 2130 due to rotation of the patient 2117 about the rotation axis.

Any of the semi-vertical, sitting, or laying patient positioning embodiments described, infra, are optionally vertically translatable along the y-axis or rotatable about the rotation or y-axis.

Preferably, the top and bottom units 2112, 2114 move together, such that they rotate at the same rates and translate in position at the same rates. Optionally, the top and bottom units 2112, 2114 are independently adjustable along the y-axis to allow a difference in distance between the top and bottom units 2112, 2114. Motors, power supplies, and mechanical assemblies for moving the top and bottom units 2112, 2114 are preferably located out of the proton beam path 269, such as below the bottom unit 2112 and/or above the top unit 2114. This is preferable as the patient positioning unit 2110 is preferably rotatable about 360 degrees and the motors, power supplies, and mechanical assemblies interfere with the protons if positioned in the proton beam path 269.

Proton Delivery Efficiency

Figure 22:
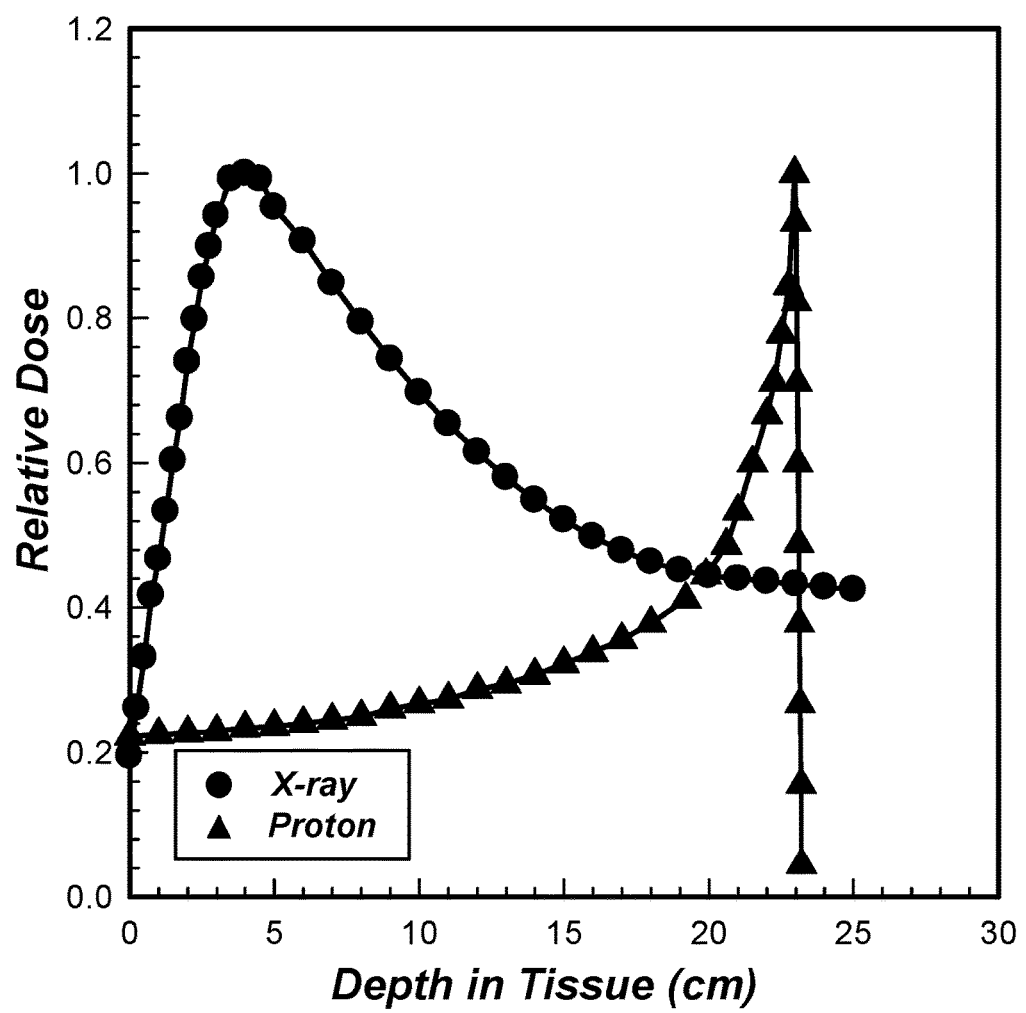
FIG. 22 provides X-ray and proton beam dose distributions.
Figure 23A:
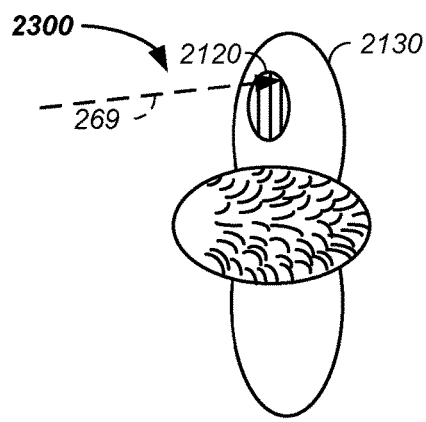
FIGS. 23(A-E) illustrate controlled scanning and depth of focus irradiation.
Figure 23B:
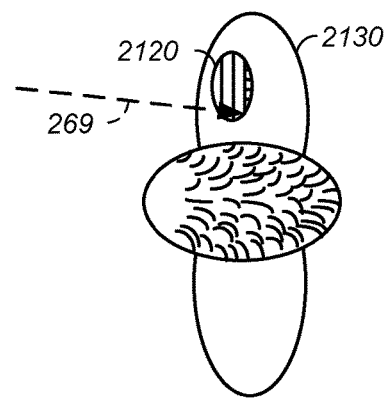
Figure 23C:
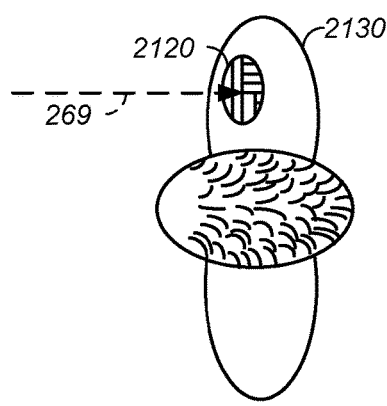
Figure 23D:
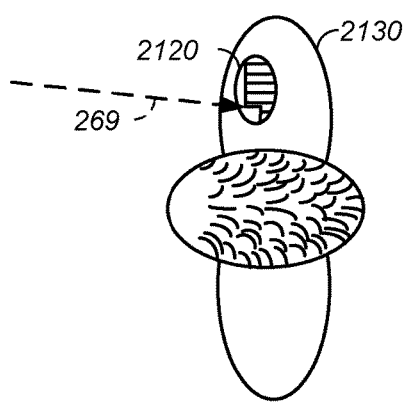
Figure 23E:
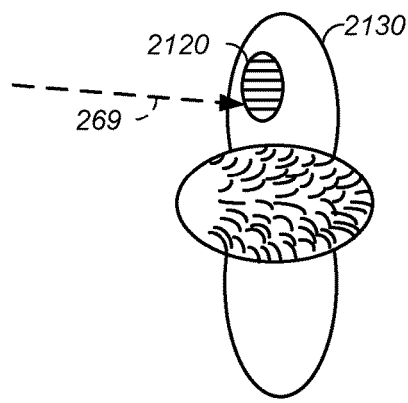
Figure 24A:
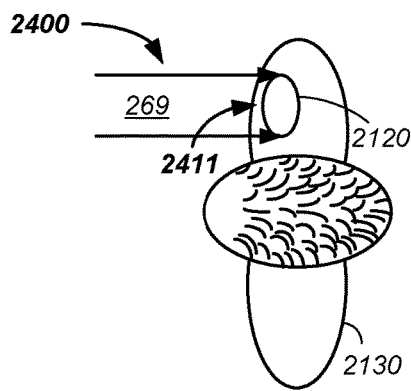
FIGS. 24(A-E) illustrate multi-field irradiation.
Figure 24B:
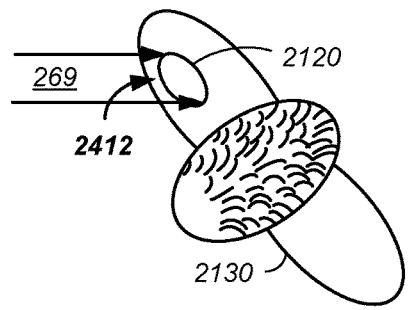
Figure 24C:
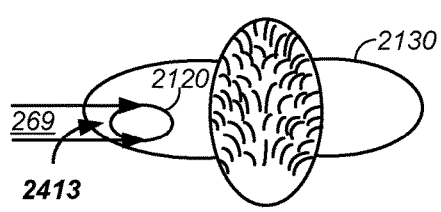
Figure 24D:
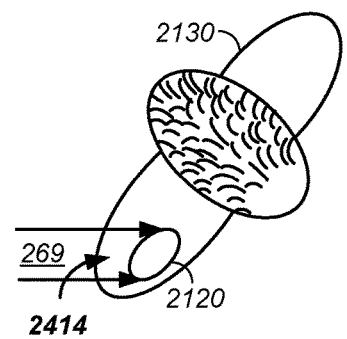
Figure 24E:
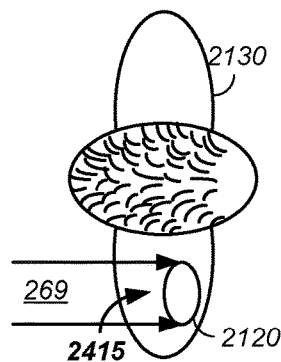

Referring now to FIG. 22, a common distribution of relative doses for both X-rays and proton irradiation is presented. As shown, X-rays deposit their highest dose near the surface of the targeted tissue and then deposited doses exponentially decrease as a function of tissue depth. The deposition of X-ray energy near the surface is non-ideal for tumors located deep within the body, which is usually the case, as excessive damage is done to the soft tissue layers surrounding the tumor 2120. The advantage of protons is that they deposit most of their energy near the end of the flight trajectory as the energy loss per unit path of the absorber transversed by a proton increases with decreasing particle velocity, giving rise to a sharp maximum in ionization near the end of the range, referred to herein as the Bragg peak. Furthermore, since the flight trajectory of the protons is variable by increasing or decreasing the initial kinetic energy or initial velocity of the proton, then the peak corresponding to maximum energy is movable within the tissue. Thus z-axis control of the proton depth of penetration is allowed by the acceleration/extraction process, described supra. As a result of proton dose-distribution characteristics, using the algorithm described, infra, a radiation oncologist can optimize dosage to the tumor 2120 while minimizing dosage to surrounding normal tissues.

Herein, the term ingress refers to a place charged particles enter into the patient 2130 or a place of charged particles entering the tumor 2120. The ingress region of the Bragg energy profile refers to the relatively flat dose delivery portion at shallow depths of the Bragg energy profile. Similarly, herein the terms proximal or the clause proximal region refer to the shallow depth region of the tissue that receives the relatively flat radiation dose delivery portion of the delivered Bragg profile energy. Herein, the term distal refers to the back portion of the tumor located furthest away from the point of origin where the charged particles enter the tumor. In terms of the Bragg energy profile, the Bragg peak is at the distal point of the profile. Herein, the term ventral refers to the front of the patient and the term dorsal refers to the back of the patient. As an example of use, when delivering protons to a tumor in the body, the protons ingress through the healthy tissue and if delivered to the far side of the tumor, the Bragg peak occurs at the distal side of the tumor. For a case where the proton energy is not sufficient to reach the far side of the tumor, the distal point of the Bragg energy profile is the region of furthest penetration into the tumor.

The Bragg peak energy profile shows that protons deliver their energy across the entire length of the body penetrated by the proton up to a maximum penetration depth. As a result, energy is being delivered, in the proximal portion of the Bragg peak energy profile, to healthy tissue, bone, and other body constituents before the proton beam hits the tumor. It follows that the shorter the pathlength in the body prior to the tumor, the higher the efficiency of proton delivery efficiency, where proton delivery efficiency is a measure of how much energy is delivered to the tumor relative to healthy portions of the patient. Examples of proton delivery efficiency include: (1) a ratio of proton energy delivered to the tumor over proton energy delivered to non-tumor tissue; (2) pathlength of protons in the tumor versus pathlength in the non-tumor tissue; and/or (3) damage to a tumor compared to damage to healthy body parts. Any of these measures are optionally weighted by damage to sensitive tissue, such as a nervous system element, heart, brain, or other organ. To illustrate, for a patient in a laying position where the patient is rotated about the y-axis during treatment, a tumor near the heart would at times be treated with protons running through the head-to-heart path, leg-to-heart path, or hip-to-heart path, which are all inefficient compared to a patient in a sitting or semi-vertical position where the protons are all delivered through a shorter chest-to-heart; side-of-body-to-heart, or back-to-heart path. Particularly, compared to a laying position, using a sitting or semi-vertical position of the patient, a shorter pathlength through the body to a tumor is provided to a tumor located in the torso or head, which results in a higher or better proton delivery efficiency.

Herein proton delivery efficiency is separately described from time efficiency or synchrotron use efficiency, which is a fraction of time that the charged particle beam apparatus is in a tumor treating operation mode.

Depth Targeting

Referring now to FIGS. 23(A-E), x-axis scanning of the proton beam is illustrated while z-axis energy of the proton beam undergoes controlled variation 2300 to allow irradiation of slices of the tumor 2120. For clarity of presentation, the simultaneous y-axis scanning that is performed is not illustrated. In FIG. 23A, irradiation is commencing with the momentary proton beam position 269 at the start of a first slice. Referring now to FIG. 23B, the momentary proton beam position is at the end of the first slice. Importantly, during a given slice of irradiation, the proton beam energy is preferably continuously controlled and changed according to the tissue mass and density in front of the tumor 2120. The variation of the proton beam energy to account for tissue density thus allows the beam stopping point, or Bragg peak, to remain inside the tissue slice. The variation of the proton beam energy during scanning or during x-, y-axes scanning is possible due to the acceleration/extraction techniques, described supra, which allow for acceleration of the proton beam during extraction. FIG. 23C, FIG. 23D, and FIG. 23E show the momentary proton beam position in the middle of the second slice, two-thirds of the way through a third slice, and after finalizing irradiation from a given direction, respectively. Using this approach, controlled, accurate, and precise delivery of proton irradiation energy to the tumor 2120, to a designated tumor subsection, or to a tumor layer is achieved. Efficiency of deposition of proton energy to tumor, as defined as the ratio of the proton irradiation energy delivered to the tumor relative to the proton irradiation energy delivered to the healthy tissue is further described infra.

Multi-Field Irradiation

It is desirable to maximize efficiency of deposition of protons to the tumor 2120, as defined by maximizing the ratio of the proton irradiation energy delivered to the tumor 2120 relative to the proton irradiation energy delivered to the healthy tissue. Irradiation from one, two, or three directions into the body, such as by rotating the body about 90 degrees between irradiation sub-sessions results in proton irradiation from the proximal portion of the Bragg peak concentrating into one, two, or three healthy tissue volumes, respectively. It is desirable to further distribute the proximal portion of the Bragg peak energy evenly through the healthy volume tissue surrounding the tumor 2120.

Multi-field irradiation is proton beam irradiation from a plurality of entry points into the body. For example, the patient 2130 is rotated and the radiation source point is held constant. For example, the patient 2130 is rotated through 360 degrees and proton therapy is applied from a multitude of angles resulting in the ingress or proximal radiation being circumferentially spread about the tumor yielding enhanced proton irradiation efficiency. In one case, the body is rotated into greater than 3, 5, 10, 15, 20, 25, 30, or 35 positions and proton irradiation occurs with each rotation position. Rotation of the patient is preferably performed using the patient positioning system 2110 and/or the bottom unit 2112 or disc, described supra. Rotation of the patient 2130 while keeping the delivery proton beam 268 in a relatively fixed orientation allows irradiation of the tumor 2120 from multiple directions without use of a new collimator for each direction. Further, as no new setup is required for each rotation position of the patient 2130, the system allows the tumor 2120 to be treated from multiple directions without reseating or positioning the patient, thereby minimizing tumor 2120 regeneration time, increasing the synchrotrons efficiency, and increasing patient throughput.

The patient is optionally centered on the bottom unit 2112 or the tumor 2120 is optionally centered on the bottom unit 2112. If the patient is centered on the bottom unit 2112, then the first axis control element 142 and second axis control element 144 are programmed to compensate for the off central axis of rotation position variation of the tumor 2120.

Referring now to FIGS. 24(A-E), an example of multi-field irradiation 2400 is presented. In this example, five patient rotation positions are illustrated; however, the five rotation positions are discrete rotation positions of about thirty-six rotation positions, where the body is rotated about ten degrees with each position. Referring now to FIG. 24A, a range of irradiation beam positions 269 is illustrated from a first body rotation position, illustrated as the patient 2130 facing the proton irradiation beam where the tumor receives the bulk of the Bragg profile energy while a first healthy volume 2411 is irradiated by the less intense ingress portion of the Bragg profile energy. Referring now to FIG. 24B, the patient 2130 is rotated about forty degrees and the irradiation is repeated. In the second position, the tumor 2120 again receives the bulk of the irradiation energy and a second healthy tissue volume 2412 receives the smaller ingress portion of the Bragg profile energy. Referring now to FIG. 24C, FIG. 24D, and FIG. 24E, the patient 2130 is rotated a total of about 90, 130, and 180 degrees, respectively. For each of the third, fourth, and fifth rotation positions, the tumor 2120 receives the bulk of the irradiation energy and the third, fourth, and fifth healthy tissue volumes 2413, 2414, 1415 receive the smaller ingress portion of the Bragg peak energy, respectively. Thus, the rotation of the patient during proton therapy results in the proximal or ingress energy of the delivered proton energy to be distributed about the tumor 2120, such as to regions one to five 2411-2415, while along a given axis, at least about 75, 80, 85, 90, or 95 percent of the energy is delivered to the tumor 2120.

For a given rotation position, all or part of the tumor is irradiated. For example, in one embodiment only a distal section or distal slice of the tumor 2120 is irradiated with each rotation position, where the distal section is a section furthest from the entry point of the proton beam into the patient 2130. For example, the distal section is the dorsal side of the tumor when the patient 2130 is facing the proton beam and the distal section is the ventral side of the tumor when the patient 2130 is facing away from the proton beam.

Figure 25:
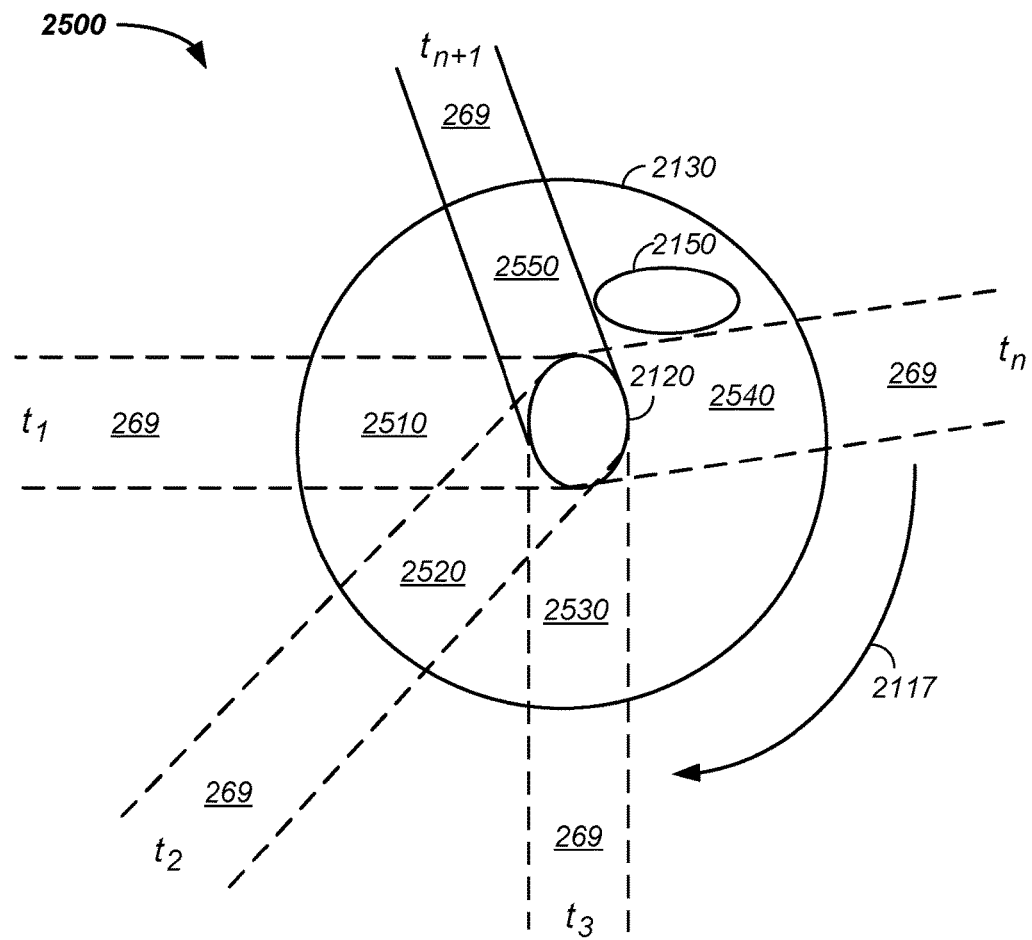
FIG. 25 illustrates dose efficiency enhancement via use of multi-field irradiation.

Referring now to FIG. 25, a second example of multi-field irradiation 2500 is presented where the proton source is stationary and the patient 2130 is rotated. For ease of presentation, the stationary but scanning proton beam path 269 is illustrated as entering the patient 2130 from varying sides at times $t_1, t_2, t_3, \ldots, t_n, t_{n+1}$ as the patient is rotated. At a first time, $t_1$, the ingress side or proximal region of the Bragg peak profile hits a first area, $A_1$. Again, the proximal end of the Bragg peak profile refers to the relatively shallow depths of tissue where Bragg energy profile energy delivery is relatively flat. The patient is rotated and the proton beam path is illustrated at a second time, $t_2$, where the ingress energy of the Bragg energy profile hits a second area, $A_2$. Thus, the low radiation dosage of the ingress region of the Bragg profile energy is delivered to the second area. At a third time, the ingress end of the Bragg energy profile hits a third area, $A_3$. This rotation and irradiation process is repeated n times, where n is a positive number greater than five and preferably greater than about 10, 20, 30, 100, or 300. As illustrated, at an $n^{th}$ time, $t_n$, if the patient 2130 is rotated further, the scanning proton beam 269 would hit a sensitive body constituent 2150, such as the spinal cord or eyes. Irradiation is preferably suspended until the sensitive body constituent is rotated out of the scanning proton beam 269 path. Irradiation is resumed at a time, $t_{n+1}$, after the sensitive body constituent 2150 is rotated out of the proton beam path. In this manner:
 the distal Bragg peak energy is always within the tumor;
 the radiation dose delivery of the distal region of the Bragg energy profile is spread over the tumor;
 the ingress or proximal region of the Bragg energy profile is distributed in healthy tissue about the tumor 2120; and
 sensitive body constituents 2150 receive minimal or no proton beam irradiation.

Proton Delivery Efficiency

Herein, charged particle or proton delivery efficiency is radiation dose delivered to the tumor compared to radiation dose delivered to the healthy regions of the patient.

A proton delivery enhancement method is described where proton delivery efficiency is enhanced, optimized, or maximized. In general, multi-field irradiation is used to deliver protons to the tumor from a multitude of rotational directions. From each direction, the energy of the protons is adjusted to target the distal portion of the tumor, where the distal portion of the tumor is the volume of the tumor furthest from the entry point of the proton beam into the body.

For clarity, the process is described using an example where the outer edges of the tumor are initially irradiated using distally applied radiation through a multitude of rotational positions, such as through 360 degrees. This results in a symbolic or calculated remaining smaller tumor for irradiation. The process is then repeated as many times as necessary on the smaller tumor. However, the presentation is for clarity. In actuality, irradiation from a given rotational angle is performed once with z-axis proton beam energy and intensity being adjusted for the calculated smaller inner tumors during x- and y-axis scanning.

Figure 26A:
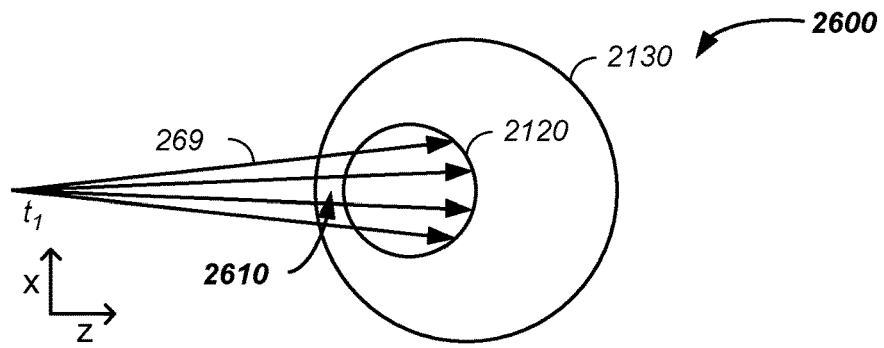
FIGS. 26(A-C) and FIG. 26E illustrate distal irradiation of a tumor from varying rotational directions and FIG. 26D illustrates integrated radiation resulting from distal radiation.
Figure 26B:
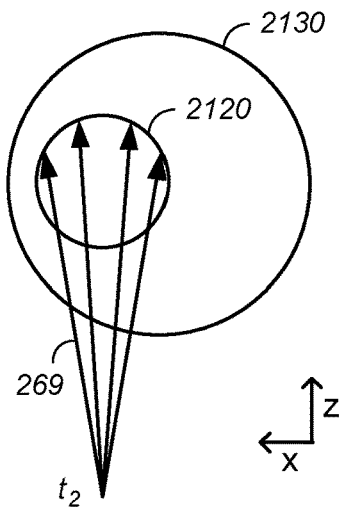

Referring now to FIG. 26A and FIG. 26B, the proton delivery enhancement method is further described. Referring now to FIG. 26A, at a first point in time protons are delivered to the tumor 2120 of the patient 2130 from a first direction. From the first rotational direction, the proton beam is scanned 269 across the tumor. As the proton beam is scanned across the tumor the energy of the proton beam is adjusted to allow the Bragg peak energy to target the distal portion of the tumor. Again, distal refers to the back portion of the tumor located furthest away from where the charged particles enter the tumor. As illustrated, the proton beam is scanned along an x-axis across the patient. This process allows the Bragg peak energy to fall within the tumor, for the middle area of the Bragg peak profile to fall in the middle and proximal portion of the tumor, and for the small intensity ingress portion of the Bragg peak to hit healthy tissue. In this manner, the maximum radiation dose is delivered to the tumor or the proton dose efficiency is maximized for the first rotational direction.

Figure 26C:
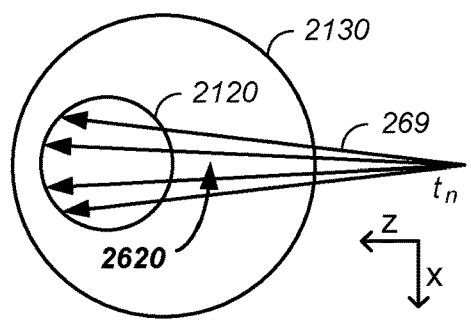

After irradiation from the first rotational position, the patient is rotated to a new rotational position. Referring now to FIG. 26B, the scanning of the proton beam is repeated. Again, the distal portion of the tumor is targeted with adjustment of the proton beam energy to target the Bragg peak energy to the distal portion of the tumor. Naturally, the distal portion of the tumor for the second rotational position is different from the distal portion of the tumor for the first rotational position. Referring now to FIG. 26C, the process of rotating the patient and then irradiating the new distal portion of the tumor is further illustrated at an $n^{th}$ rotational position. Preferably, the process of rotating the patient and scanning along the x- and y-axes with the Z-axes energy targeting the new distal portion of the tumor is repeated, such as with more than 5, 10, 20, or 30 rotational positions or with about 36 rotational positions.

Figure 26D:
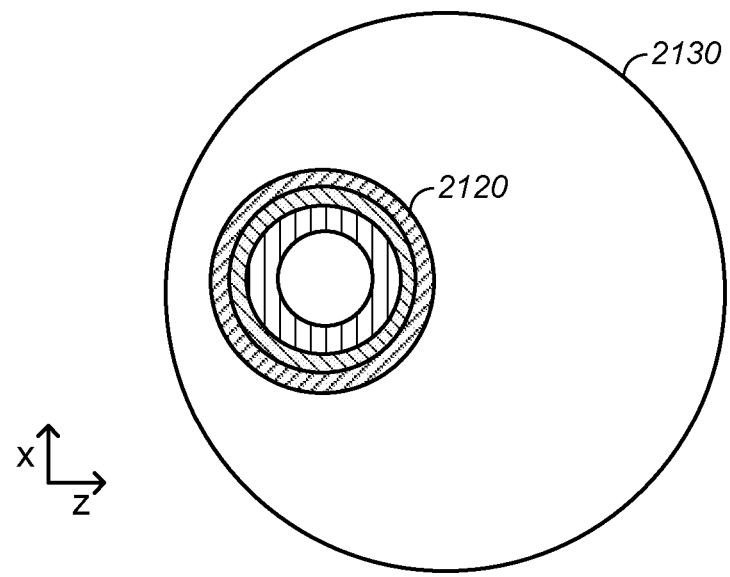
Figure 26E:
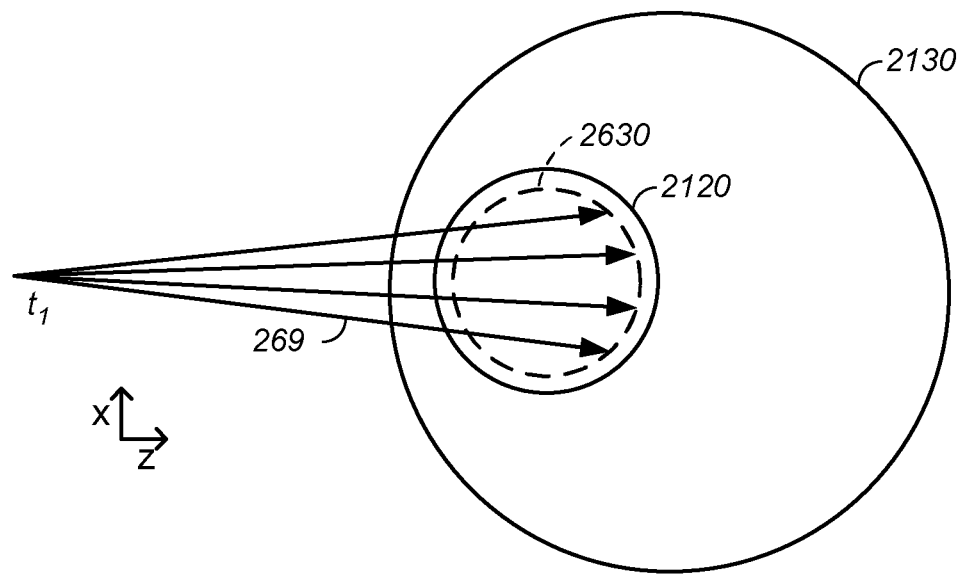

For clarity, FIGS. 26(A-C) and FIG. 26E show the proton beam as having moved, but in actuality, the proton beam is stationary and the patient is rotated, such as via use of rotating the bottom unit 2112 of the patient positioning system 2110. Also, FIGS. 26(A-C) and FIG. 26E show the proton beam being scanned across the tumor along the x-axis. Though not illustrated for clarity, the proton beam is additionally scanned up and down the tumor along the y-axis of the patient. Combined, the distal portion or volume of the tumor is irradiated along the x- and y-axes with adjustment of the z-axis energy level of the proton beam. In one case, the tumor is scanned along the x-axis and the scanning is repeated along the x-axis for multiple y-axis positions. In another case, the tumor is scanned along the y-axis and the scanning is repeated along the y-axis for multiple x-axis positions. In yet another case, the tumor is scanned by simultaneously adjusting the x- and y-axes so that the distal portion of the tumor is targeted. In all of these cases, the z-axis or energy of the proton beam is adjusted along the contour of the distal portion of the tumor to target the Bragg peak energy to the distal portion of the tumor.

Referring now to FIG. 26D, after targeting the distal portion of the tumor from multiple directions, such as through 360 degrees, the outer perimeter of the tumor has been strongly irradiated with peak Bragg profile energy, the middle of the Bragg peak energy profile energy has been delivered along an inner edge of the heavily irradiated tumor perimeter, and smaller dosages from the ingress portion of the Bragg energy profile are distributed throughout the tumor and into some healthy tissue. The delivered dosages or accumulated radiation flux levels are illustrated in a cross-sectional area of the tumor 2120 using an iso-line plot.

After a first full rotation of the patient, symbolically, the darkest regions of the tumor are nearly fully irradiated and the regions of the tissue having received less radiation are illustrated with a gray scale with the whitest portions having the lowest radiation dose.

Referring now to FIG. 26E, after completing the distal targeting multi-field irradiation, a smaller inner tumor is defined, where the inner tumor is already partially irradiated. The smaller inner tumor is indicated by the dashed line 2630. The above process of irradiating the tumor is repeated for the newly defined smaller tumor. The proton dosages to the outer or distal portions of the smaller tumor are adjusted to account for the dosages delivered from other rotational positions. After the second tumor is irradiated, a yet smaller third tumor is defined. The process is repeated until the entire tumor is irradiated at the prescribed or defined dosage.

As described at the onset of this example, the patient is preferably only rotated to each rotational position once. In the above described example, after irradiation of the outer perimeter of the tumor, the patient is rotationally positioned, such as through 360 degrees, and the distal portion of the newest smaller tumor is targeted as described, supra. However, the irradiation dosage to be delivered to the second smaller tumor and each subsequently smaller tumor is known a-priori. Hence, when at a given angle of rotation, the smaller tumor or multiple progressively smaller tumors, are optionally targeted so that the patient is only rotated to the multiple rotational irradiation positions once.

The goal is to deliver a treatment dosage to each position of the tumor, to preferably not exceed the treatment dosage to any position of the tumor, to minimize ingress radiation dosage to healthy tissue, to circumferentially distribute ingress radiation hitting the healthy tissue, and to further minimize ingress radiation dosage to sensitive areas. Since the Bragg energy profile is known, it is possible to calculated the optimal intensity and energy of the proton beam for each rotational position and for each x- and y-axis scanning position. These calculation result in slightly less than threshold radiation dosage to be delivered to the distal portion of the tumor for each rotational position as the ingress dose energy from other positions bring the total dose energy for the targeted position up to the threshold delivery dose.

Referring again to FIG. 26A and FIG. 26C, the intensity of the proton beam is preferably adjusted to account for the cross-sectional distance or density of the healthy tissue. An example is used for clarity. Referring now to FIG. 26A, when irradiating from the first position where the healthy tissue has a small area 2610, the intensity of the proton beam is preferably increased as relatively less energy is delivered by the ingress portion of the Bragg profile to the healthy tissue. Referring now to FIG. 26C, in contrast when irradiating from the $n^{th}$ rotational position where the healthy tissue has a large cross-sectional area 2620, the intensity of the proton beam is preferably decreased as a greater fraction the proton dose is delivered to the healthy tissue from this orientation.

In one example, for each rotational position and/or for each z-axis distance into the tumor, the efficiency of proton dose delivery to the tumor is calculated. The intensity of the proton beam is made proportional to the calculated efficiency. Essentially, when the scanning direction has really good efficiency, the intensity is increased and vise-versa. For example, if the tumor is elongated, generally the efficiency of irradiating the distal portion by going through the length of the tumor is higher than irradiating a distal region of the tumor by going across the tumor with the Bragg energy distribution. Generally, in the optimization algorithm:

distal portions of the tumor are targeted for each rotational position;
 the intensity of the proton beam is largest with the largest cross-sectional area of the tumor;
 intensity is larger when the intervening healthy tissue volume is smallest; and
 intensity is minimized or cut to zero when the intervening healthy tissue volume includes sensitive tissue, such as the spinal cord or eyes.

Using an algorithm so defined, the efficiency of radiation dose delivery to the tumor is maximized. More particularly, the ratio of radiation dose delivered to the tumor versus the radiation dose delivered to surrounding healthy tissue approaches a maximum. Further, integrated radiation dose delivery to each x, y, and z-axis volume of the tumor as a result of irradiation from multiple rotation directions is at or near the preferred dose level. Still further, ingress radiation dose delivery to healthy tissue is circumferentially distributed about the tumor via use of multi-field irradiation where radiation is delivered from a plurality of directions into the body, such as more than 5, 10, 20, or 30 directions.

Multi-Field Irradiation

In one multi-field irradiation example, the particle therapy system with a synchrotron ring diameter of less than six meters includes ability to:

rotate the patient through about 360 degrees;
 extract radiation in about 0.1 to 10 seconds;
 scan vertically about 100 millimeters;
 scan horizontally about 700 millimeters;
 vary beam energy from about 30 to 330 MeV/second during irradiation;
 vary the proton beam intensity independently of varying the proton beam energy;
 focus the proton beam with a cross-sectional distance from about 2 to 20 millimeters at the tumor; and/or
 complete multi-field irradiation of a tumor in less than about 1, 2, 4, or 6 minutes as measured from the time of initiating proton delivery to the patient 2130.

Two multi-field irradiation methods are described. In the first method, the main controller 110 rotationally positions the patient 2130 and subsequently irradiates the tumor 2120. The process is repeated until a multi-field irradiation plan is complete. In the second method, the main controller 110 simultaneously rotates and irradiates the tumor 2120 within the patient 2130 until the multi-field irradiation plan is complete. More particularly, the proton beam irradiation occurs while the patient 2130 is being rotated.

The 3-dimensional scanning system of the proton spot focal point, described herein, is preferably combined with a rotation/raster method. The method includes layer wise tumor irradiation from many directions. During a given irradiation slice, the proton beam energy is continuously changed according to the tissue's density in front of the tumor to result in the beam stopping point, defined by the Bragg peak, always being inside the tumor and inside the irradiated slice. The novel method allows for irradiation from many directions, referred to herein as multi-field irradiation, to achieve the maximal effective dose at the tumor level while simultaneously significantly reducing possible side-effects on the surrounding healthy tissues in comparison to existing methods. Essentially, the multi-field irradiation system distributes dose-distribution at tissue depths not yet reaching the tumor.

Proton Beam Position Control

Figure 27A:
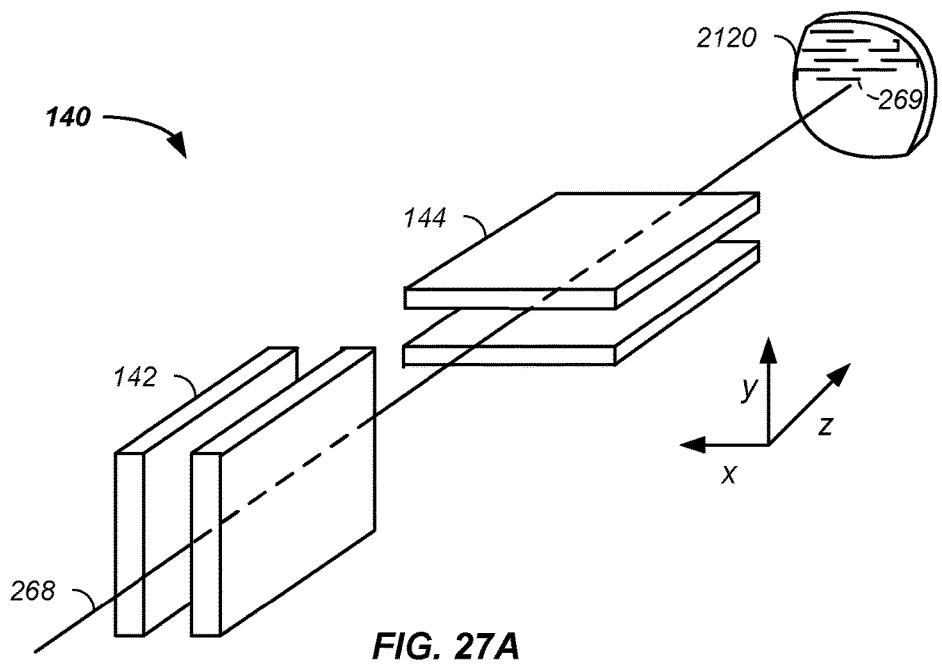
FIG. 27A and FIG. 27B illustrate multi-dimensional scanning of a charged particle beam spot scanning system operating on: (A) a 2-D slice or (B) a 3-D volume of a tumor, respectively.
Figure 27B:
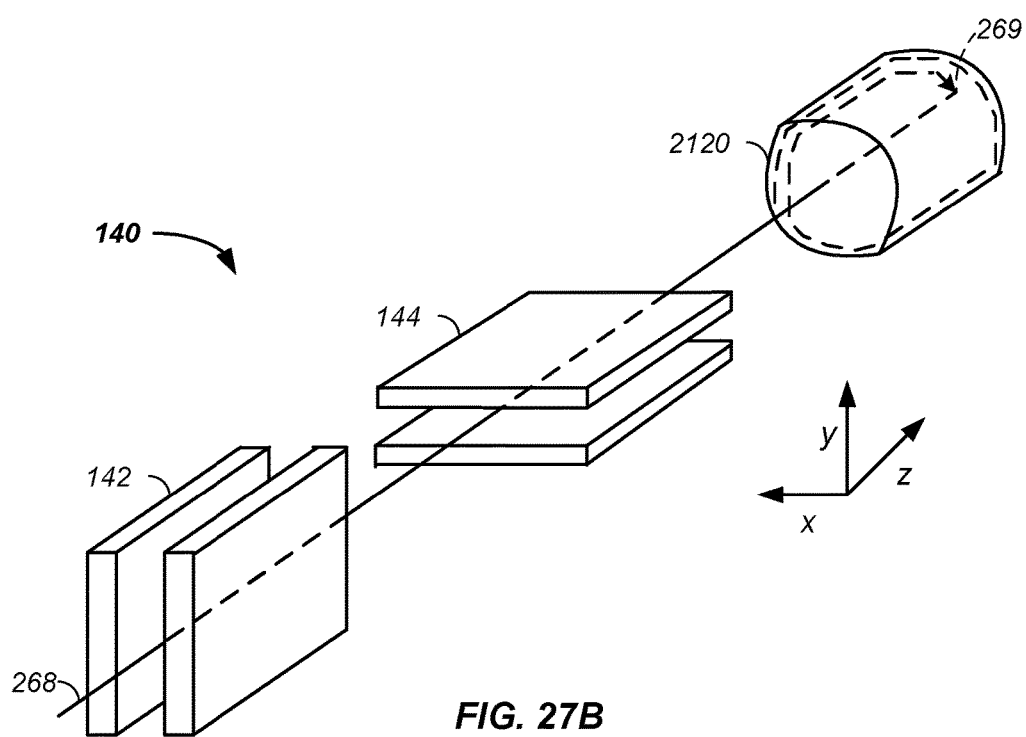

Referring now to FIG. 27A and FIG. 27B, a beam delivery and tissue volume scanning system is illustrated. Presently, the worldwide radiotherapy community uses a method of dose field forming using a pencil beam scanning system. In stark contrast, FIG. 27A and FIG. 27B illustrate a spot scanning system or tissue volume scanning system. In the tissue volume scanning system, the proton beam is controlled, in terms of transportation and distribution, using an inexpensive and precise scanning system. The scanning system is an active system, where the beam is focused into a spot focal point of about one-half, one, two, or three millimeters in diameter. The focal point is translated along two axes while simultaneously altering the applied energy of the proton beam, which effectively changes the third dimension of the focal point. The system is applicable in combination with the above described rotation of the body, which preferably occurs in-between individual moments or cycles of proton delivery to the tumor. Optionally, the rotation of the body by the above described system occurs continuously and simultaneously with proton delivery to the tumor.

For example, in the illustrated system in FIG. 27A, the spot is translated horizontally, is moved down a vertical y-axis, and is then back along the horizontal axis. In this example, current is used to control a vertical scanning system having at least one magnet. The applied current alters the magnetic field of the vertical scanning system to control the vertical deflection of the proton beam. Similarly, a horizontal scanning magnet system controls the horizontal deflection of the proton beam. The degree of transport along each axes is controlled to conform to the tumor cross-section at the given depth. The depth is controlled by changing the energy of the proton beam. For example, the proton beam energy is decreased, so as to define a new penetration depth, and the scanning process is repeated along the horizontal and vertical axes covering a new cross-sectional area of the tumor. Combined, the three axes of control allow scanning or movement of the proton beam focal point over the entire volume of the cancerous tumor. The time at each spot and the direction into the body for each spot is controlled to yield the desired radiation does at each sub-volume of the cancerous volume while distributing energy hitting outside of the tumor.

The focused beam spot volume dimension is preferably tightly controlled to a diameter of about 0.5, 1, or 2 millimeters, but is alternatively several centimeters in diameter. Preferred design controls allow scanning in two directions with: (1) a vertical amplitude of about 100 mm amplitude and frequency up to about 200 Hz; and (2) a horizontal amplitude of about 700 mm amplitude and frequency up to about 1 Hz.

Proton Beam Energy Control

In FIG. 27A, the proton beam is illustrated along a z-axis controlled by the beam energy, the horizontal movement is along an x-axis, and the vertical direction is along a y-axis. The distance the protons move along the z-axis into the tissue, in this example, is controlled by the kinetic energy of the proton. This coordinate system is arbitrary and exemplary. Referring now to FIG. 27B, preferably control of the proton beam is controlled in 3-dimensional space using two scanning magnet systems and by simultaneously varying and controlling the kinetic energy of the proton beam. The use of the extraction system, described supra, allows for different scanning patterns. Particularly, the system allows simultaneous adjustment of the x-, y-, and z-axes in the irradiation of the solid tumor. Stated again, instead of scanning along an x,y-plane and then adjusting energy of the protons, such as with a range modulation wheel, the system allows for moving along the z-axes while simultaneously adjusting the x- and or y-axes. Hence, rather than irradiating slices of the tumor, the tumor is optionally irradiated in three simultaneous dimensions. For example, the tumor is irradiated around an outer edge of the tumor in three dimensions. Then the tumor is irradiated around an outer edge of an internal section of the tumor. This process is repeated until the entire tumor is irradiated. The outer edge irradiation is preferably coupled with simultaneous rotation of the subject, such as about a vertical y-axis. This system allows for maximum efficiency of deposition of protons to the tumor, as defined as the ratio of the proton irradiation energy delivered to the tumor relative to the proton irradiation energy delivered to the healthy tissue.

Combined, the system allows for multi-axes control of the charged particle beam system in a small space with a low or small power supply. For example, the system uses multiple magnets where each magnet has at least one edge focusing effect in each turning section of the synchrotron and/or multiple magnets having concentrating magnetic field geometry, as described supra. The multiple edge focusing effects in the circulating beam path of the synchrotron combined with the concentration geometry of the magnets and described extraction system yields a synchrotron having:

- a small circumference system, such as less than about 50 meters;
- a vertical proton beam size gap of about 2 cm;
- corresponding reduced power supply requirements associated with the reduced gap size;
- an extraction system not requiring a newly introduced magnetic field;
- acceleration or deceleration of the protons during extraction; and
- control of z-axis energy during extraction.

The result is a 3-dimensional scanning system, x-, y-, and z-axes control, where the z-axes control resides in the synchrotron and where the z-axes energy is variably controlled during the extraction process inside the synchrotron.

Proton Beam Intensity Control

Figure 28A:
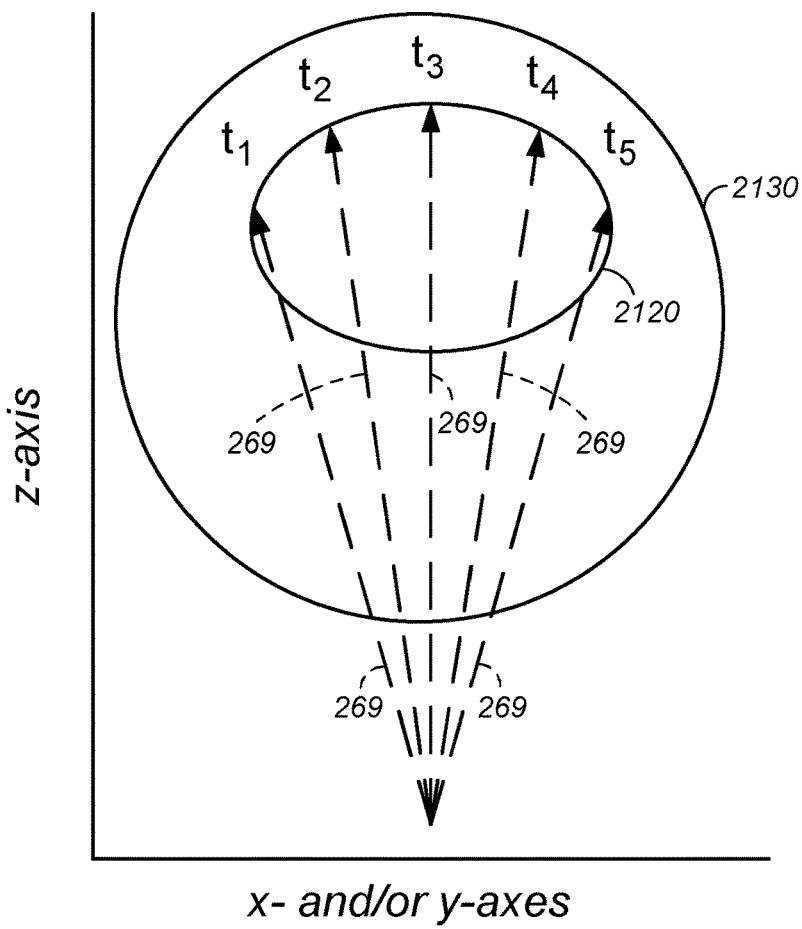
FIG. 28A and FIG. 28B illustrate (A) irradiating varying depths within a tumor and (B) changes in irradiation intensity correlating with the varying depths in the tumor, respectively.
Figure 28B:
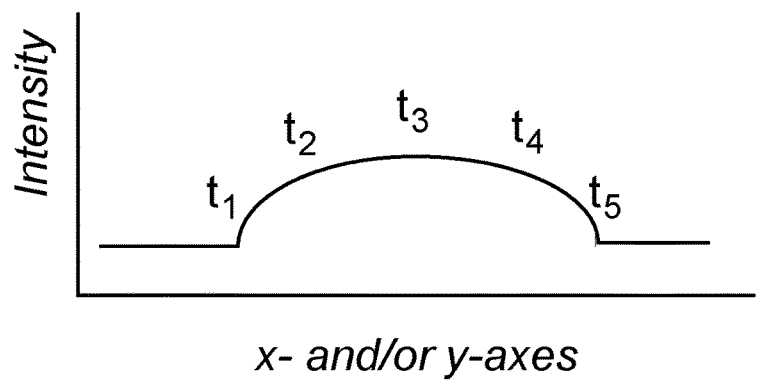

Referring now to FIG. 28A and FIG. 28B, an intensity modulated 3-dimensional scanning system 2800 is described. Referring now to FIG. 28A, a proton beam is being scanned across and x- and/or y-axis as a function of time. With each time, the z-axis energy is optionally adjusted. In this case, from the first time, $t_1$, to the third time, $t_3$, the energy is increased, and from the third time, $t_3$, to the fifth time, $t_5$, the energy is decreased. Thus, the system is scanning in 3-dimensions along the x-, y-, and/or z-axes. Notably, the radiation energy delivery efficiency is increasing from $t_1$ to $t_3$ and decreasing from $t_3$ to $t_5$, where efficiency refers to the percentage of radiation delivered to the tumor. For example, at the third time, $t_3$, the Bragg peak energy is located at the distal, or back, portion of the tumor located furthest away from the point of origin where the charged particles enter the tumor 2120. Delivered Bragg peak energy increases exponentially up to the maximum distance of proton energy penetration into the body. Hence, as illustrated the percentage of the delivered Bragg peak energy in the tumor is greatest at the third time period $t_3$, which has the largest tumor cross-section pathlength, less at the second and fourth time periods, $t_2$ and $t_4$, and still less at the first and fifth time periods, $t_1$ and $t_5$, which have the smallest tumor cross-section pathlength Referring now to FIG. 28B, the intensity of the proton beam is also changing with time in a manner correlated with the radiation energy delivery efficiency. In this case, the intensity of the proton beam is greatest at the third time period $t_3$, less at the second and fourth time periods, $t_2$ and $t_4$, and still less at the first and fifth time periods, $t_1$ and $t_5$. The intensity of the proton beam is adjusted to be more intense when radiation delivery efficiency increases using the proton beam extraction process 1800 and intensity control system 1900, described supra. Intensity is generally positively correlated with tumor cross-sectional pathlength, proton beam energy, and/or radiation delivery efficiency. Preferably, the distal portion of the tumor is targeted with each rotational position of the patient 2130 using the multi-field irradiation 2500, described supra, allowing repeated use of increased intensity at changing distal portions of the tumor 2120 as the patient 2130 is rotated in the multi-field irradiation system 2500.

As an example, the intensity controller subsystem 1940 adjusts the radio-frequency field in the RF cavity system 1910 to yield an intensity to correlate with radiation delivery efficiency and/or with the irradiation plan 1960. Preferably, the intensity controller subsystem adjusts the intensity of the radiation beam using a reading of the actual intensity of the proton beam 1950 or from the feedback current from the extraction material 1930, which is proportional to the extracted beam intensity, as described supra. Thus, independent of the x- and y-axes targeting system and independent of the z-axis energy of the proton beam, the intensity of the proton beam is controlled, preferably in coordination with the multi-field irradiation system 2500, to yield peak intensities with greatest radiation delivery efficiency. The independent control of beam parameters allows use of a raster beam scanning system. Often, the greatest radiation delivery efficiency occurs, for a given rotational position of the patient, when the energy of the proton beam is largest. Hence, the intensity of the proton beam optionally correlates with the energy of the proton beam. The system is optionally timed with the patient's respiration cycle, as described infra. The system optionally operates in a raster beam scanning mode, as described infra.

Proton Beam Position, Energy, and Intensity Control

An example of a proton scanning or targeting system 140 used to direct the protons to the tumor with 4-dimensional scanning control is provided, where the 4-dimensional scanning control is along the x-, y-, and z-axes along with intensity control, as described supra. A fifth controllable axis is time. A sixth controllable axis is patient rotation. Typically, charged particles traveling along the transport path 268 are directed through a first axis control element 142, such as a vertical control, and a second axis control element 144, such as a horizontal control and into a tumor 2120. As described, supra, the extraction system also allows for simultaneous variation in the z-axis. Further, as described, supra, the intensity or dose of the extracted beam is optionally simultaneously and independently controlled and varied. Thus instead of irradiating a slice of the tumor, as in FIG. 27A, all four dimensions defining the targeting spot of the proton delivery in the tumor are simultaneously variable. The simultaneous variation of the proton delivery spot is illustrated in FIG. 27B by the spot delivery path 269 and in FIG. 28A, where the intensity is controlled as a function of efficiency of radiation delivery.

In one example, the protons are initially directed around an outer edge of the tumor and are then directed around an inner radius of the tumor. Combined with rotation of the subject about a vertical axis, a multi-field irradiation process is used where a not yet irradiated portion of the tumor is preferably irradiated at the further distance of the tumor from the proton entry point into the body. This yields the greatest percentage of the proton delivery, as defined by the Bragg peak, into the tumor and minimizes damage to peripheral healthy tissue.

Raster Scanning

Raster beam scanning is optionally used. In traditional spot targeting systems, a spot of the tumor is targeted, then the radiation beam is turned off, a new spot is targeted, and the radiation beam is turned on. The cycle is repeated with changes in the x- and/or y-axis position. In stark contrast, in the raster beam scanning system, the proton beam is scanned from position to position in the tumor without turning off the radiation beam. In the raster scanning system, the irradiation is not necessarily turned off between spots, rather the irradiation of the tumor is optionally continuous as the beam scans between 3-dimensional locations in the tumor. The velocity of the scanning raster beam is optionally independently controlled. Velocity is change in the x, y, z position of the spot of the scanning beam with time. Hence, in a velocity control system, the rate of movement of the proton beam from coordinate to coordinate optionally varies with time or has a mathematical change in velocity with time. Stated again, the movement of the spot of the scanning beam with time is optionally not constant as a function of time. Further, the raster beam scanning system optionally uses the simultaneous and/or independent control of the x- and/or y-axes position, energy of the proton beam, intensity of the proton beam, and rotational position of the patient using the acceleration, extraction systems, and rotation systems, described supra.

In one example, a charged particle beam system for irradiation of a tumor of a patient, includes: a synchrotron configured with an extraction foil, where a timing controller times the charged particle beam striking the extraction foil in an acceleration period in the synchrotron resulting in extraction of the charged particle beam at a selected energy and a raster beam scanning system configured to scan the charged particle beam across delivery positions while both (1) constantly delivering the charged particle beam at and between the delivery positions and (2) simultaneously varying the selected energy level of the charged particle beam across the delivery positions. Preferably, an intensity controller is used that is configured to measure a current resulting from the charged particle beam striking the extraction foil, the current used as a feedback control to a radio-frequency cavity system, wherein an applied radio frequency, using the feedback control, in the radio-frequency cavity system controls the number of particles in the charged particle beam striking the extraction foil resulting in intensity control of the charged particle beam. Preferably, a velocity controller is configured to change a rate of movement of the charged particle beam between the delivery position along x- and/or y-axes in the tumor as a function of time.

Imaging/X-Ray System

Herein, an X-ray system is used to illustrate an imaging system.

Timing

An X-ray is preferably collected either (1) just before or (2) concurrently with treating a subject with proton therapy for a couple of reasons. First, movement of the body, described supra, changes the local position of the tumor in the body relative to other body constituents. If the patient or subject 2130 has an X-ray taken and is then bodily moved to a proton treatment room, accurate alignment of the proton beam to the tumor is problematic. Alignment of the proton beam to the tumor 2120 using one or more X-rays is best performed at the time of proton delivery or in the seconds or minutes immediately prior to proton delivery and after the patient is placed into a therapeutic body position, which is typically a fixed position or partially immobilized position. Second, the X-ray taken after positioning the patient is used for verification of proton beam alignment to a targeted position, such as a tumor and/or internal organ position.

Positioning

An X-ray is preferably taken just before treating the subject to aid in patient positioning. For positioning purposes, an X-ray of a large body area is not needed. In one embodiment, an X-ray of only a local area is collected. When collecting an X-ray, the X-ray has an X-ray path. The proton beam has a proton beam path. Overlaying the X-ray path with the proton beam path is one method of aligning the proton beam to the tumor. However, this method involves putting the X-ray equipment into the proton beam path, taking the X-ray, and then moving the X-ray equipment out of the beam path. This process takes time. The elapsed time while the X-ray equipment moves has a couple of detrimental effects. First, during the time required to move the X-ray equipment, the body moves. The resulting movement decreases precision and/or accuracy of subsequent proton beam alignment to the tumor. Second, the time required to move the X-ray equipment is time that the proton beam therapy system is not in use, which decreases the total efficiency of the proton beam therapy system.

X-Ray Source Lifetime

Preferably, components in the particle beam therapy system require minimal or no maintenance over the lifetime of the particle beam therapy system. For example, it is desirable to equip the proton beam therapy system with an X-ray system having a long lifetime source, such as a lifetime of about 20 years.

In one system, described infra, electrons are used to create X-rays. The electrons are generated at a cathode where the lifetime of the cathode is temperature dependent. Analogous to a light bulb, where the filament is kept in equilibrium, the cathode temperature is held in equilibrium at temperatures at about 200, 500, or 1000 degrees Celsius. Reduction of the cathode temperature results in increased lifetime of the cathode. Hence, the cathode used in generating the electrons is preferably held at as low of a temperature as possible. However, if the temperature of the cathode is reduced, then electron emissions also decrease. To overcome the need for more electrons at lower temperatures, a large cathode is used and the generated electrons are concentrated. The process is analogous to compressing electrons in an electron gun; however, here the compression techniques are adapted to apply to enhancing an X-ray tube lifetime.

Figure 29:
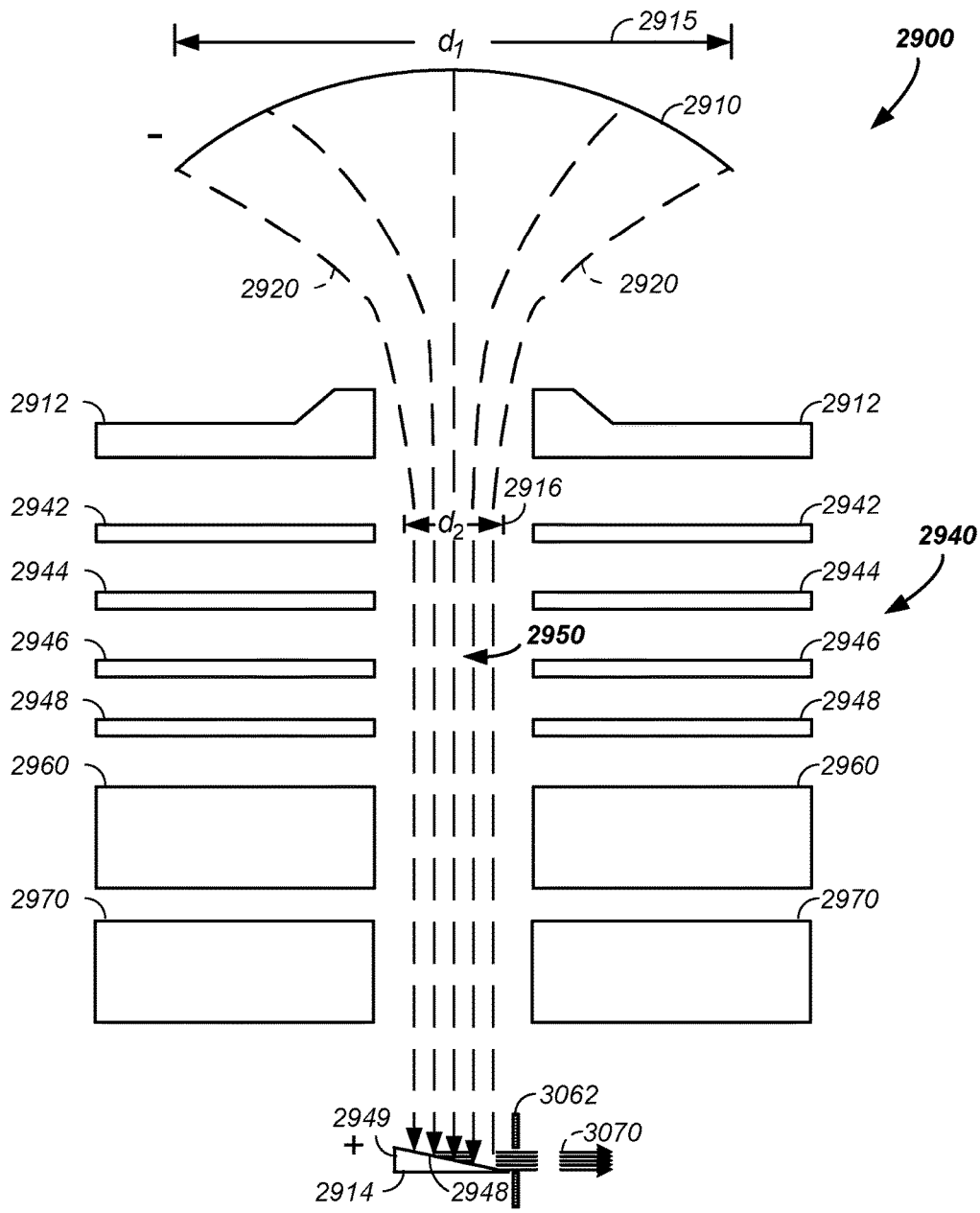
FIG. 29 illustrates an electron gun source used in generating X-rays coupled with a particle beam therapy system.

Referring now to FIG. 29, an example of an X-ray generation device 2900 having an enhanced lifetime is provided. Electrons 2920 are generated at a cathode 2910, focused with a control electrode 2912, and accelerated with a series of accelerating electrodes 2940. The accelerated electrons 2950 impact an X-ray generation source 2948 resulting in generated X-rays that are then directed along an X-ray path 3070 to the subject 2130. The concentrating of the electrons from a first diameter 2915 to a second diameter 2916 allows the cathode to operate at a reduced temperature and still yield the necessary amplified level of electrons at the X-ray generation source 2948. In one example, the X-ray generation source 2948 is the anode coupled with the cathode 2910 and/or the X-ray generation source is substantially composed of tungsten.

Still referring to FIG. 29, a more detailed description of an exemplary X-ray generation device 2900 is described. An anode 2914/cathode 2910 pair is used to generated electrons. The electrons 2920 are generated at the cathode 2910 having a first diameter 2915, which is denoted $d_1$. The control electrodes 2912 attract the generated electrons 2920. For example, if the cathode is held at about −150 kV and the control electrode is held at about −149 kV, then the generated electrons 2920 are attracted toward the control electrodes 2912 and focused. A series of accelerating electrodes 2940 are then used to accelerate the electrons into a substantially parallel path 2950 with a smaller diameter 2916, which is denoted $d_2$. For example, with the cathode held at −150 kV, a first, second, third, and fourth accelerating electrodes 2942, 2944, 2946, 2948 are held at about −120, −90, −60, and −30 kV, respectively. If a thinner body part is to be analyzed, then the cathode 2910 is held at a smaller level, such as about −90 kV and the control electrode, first, second, third, and fourth electrode are each adjusted to lower levels. Generally, the voltage difference from the cathode to fourth electrode is less for a smaller negative voltage at the cathode and vise-versa. The accelerated electrons 2950 are optionally passed through a magnetic lens 2960 for adjustment of beam size, such as a cylindrical magnetic lens. The electrons are also optionally focused using quadrupole magnets 2970, which focus in one direction and defocus in another direction. The accelerated electrons 2950, which are now adjusted in beam size and focused strike the X-ray generation source 2948, such as tungsten, resulting in generated X-rays that pass through an optional blocker 3062 and proceed along an X-ray path 3070 to the subject. The X-ray generation source 2948 is optionally cooled with a cooling element 2949, such as water touching or thermally connected to a backside of the X-ray generation source 2948. The concentrating of the electrons from a first diameter 2915 to a second diameter 2916 allows the cathode to operate at a reduced temperature and still yield the necessary amplified level of electrons at the X-ray generation source 2948.

More generally, the X-ray generation device 2900 produces electrons having initial vectors. One or more of the control electrode 2912, accelerating electrodes 2940, magnetic lens 2960, and quadrupole magnets 2970 combine to alter the initial electron vectors into parallel vectors with a decreased cross-sectional area having a substantially parallel path, referred to as the accelerated electrons 2950. The process allows the X-ray generation device 2900 to operate at a lower temperature. Particularly, instead of using a cathode that is the size of the electron beam needed, a larger electrode is used and the resulting electrons 2920 are focused and/or concentrated into the required electron beam needed. As lifetime is roughly an inverse of current density, the concentration of the current density results in a larger lifetime of the X-ray generation device. A specific example is provided for clarity. If the cathode has a fifteen mm radius or $d_1$ is about 30 mm, then the area ($\pi r^2$) is about 225 mm² times pi. If the concentration of the electrons achieves a radius of five mm or $d_2$ is about 10 mm, then the area ($\pi r^2$) is about 25 mm² times pi. The ratio of the two areas is about nine ($225\pi/25\pi$). Thus, there is about nine times less density of current at the larger cathode compared to the traditional cathode having an area of the desired electron beam. Hence, the lifetime of the larger cathode approximates nine times the lifetime of the traditional cathode, though the actual current through the larger cathode and traditional cathode is about the same. Preferably, the area of the cathode 2910 is about 2, 4, 6, 8, 10, 15, 20, or 25 times that of the cross-sectional area of the substantially parallel electron beam 2950.

In another embodiment of the invention, the quadrupole magnets 2970 result in an oblong cross-sectional shape of the electron beam 2950. A projection of the oblong cross-sectional shape of the electron beam 2950 onto the X-ray generation source 2948 results in an X-ray beam 3070 that has a small spot in cross-sectional view, which is preferably substantially circular in cross-sectional shape, that is then passed through the patient 2930. The small spot is used to yield an X-ray having enhanced resolution at the patient.

Figure 30:
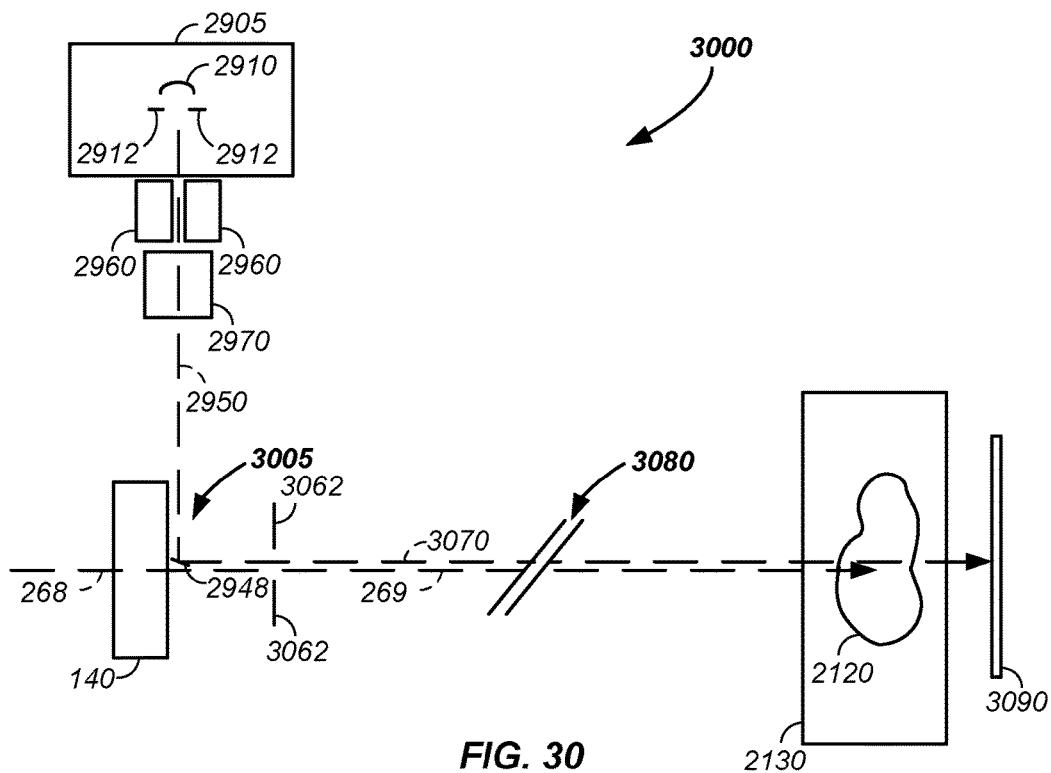
FIG. 30 illustrates an X-ray source proximate a particle beam path.

Referring now to FIG. 30, in one embodiment, an X-ray is generated close to, but not in, the proton beam path. A proton beam therapy system and an X-ray system combination 3000 is illustrated in FIG. 30. The proton beam therapy system has a proton beam 268 in a transport system after the Lamberson extraction magnet 292 of the synchrotron 130. The proton beam is directed by the scanning/targeting/delivery system 140 to a tumor 2120 of a patient 2130. The X-ray system 3005 includes an electron beam source 2905 generating an electron beam 2950. The electron beam is directed to an X-ray generation source 2948, such as a piece of tungsten. Preferably, the tungsten X-ray source is located about 1, 2, 3, 5, 10, 15, or 20 millimeters from the proton beam path 268. When the electron beam 2950 hits the tungsten, X-rays are generated in all directions. X-rays are blocked with a port 3062 and are selected for an X-ray beam path 3070. The X-ray beam path 3070 and proton beam path 268 run substantially in parallel as they progress to the tumor 2120. The distance between the X-ray beam path 3070 and proton beam path 269 preferably diminishes to near zero and/or the X-ray beam path 3070 and proton beam path 269 overlap by the time they reach the tumor 2120. Simple geometry shows this to be the case given the long distance, of at least a meter, between the tungsten and the tumor 2120. The distance is illustrated as a gap 3080 in FIG. 30. The X-rays are detected at an X-ray detector 3090, which is used to form an image of the tumor 2120 and/or position of the patient 2130.

As a whole, the system generates an X-ray beam that lies in substantially the same path as the proton therapy beam. The X-ray beam is generated by striking a tungsten or equivalent material with an electron beam. The X-ray generation source is located proximate to the proton beam path. Geometry of the incident electrons, geometry of the X-ray generation material, and/or geometry of the X-ray beam blocker 262 yield an X-ray beam that runs either substantially in parallel with the proton beam or results in an X-ray beam path that starts proximate the proton beam path an expands to cover and transmit through a tumor cross-sectional area to strike an X-ray detector array or film allowing imaging of the tumor from a direction and alignment of the proton therapy beam. The X-ray image is then used to control the charged particle beam path to accurately and precisely target the tumor, and/or is used in system verification and validation.

Figure 31:
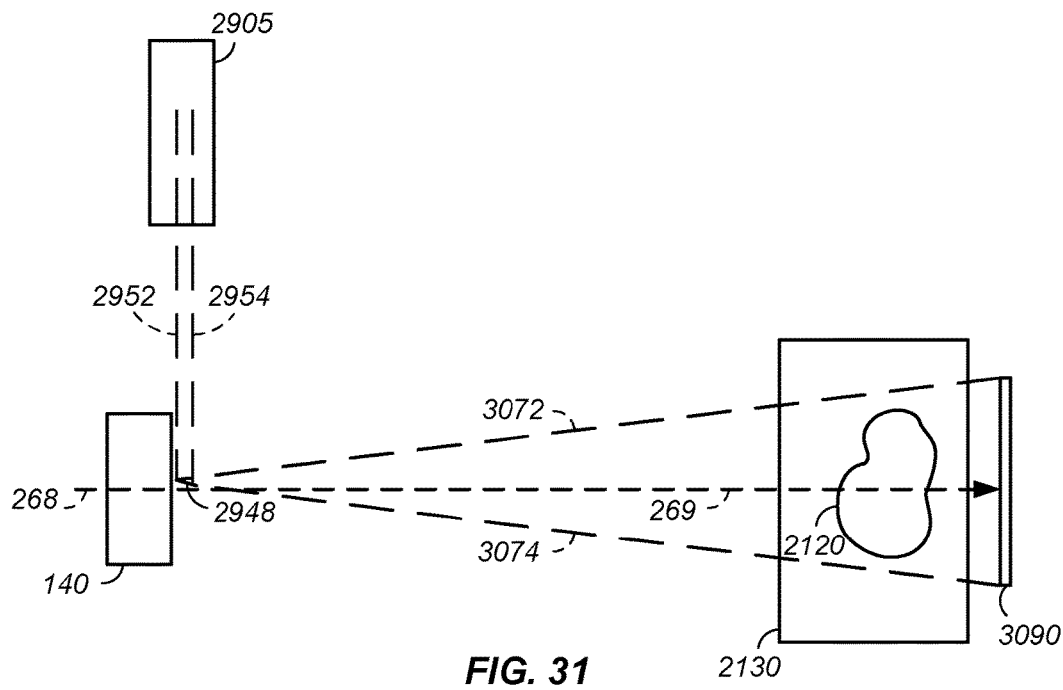
FIG. 31 illustrates an expanded X-ray beam path.

Referring now to FIG. 31, additional geometry of the electron beam path 2950 and X-ray beam path 3070 is illustrated. Particularly, the electron beam 2950 is shown as an expanded electron beam path 2952, 2954. Also, the X-ray beam path 3070 is shown as an expanded X-ray beam path 3072, 3074.

Figure 32:
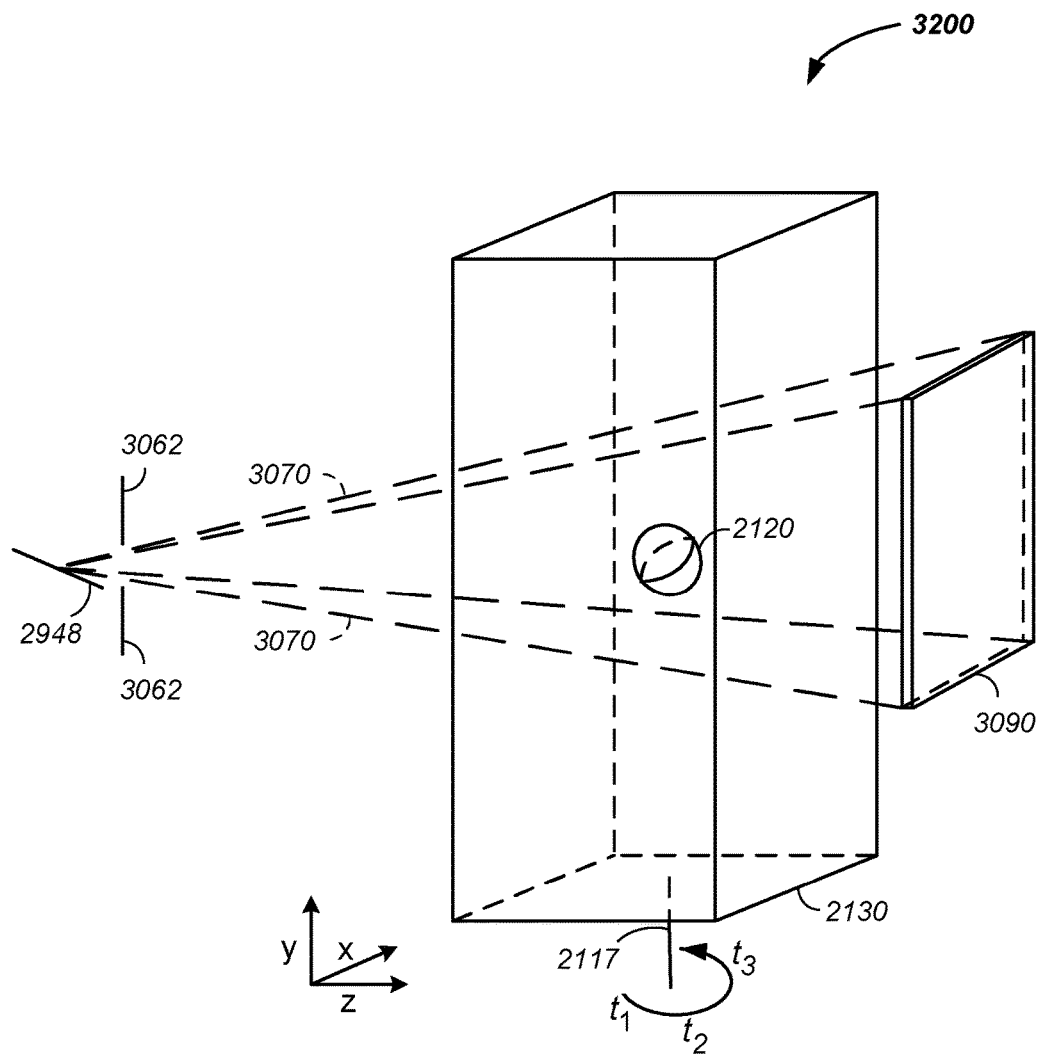
FIG. 32 provides an X-ray tomography system.

Referring now to FIG. 32, a 3-dimensional (3-D) X-ray tomography system 3200 is presented. In a typical X-ray tomography system, the X-ray source and detector rotationally translate about a stationary subject. In the X-ray tomography system described herein, the X-ray source and detector are stationary and the patient 2130 rotates. The stationary X-ray source allows a system where the X-ray source 2948 is proximate the proton therapy beam path 268, as described supra. In addition, the rotation of the patient 2130 allows the proton dosage to be distributed around the body, rather than being concentrated on one static entrance side of the body. Further, the 3-D X-ray tomography system allows for simultaneous updates of the tumor position relative to body constituents in real-time during proton therapy treatment of the tumor 2120 in the patient 2130. The X-ray tomography system is further described, infra.

Patient Imaging with Rotation

In a first step of the X-ray tomography system 3200, the patient 2130 is positioned relative to the X-ray beam path 3070 and proton beam path 268 using a patient semi-immobilization/placement system, described infra. After patient 2130 positioning, a series of reference 2-D X-ray images are collected, on a detector array 3090 or film, of the patient 2130 and tumor 2120 as the subject is rotated about a y-axis 2117. For example, a series of about 50, 100, 200, or 400 X-ray images of the patient are collected as the patient is rotated. In a second example, an X-ray image is collected with each n degrees of rotation of the patient 2130, where n is about ½, 1, 2, 3, 5, 10, or 20 degrees of rotation. Preferably, about 200 images are collected during one full rotation of the patient through 360 degrees. Subsequently, using the reference 2-D X-ray images, an algorithm produces a reference 3-D picture of the tumor 2120 relative to the patient's constituent body parts. A tumor 2120 irradiation plan is made using the 3-D picture of the tumor 2120 and the patient's constituent body parts. Creation of the proton irradiation plan is optionally performed after the patient has moved from the X-ray imaging area.

In a second step, the patient 2130 is repositioned relative to the X-ray beam path 3070 and proton beam path 268 using the patient semi-immobilization/placement system. Just prior to implementation of the proton irradiation plan, a few comparative X-ray images of the patient 2130 and tumor 2120 are collected at a limited number of positions using the X-ray tomography system 2600 setup. For example, a single X-ray image is collected with the patient positioned straight on, at angles of plus/minus forty-five degrees, and/or at angles of plus/minus ninety degrees relative to the proton beam path 268. The actual orientation of the patient 2130 relative to the proton beam path 268 is optionally any orientation. The actual number of comparative X-ray images is also optionally any number of images, though the preferable number of comparative X-ray images is about 2 to 5 comparative images. The comparative X-ray images are compared to the reference X-ray images and differences are detected. A medical expert or an algorithm determines if the difference between the reference images and the comparative images is significant. Based upon the differences, the medical expert or algorithm determines if: proton treatment should commence, be halted, or adapted in real-time. For example, if significant differences in the X-ray images are observed, then the treatment is preferably halted and the process of collecting a reference 3-D picture of the patient's tumor is reinitiated. In a second example, if the differences in the X-ray images are observed to be small, then the proton irradiation plan commences. In a third example, the algorithm or medical expert can adapt the proton irradiation plan in real-time to adjust for differences in tumor location resulting from changes in position of the tumor 2120 in the patient 2130 or from differences in the patient 2130 placement. In the third example, the adaptive proton therapy increases patient throughput and enhances precision and accuracy of proton irradiation of the tumor 2120 relative to the healthy tissue of the patient 2130.

Patient Immobilization

Accurate and precise delivery of a proton beam to a tumor of a patient requires: (1) positioning control of the proton beam and (2) positioning control of the patient. As described, supra, the proton beam is controlled using algorithms and magnetic fields to a diameter of about 0.5, 1, or 2 millimeters. This section addresses partial immobilization, restraint, and/or alignment of the patient to insure the tightly controlled proton beam efficiently hits a target tumor and not surrounding healthy tissue as a result of patient movement.

Herein, an x-, y-, and z-axes coordinate system and rotation axis is used to describe the orientation of the patient relative to the proton beam. The z-axis represent travel of the proton beam, such as the depth of the proton beam into the patient. When looking at the patient down the z-axis of travel of the proton beam, the x-axis refers to moving left or right across the patient and the y-axis refers to movement up or down the patient. A first rotation axis is rotation of the patient about the y-axis and is referred to herein as a rotation axis, bottom unit 2112 rotation axis, or y-axis of rotation 2117. In addition, tilt is rotation about the x-axis, yaw is rotation about the y-axis, and roll is rotation about the z-axis. In this coordinate system, the proton beam path 269 optionally runs in any direction. As an illustrative matter, the proton beam path running through a treatment room is described as running horizontally through the treatment room.

In this section, three examples of positioning systems are provided: (1) a semi-vertical partial immobilization system 3300; (2) a sitting partial immobilization system 3400; and (3) a laying position 3500. Elements described for one immobilization system apply to other immobilization systems with small changes. For example, a headrest, a head support, or head restraint will adjust along one axis for a reclined position, along a second axis for a seated position, and along a third axis for a laying position. However, the headrest itself is similar for each immobilization position.

Vertical Patient Positioning/Immobilization

Figure 33:
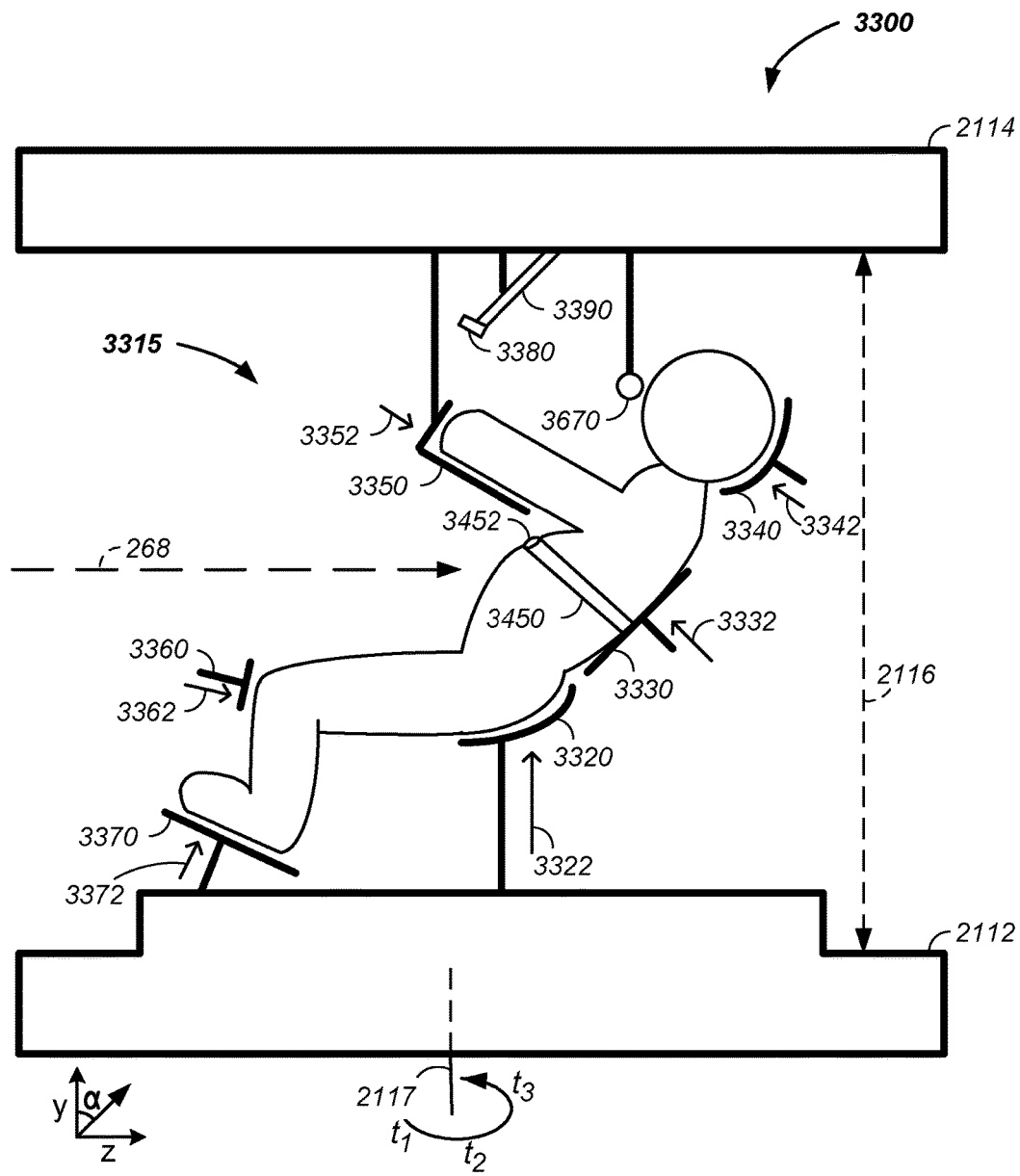
FIG. 33 illustrates a semi-vertical patient positioning system.

Referring now to FIG. 33, the semi-vertical patient positioning system 3300 is preferably used in conjunction with proton therapy of tumors in the torso. The patient positioning and/or immobilization system controls and/or restricts movement of the patient during proton beam therapy. In a first partial immobilization embodiment, the patient is positioned in a semi-vertical position in a proton beam therapy system. As illustrated, the patient is reclining at an angle alpha, α, about 45 degrees off of the y-axis as defined by an axis running from head to foot of the patient. More generally, the patient is optionally completely standing in a vertical position of zero degrees off the of y-axis or is in a semi-vertical position alpha that is reclined about 5, 10, 15, 20, 25, 30, 35, 40, 45, 50, 55, 60, or 65 degrees off of the y-axis toward the z-axis.

Patient positioning constraints 3315 that are used to maintain the patient in a treatment position, include one or more of: a seat support 3320, a back support 3330, a head support 3340, an arm support 3350, a knee support 3360, and a foot support 3370. The constraints are optionally and independently rigid or semi-rigid. Examples of a semi-rigid material include a high or low density foam or a visco-elastic foam. For example the foot support is preferably rigid and the back support is preferably semi-rigid, such as a high density foam material. One or more of the positioning constraints 3315 are movable and/or under computer control for rapid positioning and/or immobilization of the patient. For example, the seat support 3320 is adjustable along a seat adjustment axis 3322, which is preferably the y-axis; the back support 3330 is adjustable along a back support axis 3332, which is preferably dominated by z-axis movement with a y-axis element; the head support 3340 is adjustable along a head support axis 3342, which is preferably dominated by z-axis movement with a y-axis element; the arm support 3350 is adjustable along an arm support axis 3352, which is preferably dominated by z-axis movement with a y-axis element; the knee support 3360 is adjustable along a knee support axis 3362, which is preferably dominated by z-axis movement with a y-axis element; and the foot support 3370 is adjustable along a foot support axis 3372, which is preferably dominated by y-axis movement with a z-axis element.

If the patient is not facing the incoming proton beam, then the description of movements of support elements along the axes change, but the immobilization elements are the same.

An optional camera 3380 is used with the patient immobilization system. The camera views the patient/subject 2130 creating a video image. The image is provided to one or more operators of the charged particle beam system and allows the operators a safety mechanism for determining if the subject has moved or desires to terminate the proton therapy treatment procedure. Based on the video image, the operators optionally suspend or terminate the proton therapy procedure. For example, if the operator observes via the video image that the subject is moving, then the operator has the option to terminate or suspend the proton therapy procedure.

An optional video display or display monitor 3390 is provided to the patient. The video display optionally presents to the patient any of: operator instructions, system instructions, status of treatment, or entertainment.

Motors for positioning the patient positioning constraints 3315, the camera 3380, and/or video display 3390 are preferably mounted above or below the proton transport path 268 or momentary proton scanning path 269.

Respiration control is optionally performed by using the video display. As the patient breathes, internal and external structures of the body move in both absolute terms and in relative terms. For example, the outside of the chest cavity and internal organs both have absolute moves with a breath. In addition, the relative position of an internal organ relative to another body component, such as an outer region of the body, a bone, support structure, or another organ, moves with each breath. Hence, for more accurate and precise tumor targeting, the proton beam is preferably delivered at a point in time where the position of the internal structure or tumor is well defined, such as at the bottom or top of each breath. The video display is used to help coordinate the proton beam delivery with the patient's respiration cycle. For example, the video display optionally displays to the patient a command, such as a hold breath statement, a breathe statement, a countdown indicating when a breath will next need to be held, or a countdown until breathing may resume.

Sitting Patient Positioning/Immobilization

In a second partial immobilization embodiment, the patient is partially restrained in a seated position 3400. The sitting restraint system uses support structures similar to the support structures in the semi-vertical positioning system, described supra, with an exception that the seat support is replaced by a chair and the knee support is not required. The seated restraint system generally retains the adjustable support, rotation about the y-axis, camera, video, and breath control parameters described in the semi-vertical embodiment, described supra.

Figure 34:
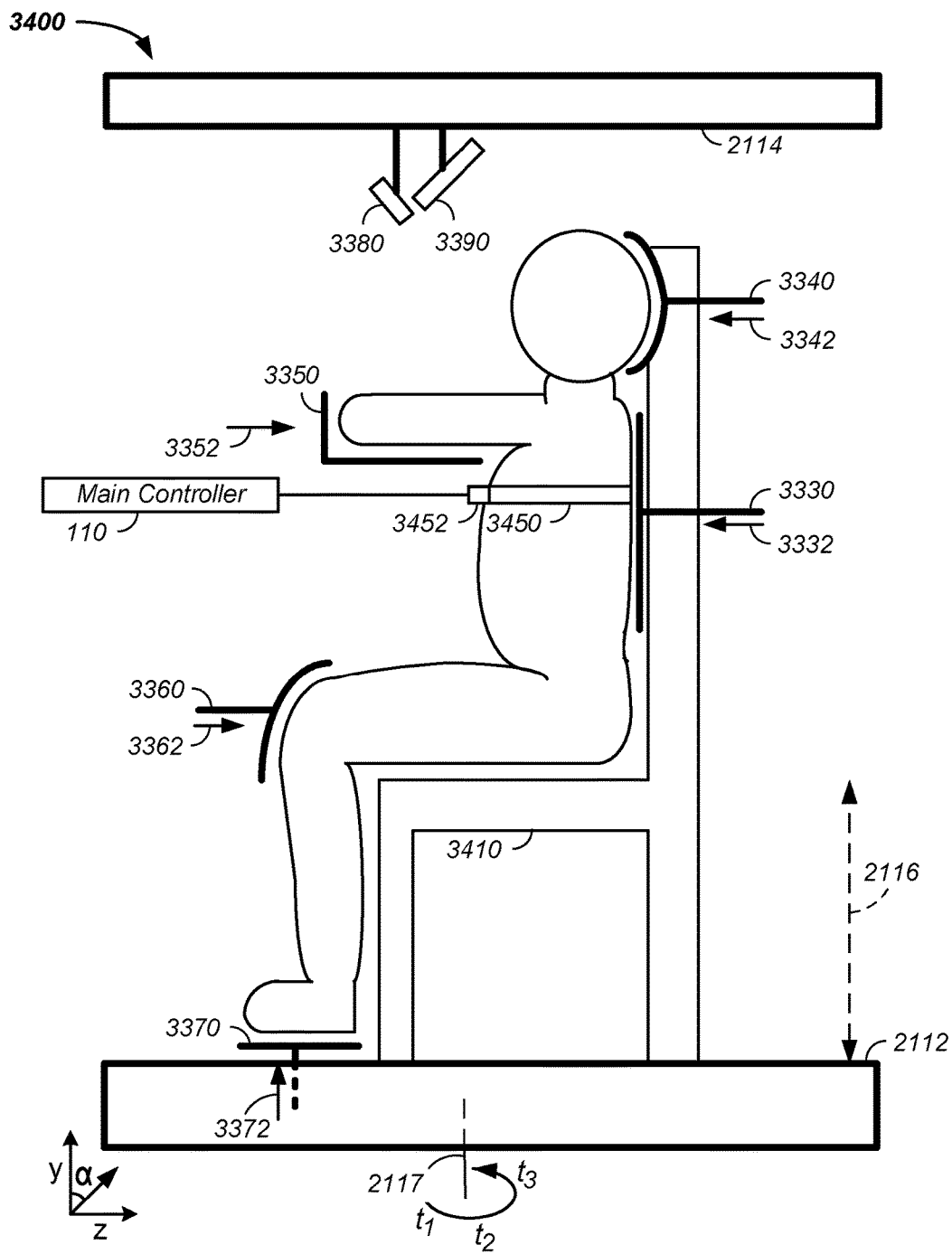
FIG. 34 provides an example of a sitting patient positioning system.

Referring now to FIG. 34, a particular example of a sitting patient semi-immobilization system 3400 is provided. The sitting system is preferably used for treatment of head and/or neck tumors. As illustrated, the patient is positioned in a seated position on a chair 3410 for particle therapy. The patient is further immobilized using any of the: the head support 3340, the back support 3330, the hand support 3350, the knee support 3360, and the foot support 3370. The supports 3320, 3330, 3340, 3350, 3360, 3370 preferably have respective axes of adjustment 3322, 3332, 3342, 3352, 3362, 3372 as illustrated. The chair 3410 is either readily removed to allow for use of a different patient constraint system or adapts under computer control to a new patient position, such as the semi-vertical system.

Laying Patient Positioning/Immobilization

In a third partial immobilization embodiment, the patient is partially restrained in a laying position. Referring now to FIG. 34, the laying restraint system 3500 has support structures that are similar to the support structures used in the sitting positioning system 3400 and semi-vertical positioning system 3300, described supra. In the laying position, optional restraint, support, or partial immobilization elements include one or more of: the head support 3340 and the back support, hip, and shoulder 3330 support. The supports preferably have respective axes of adjustment that are rotated as appropriate for a laying position of the patient. The laying position restraint system generally retains the adjustable supports, rotation about the y-axis, camera, video, and breath control parameters described in the semi-vertical embodiment, described supra.

If the patient is very sick, such as the patient has trouble standing for a period of about one to three minutes required for treatment, then being in a partially supported system can result in some movement of the patient due to muscle strain. In this and similar situations, treatment of a patient in a laying position on a support table 3520 is preferentially used. The support table has a horizontal platform to support the bulk of the weight of the patient. Preferably, the horizontal platform is detachable from a treatment platform. In a laying positioning system 3500, the patient is positioned on a platform 3510, which has a substantially horizontal portion for supporting the weight of the body in a horizontal position. Optional hand grips are used, described infra. In one embodiment, the platform 3510 affixes relative to the table 3520 using a mechanical stop or lock element 3530 and matching key element 3535 and/or the patient 2130 is aligned or positioned relative to a placement element 3560.

Additionally, upper leg support 3544, lower leg support 3540, and/or arm support 3550 elements are optionally added to raise, respectively, an arm or leg out of the proton beam path 269 for treatment of a tumor in the torso or to move an arm or leg into the proton beam path 269 for treatment of a tumor in the arm or leg. This increases proton delivery efficiency, as described supra. The leg supports 3540, 3544 and arm support 3550 are each optionally adjustable along support axes or arcs 3542, 3546, 3552. One or more leg support elements are optionally adjustable along an arc to position the leg into the proton beam path 269 or to remove the leg from the proton beam path 269, as described infra. An arm support element is preferably adjustable along at least one arm adjustment axis or along an arc to position the arm into the proton beam path 269 or to remove the arm from the proton beam path 269, as described infra.

Preferably, the patient is positioned on the platform 3510 in an area or room outside of the proton beam path 268 and is wheeled or slid into the treatment room or proton beam path area. For example, the patient is wheeled into the treatment room on a gurney where the top of the gurney, which is the platform, detaches and is positioned onto a table. The platform is preferably lifted onto the table or slid onto the table so that the gurney or bed need not be lifted onto the table.

The semi-vertical patient positioning system 3300 and sitting patient positioning system 3400 are preferentially used to treatment of tumors in the head or torso due to efficiency. The semi-vertical patient positioning system 3300, sitting patient positioning system 3400, and laying patient positioning system 3500 are all usable for treatment of tumors in the patient's limbs.

Support System Elements

Positioning constraints 3315 include all elements used to position the patient, such as those described in the semi-vertical positioning system 3300, sitting positioning system 3400, and laying positioning system 3500. Preferably, positioning constraints or support system elements are aligned in positions that do not impede or overlap the proton beam path 269. However, in some instances the positioning constraints are in the proton beam path 269 during at least part of the time of treatment of the patient. For instance, a positioning constraint element may reside in the proton beam path 269 during part of a time period where the patient is rotated about the y-axis during treatment. In cases or time periods that the positioning constraints or support system elements are in the proton beam path, then an upward adjustment of proton beam energy is preferably applied that increases the proton beam energy to offset the positioning constraint element impedance of the proton beam. This time period and energy is a function of rotational orientation of the patient. In one case, the proton beam energy is increased by a separate measure of the positioning constraint element impedance determined during a reference scan of the positioning constraint system element or set of reference scans of the positioning constraint element as a function of rotation about the y-axis.

For clarity, the positioning constraints 3315 or support system elements are herein described relative to the semi-vertical positioning system 3300; however, the positioning elements and descriptive x-, y-, and z-axes are adjustable to fit any coordinate system, to the sitting positioning system 3400, or the laying positioning system 3500.

An example of a head support system is described to support, align, and/or restrict movement of a human head. The head support system preferably has several head support elements including any of: a back of head support, a right of head alignment element, and a left of head alignment element. The back of head support element is preferably curved to fit the head and is optionally adjustable along a head support axis, such as along the z-axis. Further, the head supports, like the other patient positioning constraints, is preferably made of a semi-rigid material, such as a low or high density foam, and has an optional covering, such as a plastic or leather. The right of head alignment element and left of head alignment elements or head alignment elements, are primarily used to semi-constrain movement of the head or to fully immobilize the head. The head alignment elements are preferably padded and flat, but optionally have a radius of curvature to fit the side of the head. The right and left head alignment elements are preferably respectively movable along translation axes to make contact with the sides of the head. Restricted movement of the head during proton therapy is important when targeting and treating tumors in the head or neck. The head alignment elements and the back of head support element combine to restrict tilt, rotation or yaw, roll and/or position of the head in the x-, y-, z-axes coordinate system.

Figure 36:
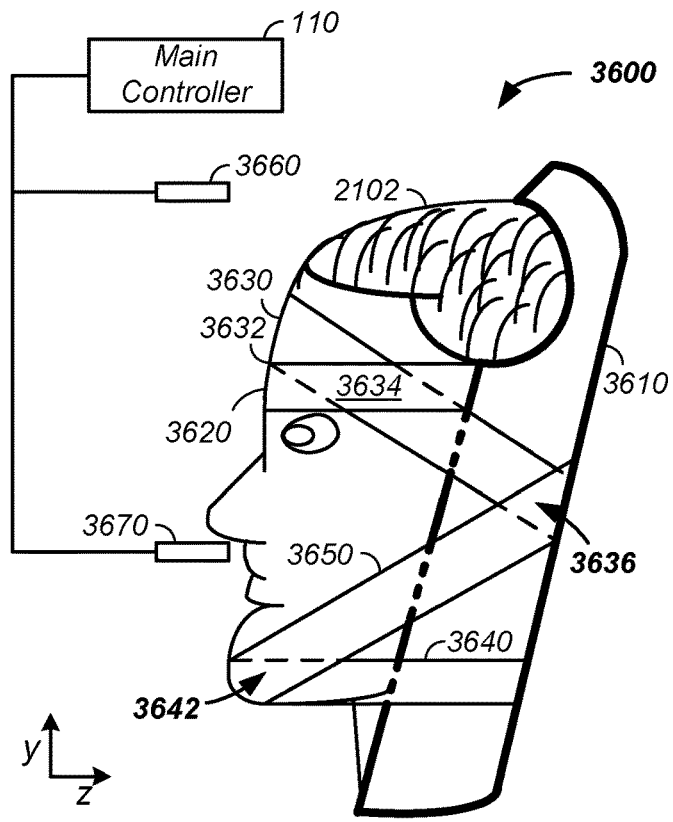
FIG. 36 illustrates a head restraint system.

Referring now to FIG. 36 another example of a head support system 3600 is described for positioning and/or restricting movement of a human head 2102 during proton therapy of a solid tumor in the head or neck. In this system, the head is restrained using 1, 2, 3, 4, or more straps or belts, which are preferably connected or replaceably connected to a back of head support element 3610. In the example illustrated, a first strap 3620 pulls or positions the forehead to the head support element 3610, such as by running predominantly along the z-axis. Preferably a second strap 3630 works in conjunction with the first strap 3620 to prevent the head from undergoing tilt, yaw, roll or moving in terms of translational movement on the x-, y-, and z-axes coordinate system. The second strap 3630 is preferably attached or replaceable attached to the first strap 3620 at or about: (1) a forehead position 3632; (2) at a position on one or both sides of the head 3634; and/or (3) at or about a position on the support element 3636. A third strap 3640 preferably orientates the chin of the subject relative to the support element 3610 by running dominantly along the z-axis. A fourth strap 3650 preferably runs along a predominantly y- and z-axes to hold the chin relative to the head support element 3610 and/or proton beam path. The third 3640 strap preferably is attached to or is replaceably attached to the fourth strap 3650 during use at or about the patient's chin position 3642. The second strap 3630 optionally connects 3636 to the fourth strap 3650 at or about the support element 3610. The four straps 3620, 3630, 3640, 3650 are illustrative in pathway and interconnection. Any of the straps optionally hold the head along different paths around the head and connect to each other in separate fashion. Naturally, a given strap preferably runs around the head and not just on one side of the head. Any of the straps 3620, 3630, 3640, and 3650 are optionally used independently or in combinations and permutations with the other straps. The straps are optionally indirectly connected to each other via a support element, such as the head support element 3610. The straps are optionally attached to the head support element 3610 using hook and loop technology, a buckle, or fastener. Generally, the straps combine to control position, front-to-back movement of the head, side-to-side movement of the head, tilt, yaw, roll, and/or translational position of the head.

The straps are preferably of known impedance to proton transmission allowing a calculation of peak energy release along the z-axis to be calculated. For example, adjustment to the Bragg peak energy is made based on the slowing tendency of the straps to proton transport.

Figure 37:
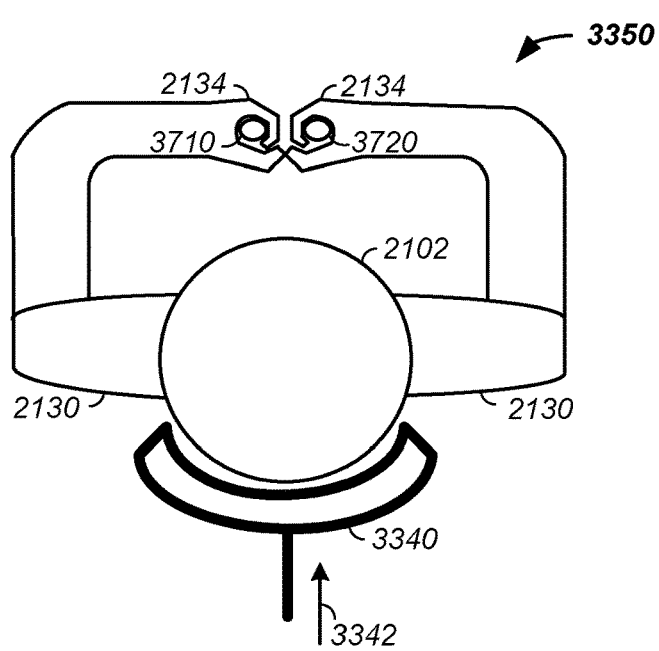
FIG. 37 illustrates hand and head supports.

Referring now to FIG. 37, still another example of a head support system 3340 is described. The head support 3340 is preferably curved to fit a standard or child sized head. The head support 3340 is optionally adjustable along a head support axis 3342. Further, the head supports, like the other patient positioning constraints, is preferably made of a semi-rigid material, such as a low or high density foam, and has an optional covering, such as a plastic or leather.

Elements of the above described head support, head positioning, and head immobilization systems are optionally used separately or in combination.

Still referring to FIG. 37, an example of the arm support 3350 is further described. The arm support preferably has a left hand grip 3710 and a right hand grip 3720 used for aligning the upper body of the patient 2130 through the action of the patient 2130 gripping the left and right hand grips 3710, 3720 with the patient's hands 2134. The left and right hand grips 3710, 3720 are preferably connected to the arm support 3350 that supports the mass of the patient's arms. The left and right hand grips 3710, 3720 are preferably constructed using a semi-rigid material. The left and right hand grips 3710, 3720 are optionally molded to the patient's hands to aid in alignment. The left and right hand grips optionally have electrodes, as described supra.

Patient Respiration Monitoring

Preferably, the patient's respiration pattern is monitored. When a subject or patient 2130 is breathing many portions of the body move with each breath. For example, when a subject breathes the lungs move as do relative positions of organs within the body, such as the stomach, kidneys, liver, chest muscles, skin, heart, and lungs. Generally, most or all parts of the torso move with each breath. Indeed, the inventors have recognized that in addition to motion of the torso with each breath, various motion also exists in the head and limbs with each breath. Motion is to be considered in delivery of a proton dose to the body as the protons are preferentially delivered to the tumor and not to surrounding tissue. Motion thus results in an ambiguity in where the tumor resides relative to the beam path. To partially overcome this concern, protons are preferentially delivered at the same point in each of a series of respiration cycles.

Initially a rhythmic pattern of breathing of a subject is determined. The cycle is observed or measured. For example, an X-ray beam operator or proton beam operator can observe when a subject is breathing or is between breaths and can time the delivery of the protons to a given period of each breath. Alternatively, the subject is told to inhale, exhale, and/or hold their breath and the protons are delivered during the commanded time period.

Preferably, one or more sensors are used to determine the respiration cycle of the individual. Two examples of a respiration monitoring system 4010 are provided: (1) a thermal monitoring system and (2) a force monitoring system.

Figure 35:
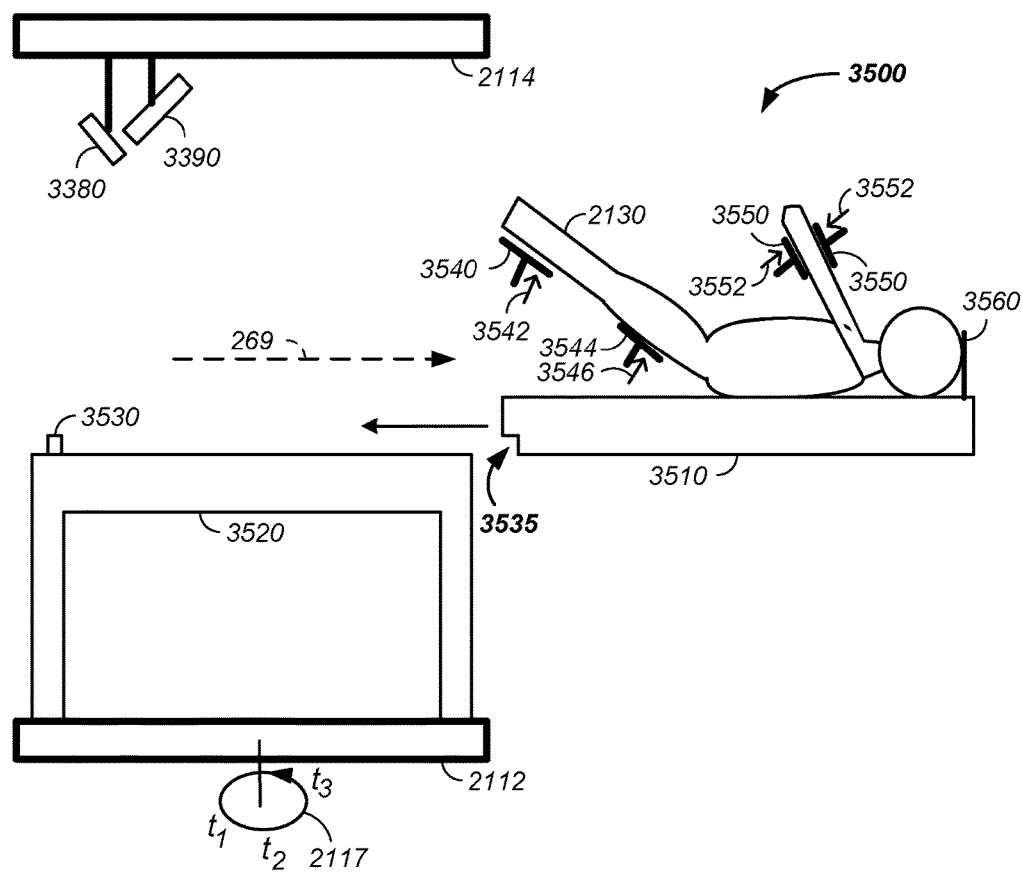
FIG. 35 illustrates a laying patient positioning system.

Referring again to FIG. 35, a first example of the thermal respiration monitoring system is provided. In the thermal respiration monitoring system, a sensor is placed by the nose and/or mouth of the patient. As the jaw of the patient is optionally constrained, as described supra, the thermal respiration monitoring system is preferably placed by the patient's nose exhalation path. To avoid steric interference of the thermal sensor system components with proton therapy, the thermal respiration monitoring system is preferably used when treating a tumor not located in the head or neck, such as a when treating a tumor in the torso or limbs. In the thermal monitoring system, a first thermal resistor 3670 is used to monitor the patient's respiration cycle and/or location in the patient's respiration cycle. Preferably, the first thermal resistor 3670 is placed by the patient's nose, such that the patient exhaling through their nose onto the first thermal resistor 3670 warms the first thermal resistor 3670 indicating an exhale. Preferably, a second thermal resistor 3660 operates as an environmental temperature sensor. The second thermal resistor 3660 is preferably placed out of the exhalation path of the patient but in the same local room environment as the first thermal resistor 3670. Generated signal, such as current from the thermal resistors 3670, 3660, is preferably converted to voltage and communicated with the main controller 110 or a subcontroller of the main controller. Preferably, the second thermal resistor 3660 is used to adjust for the environmental temperature fluctuation that is part of a signal of the first thermal resistor 3670, such as by calculating a difference between the values of the thermal resistors 3670, 3660 to yield a more accurate reading of the patient's respiration cycle.

Referring again to FIG. 34, a second example of a monitoring system is provided. In an example of a force respiration monitoring system, a sensor is placed by the torso. To avoid steric interference of the force sensor system components with proton therapy, the force respiration monitoring system is preferably used when treating a tumor located in the head, neck, or limbs. In the force monitoring system, a belt or strap 3450 is placed around an area of the patient's torso that expands and contracts with each respiration cycle of the patient. The belt 3450 is preferably tight about the patient's chest and is flexible. A force meter 3452 is attached to the belt and senses the patients respiration pattern. The forces applied to the force meter 3452 correlate with periods of the respiration cycle. The signals from the force meter 3452 are preferably communicated with the main controller 110 or a sub-controller of the main controller.

Coordinated Charged Particle Beam Control

In this section, charged particle beam control systems, described supra, are coordinated for cancer therapy.

Positioning, Imaging, and Irradiation

Figure 38:
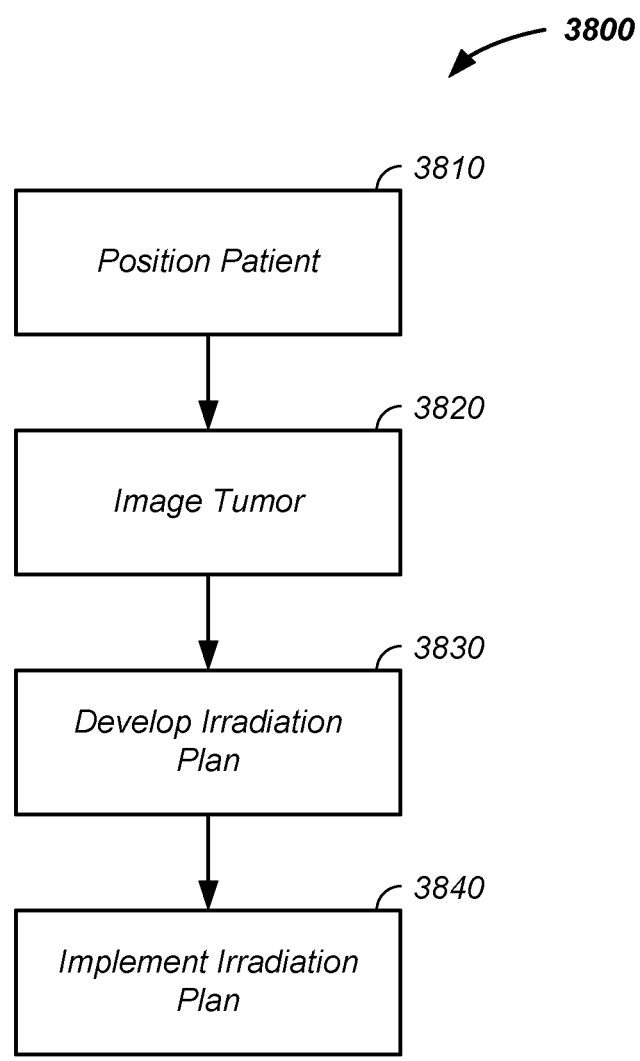
FIG. 38 provides a method of positioning, imaging, and irradiating a tumor.

Referring now to FIG. 38, a method of cancer therapy is provided. In this method, the patient is first positioned 3810, then the tumor is imaged 3820, subsequently a charged particle irradiation plan is developed 3830, and then the charged particle irradiation plan is implemented 3840. Further examples of the steps provided in FIG. 38 are described, infra, along with additional optional steps. For example, the positioning, imaging, and irradiation steps are optionally integrated with patient translation control, patient rotation control, and/or patient respiration control. Additionally, any of the steps described herein are optionally coordinated with charged particle beam generation, acceleration, extraction, and/or delivery. Additionally, any of the steps are optionally coordinated with x-, y-axis beam trajectory control, delivered energy control, delivered intensity control, timing of charged particle delivery, and/or distribution of radiation striking healthy tissue.

Tumor Imaging

Figure 39:
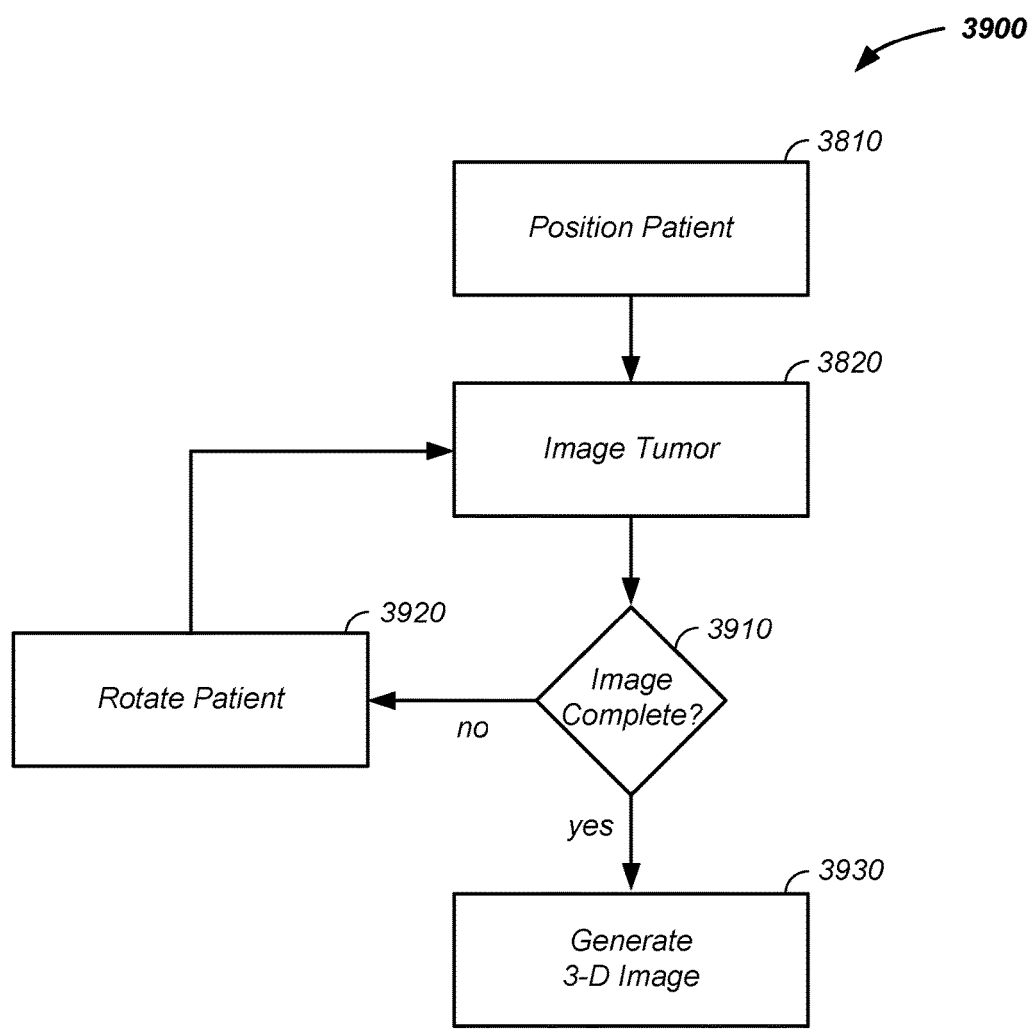
FIG. 39 provides a method of imaging a tumor with rotation of the patient.

Referring now to FIG. 39, a method of tumor imaging is provided. In a first step, the patient is positioned 3810, such as with the patient immobilization and/or positioning systems described supra. Subsequently, the tumor is imaged 3820, such as with the imaging/X-ray system described supra. Preferably, each image is a 2-dimensional image. If the image is not complete 3910, then the patient is rotated 3920, such as with the multi-field irradiation rotatable platform described supra. For instance, the image is collected with rotation of the patient about the y-axis 2117. After rotation of n degrees of rotation of the patient 2130, where n is about ½, 1, 2, 3, 5, 10, or 20 degrees, another image is collected 3820. The imaging 3820 and rotation 3920 processes are repeated until the tumor 2120 is suitably imaged. A 3-dimensional image is created 3930 using the two-dimensional images collected as a function of patient rotation.

Respiration Control

Figure 40:
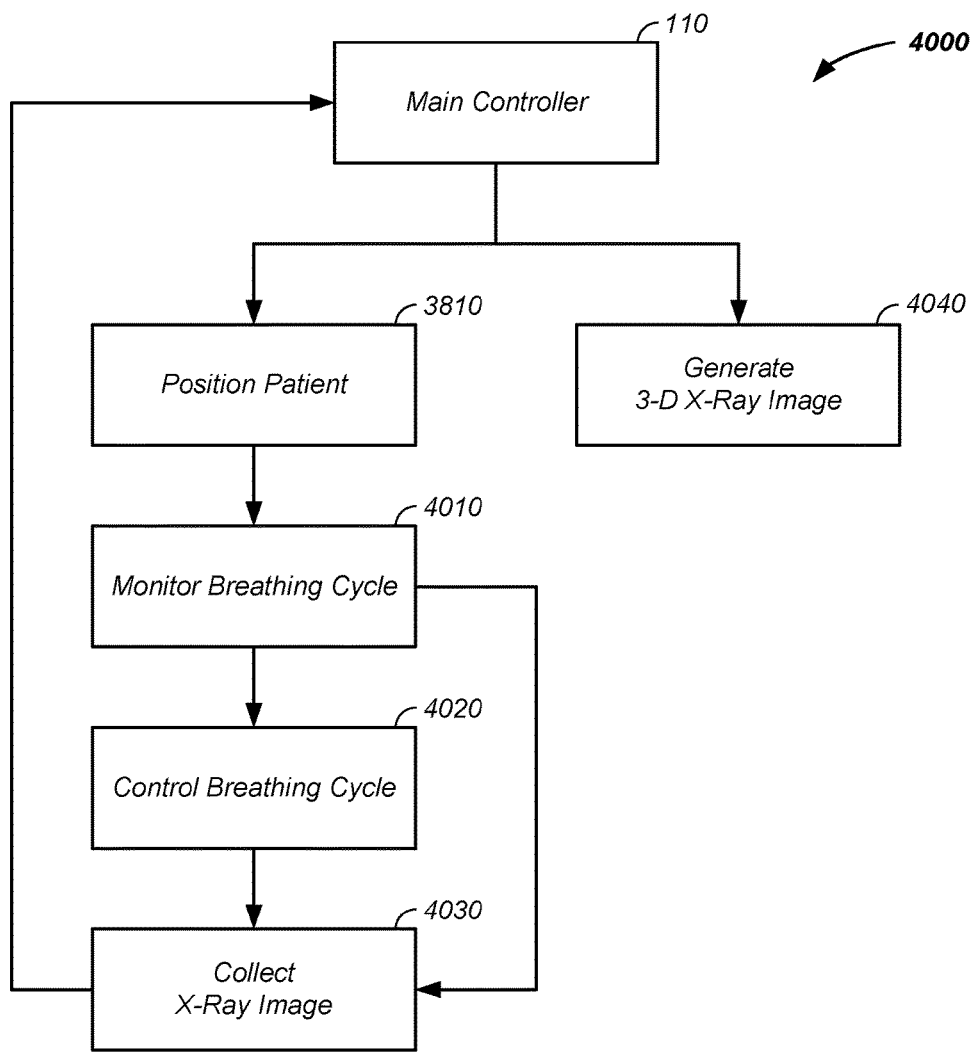
FIG. 40 provides a method of coordinating X-ray collection with patient respiration.

Referring now to FIG. 40, a patient is positioned 3810 and once the rhythmic pattern of the subject's breathing or respiration cycle is determined 4010, a signal is optionally delivered to the patient, such as via the display monitor 3390, to more precisely control the breathing frequency 4020. For example, the display screen 3390 is placed in front of the patient and a message or signal is transmitted to the display screen 3390 directing the subject when to hold their breath and when to breathe. Typically, a respiration control module uses input from one or more of the respiration sensors. For example, the input is used to determine when the next breath exhale is to complete. At the bottom of the breath, the control module displays a hold breath signal to the subject, such as on a monitor, via an oral signal, digitized and automatically generated voice command, or via a visual control signal. Preferably, a display monitor 3390 is positioned in front of the subject and the display monitor displays breathing commands to the subject. Typically, the subject is directed to hold their breath for a short period of time, such as about ½, 1, 2, 3, 5, or 10 seconds. The period of time the breath is held is preferably synchronized to the delivery time of the proton beam to the tumor, which is about ½, 1, 2, or 3 seconds. While delivery of the protons at the bottom of the breath is preferred, protons are optionally delivered at any point in the respiration cycle, such as upon full inhalation. Delivery at the top of the breath or when the patient is directed to inhale deeply and hold their breath by the respiration control module is optionally performed as at the top of the breath the chest cavity is largest and for some tumors the distance between the tumor and surrounding tissue is maximized or the surrounding tissue is rarefied as a result of the increased volume. Hence, protons hitting surrounding tissue is minimized. Optionally, the display screen tells the subject when they are about to be asked to hold their breath, such as with a 3, 2, 1, second countdown so that the subject is aware of the task they are about to be asked to perform.

X-Ray Synchronization with Patient Respiration

In one embodiment, X-ray images are collected in synchronization with patient respiration. The synchronization enhances X-ray image clarity by removing position ambiguity due to the relative movement of body constituents during a patient respiration cycle.

In a second embodiment, an X-ray system is orientated to provide X-ray images of a patient in the same orientation as viewed by a proton therapy beam, is synchronized with patient respiration, is operable on a patient positioned for proton therapy, and does not interfere with a proton beam treatment path. Preferably, the synchronized system is used in conjunction with a negative ion beam source, synchrotron, and/or targeting method and apparatus to provide an X-ray timed with patient respiration. Preferably, X-ray images are collected immediately prior to and/or concurrently with particle beam therapy irradiation to ensure targeted and controlled delivery of energy relative to a patient position resulting in efficient, precise, and/or accurate in-vivo treatment of a solid cancerous tumor with minimization of damage to surrounding healthy tissue.

An X-ray delivery control algorithm is used to synchronize delivery of the X-rays to the patient 2130 within a given period of each breath, such as at the top or bottom of a breath, and/or when the subject is holding their breath. For clarity of combined X-ray images, the patient is preferably both accurately positioned and precisely aligned relative to the X-ray beam path 3070. The X-ray delivery control algorithm is preferably integrated with the respiration control module. Thus, the X-ray delivery control algorithm knows when the subject is breathing, where in the respiration cycle the subject is, and/or when the subject is holding their breath. In this manner, the X-ray delivery control algorithm delivers X-rays at a selected period of the respiration cycle. Accuracy and precision of patient alignment allow for (1) more accurate and precise location of the tumor 2120 relative to other body constituents and (2) more accurate and precise combination of X-rays in generation of a 3-dimensional X-ray image of the patient 2130 and tumor 2120.

Referring again to FIG. 40, an example of generating an X-ray image of the patient 2130 and tumor 2120 using the X-ray generation device 3000 or 3-dimensional X-ray generation device 3000 as a known function of time of the patient's respiration cycle is provided. In one embodiment, as a first step the main controller 110 instructs, monitors, and/or is informed of patient positioning 3810. In a first example of patient positioning 3810, the automated patient positioning system, described supra, under main controller 110 control, is used to align the patient 2130 relative to the X-ray beam path 3070. In a second example of patient positioning, the main controller 110 is told via sensors or human input that the patient 2130 is aligned. In a second step, patient respiration is then monitored 4010, as described infra. As a first example of respiration monitoring, an X-ray is collected 4030 at a known point in the patient respiration cycle. In a second example of respiration monitoring, the patient's respiration cycle is first controlled in a third step of controlling patient respiration 4020 and then as a fourth step an X-ray is collected 4030 at a controlled point in the patient respiration cycle. Preferably, the cycle of patient positioning 3810, patient respiration monitoring 4010, patient respiration control 4020, and collecting an X-ray 4030 is repeated with different patient positions. For example, the patient 2130 is rotated about an axis 2117 and X-rays are collected as a function of the rotation. In a fifth step, a 3-dimensional X-ray image 4040 is generated of the patient 2130, tumor 2120, and body constituents about the tumor using the collected X-ray images, such as with the 3-dimensional X-ray generation device 3000, described supra. The patient respiration monitoring and control steps are further described, infra.

An X-ray timed with patient respiration where the X-ray is preferably collected immediately prior to and/or concurrently with particle beam therapy irradiation to ensure targeted and controlled delivery of energy relative to a patient position resulting in efficient, precise, and/or accurate treatment of a solid cancerous tumor with minimization of damage to surrounding healthy tissue in a patient using the proton beam position verification system.

Proton Beam Therapy Synchronization with Respiration

In one embodiment, charged particle therapy and preferably multi-field proton therapy is coordinated and synchronized with patient respiration via use of the respiration feedback sensors, described supra, used to monitor and/or control patient respiration. Preferably, the charged particle therapy is performed on a patient in a partially immobilized and repositionable position and the proton delivery to the tumor 2120 is timed to patient respiration via control of charged particle beam injection, acceleration, extraction, and/or targeting methods and apparatus. The synchronization enhances proton delivery accuracy by removing position ambiguity due to the relative movement of body constituents during a patient respiration cycle. Synchrotron control to deliver protons at a desired point in the respiration cycle is described infra.

In a second embodiment, the X-ray system, described supra, is used to provide X-ray images of a patient in the same orientation as viewed by a proton therapy beam and both the X-ray system and the proton therapy beam are synchronized with patient respiration. Again, synchrotron control to deliver protons at a desired point in the respiration cycle is described infra.

A proton delivery control algorithm is used to synchronize delivery of the protons to the tumor within a given period of each breath, such as at the top of a breath, at the bottom of a breath, and/or when the subject is holding their breath. The proton delivery control algorithm is preferably integrated with the respiration control module. Thus, the proton delivery control algorithm knows when the subject is breathing, where in the respiration cycle the subject is, and/or when the subject is holding their breath. The proton delivery control algorithm controls when protons are injected and/or inflected into the synchrotron, when an RF signal is applied to induce an oscillation, as described supra, and when a DC voltage is applied to extract protons from the synchrotron, as described supra. Typically, the proton delivery control algorithm initiates proton inflection and subsequent RF induced oscillation before the subject is directed to hold their breath or before the identified period of the respiration cycle selected for a proton delivery time. In this manner, the proton delivery control algorithm delivers protons at a selected period of the respiration cycle by simultaneously or nearly simultaneously delivering the high DC voltage to the second pair of plates, described supra, which results in extraction of the protons from the synchrotron and subsequent delivery to the subject at the selected time point. Since the period of acceleration of protons in the synchrotron is constant or known for a desired energy level of the proton beam, the proton delivery control algorithm is used to set an AC RF signal that matches the respiration cycle or directed respiration cycle of the subject.

The above described charged particle therapy elements are combined in combinations and/or permutations in developing and implementing a tumor treatment plan, described infra.

Proton Beam Generation, Injection, Acceleration, Extraction, and Delivery

Figure 41:
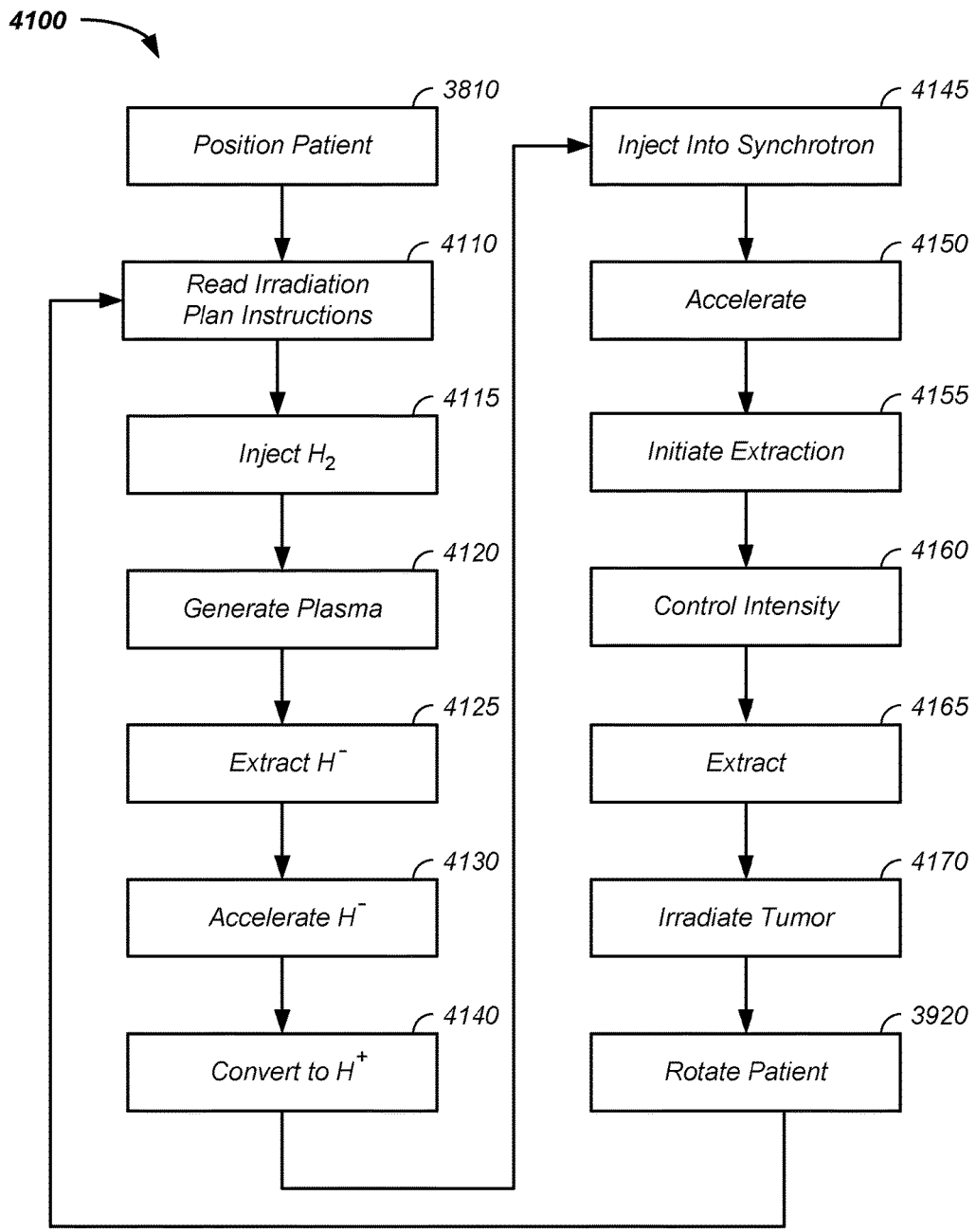
FIG. 41 provides a method of charged particle beam control.

Referring now to FIG. 41, an example of implementation of the irradiation plan 3840 is provided. The multi-axis and/or multi-field charged particle cancer therapy system elements described herein are preferably coordinated with charged particle delivery 4100. After patient positioning 3810 and reading the irradiation plan instructions 4110, hydrogen is injected 4115 into the negative ion source 310, plasma is generated 4120, a negative ion is extracted 4125, and the negative ion is accelerated 4130, converted into a positive ion 4140, and injected into the synchrotron 4145. Subsequently, the positive ion is accelerated 4150, extraction is initiated 4155, intensity of the irradiation beam is controlled 4160, extraction of the charged particle beam is performed 4165, and the tumor is irradiated 4170. Preferably, one or more elements of the charged particle delivery 4100 system are timed with patient respiration. After tumor irradiation 4170, the patient is preferably rotated 3920 and the irradiation sequence is repeated yielding multi-field irradiation of the tumor 2120. The entire sequence is optionally performed using the intensity modulated 3-dimensional scanning system 2800, described supra.

Multi-Axis Charged Particle Irradiation

Figure 42:
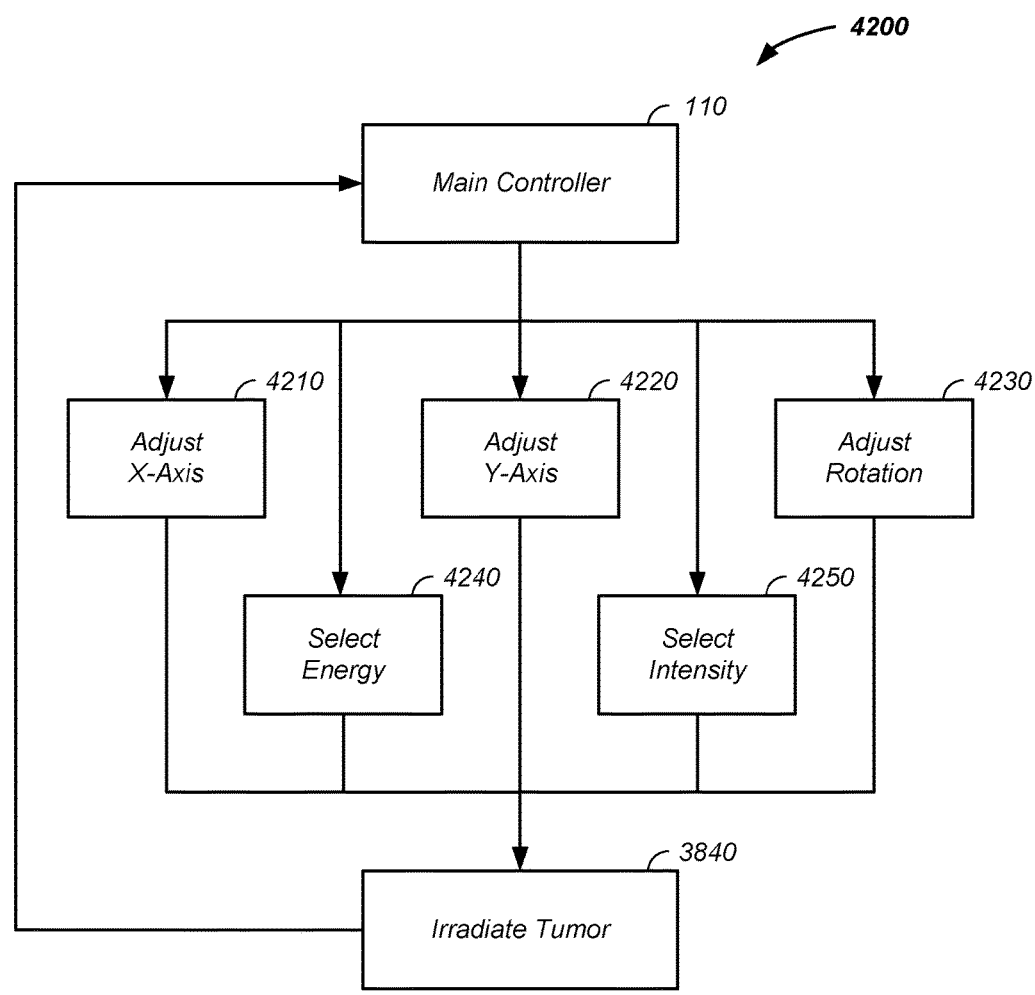
FIG. 42 provides a method of multi-axis charged particle beam irradiation control.

Referring now to FIG. 42, another example of implementation of the irradiation plan 3840 is provided. In this example, a multi-axis charged particle beam therapy system is provided, where multi-axis refers to independent control of: x-axis beam control, y-axis beam control, delivered beam energy, and/or delivered beam intensity. The multi-axis control is preferably implemented with multi-field charge particle irradiation, such as via use of independent control of rotation and/or translation of the patient. In this example, the main controller 110 independently adjusts x-axis targeting of the proton beam 4210, y-axis targeting of the proton beam 4220, rotational position of the patient 4230, delivered energy of the proton beam 4240, and/or delivered intensity of the proton beam in the step of irradiating the tumor 3840. The process is optionally repeated or iterated using a continuously irradiating and scanning charged particle irradiation system as described using the 3-dimensional scanning system 2800.

Developing and Implementing a Tumor Irradiation Plan

A series of steps are performed to design and execute a radiation treatment plan for treating a tumor 2120 in a patient 2130. The steps include one or more of:
  positioning and immobilizing the patient;
  recording the patient position;
  monitoring patient respiration;
  controlling patient respiration;
  collecting multi-field images of the patient to determine tumor location relative to body constituents;
  developing a radiation treatment plan;
  repositioning the patient;
  verifying tumor location; and
  irradiating the tumor.

In this section, an overview of developing the irradiation plan and subsequent implementation of the irradiation plan is initially presented, the individual steps are further described, and a more detailed example of the process is then described.

Figure 43:
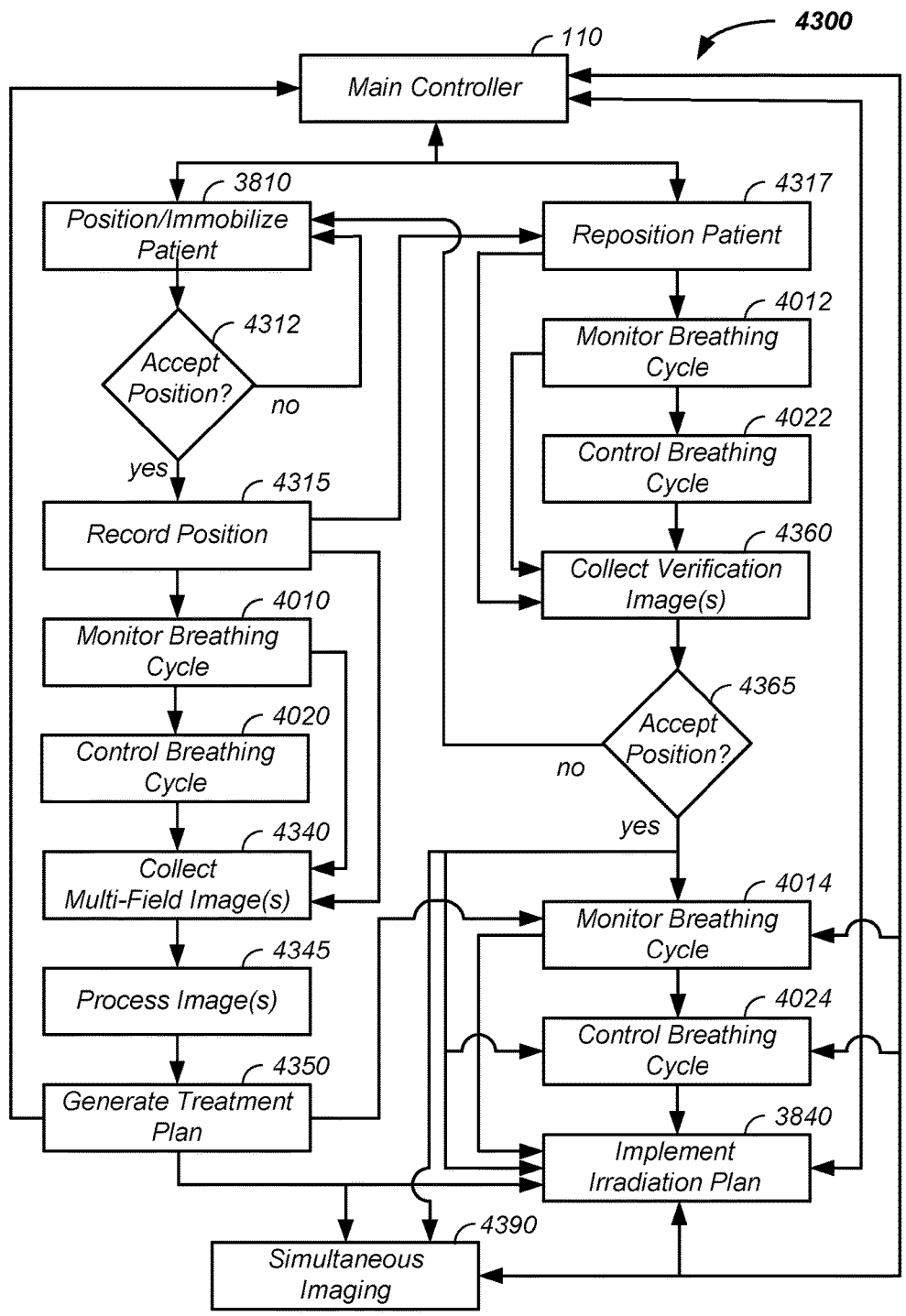
FIG. 43 illustrates a patient positioning, immobilization, and repositioning system.

Referring now to FIG. 43, an overview of a system for development of an irradiation plan and subsequent implementation of the irradiation plan 4300 is provided. Preferably, all elements of the positioning, respiration monitoring, imaging, and tumor irradiation system 4300 are under main controller 110 control.

Initially, the tumor containing volume of the patient 2130 is positioned and immobilized 3810 in a controlled and reproducible position. The process of positioning and immobilizing 3810 the patient 2310 is preferably iterated 4312 until the position is accepted. The position is preferably digitally recorded 4315 and is later used in a step of computer controlled repositioning of the patient 4317 in the minutes or seconds prior to implementation of the irradiation element 3840 of the tumor treatment plan. The process of positioning the patient in a reproducible fashion and reproducibly aligning the patient 2310 to the controlled position is further described, infra.

Subsequent to patient positioning 3810, the steps of monitoring 4010 and preferably controlling 4020 the respiration cycle of the patient 2130 are preferably performed to yield more precise positioning of the tumor 2120 relative to other body constituents, as described supra. Multi-field images of the tumor are then collected 4340 in the controlled, immobilized, and reproducible position. For example, multi-field X-ray images of the tumor 2120 are collected using the X-ray source proximate the proton beam path, as described supra. The multi-field images are optionally from three or more positions and/or are collected while the patient is rotated, as described supra.

At this point the patient 2130 is either maintained in the treatment position or is allowed to move from the controlled treatment position while an oncologist processes the multi-field images 4345 and generates a tumor treatment plan 4350 using the multi-field images. Optionally, the tumor irradiation plan is implemented 3840 at this point in time.

Typically, in a subsequent treatment center visit, the patient 2130 is repositioned 4317. Preferably, the patient's respiration cycle is again monitored 4012 and/or controlled 4022, such as via use of the thermal monitoring respiration sensors, force monitoring respiration sensor, and/or via commands sent to the display monitor 3390, described supra. Once repositioned, verification images are collected 4360, such as X-ray location verification images from 1, 2, or 3 directions. For example, verification images are collected with the patient facing the proton beam and at rotation angles of 90, 180, and 270 degrees from this position. At this point, comparing the verification images to the original multi-field images used in generating the treatment plan, the algorithm or preferably the oncologist determines if the tumor 2120 is sufficiently repositioned 4365 relative to other body parts to allow for initiation of tumor irradiation using the charged particle beam. Essentially, the step of accepting the final position of the patient 4365 is a safety feature used to verify that that the tumor 2120 in the patient 2130 has not shifted or grown beyond set specifications. At this point the charged particle beam therapy commences 3840. Preferably the patient's respiration is monitored 4014 and/or controlled 4024, as described supra, prior to commencement of the charged particle beam treatment 3840.

Optionally, simultaneous X-ray imaging 4390 of the tumor 2120 is performed during the multi-field proton beam irradiation procedure and the main controller 110 uses the X-ray images to adapt the radiation treatment plan in real-time to account for small variations in movement of the tumor 2120 within the patient 2130.

Herein the steps of monitoring 4010, 4012, 4014 and controlling 4020, 4022, 4024 the patient's respiration are optional, but preferred. The steps of monitoring and controlling the patient's respiration are performed before and/or during the multi-filed imaging 4340, position verification 4360, and/or tumor irradiation 3840 steps. The patient positioning 3810 and patient repositioning 4317 steps are further described, infra.

Coordinated Charged Particle Acceleration and Respiration Rate

In yet another embodiment, the charged particle accelerator is synchronized to the patient's respiration cycle. More particularly, synchrotron acceleration cycle usage efficiency is enhanced by adjusting the synchrotron's acceleration cycle to correlate with a patient's respiration rate. Herein, efficiency refers to the duty cycle, the percentage of acceleration cycles used to deliver charged particles to the tumor, and/or the fraction of time that charged particles are delivered to the tumor from the synchrotron. The system senses patient respiration and controls timing of negative ion beam formation, injection of charged particles into a synchrotron, acceleration of the charged particles, and/or extraction to yield delivery of the particles to the tumor at a predetermine period of the patient's respiration cycle. Preferably, one or more magnetic fields in the synchrotron 130 are stabilized through use of a feedback loop, which allows rapid changing of energy levels and/or timing of extraction from pulse to pulse. Further, the feedback loop allows control of the acceleration/extraction to correlate with a changing patient respiration rate. Independent control of charged particle energy and intensity is maintained during the timed irradiation therapy. Multi-field irradiation ensures efficient delivery of Bragg peak energy to the tumor while spreading ingress energy about the tumor.

In one example, a sensor, such as the first thermal sensor 3670 or the second thermal sensor 3660, is used to monitor a patient's respiration. A controller, such as the main controller 110, then controls charged particle formation and delivery to yield a charged particle beam delivered at a determined point or duration period of the respiration cycle, which ensures precise and accurate delivery of radiation to a tumor that moves during the respiration process. Optional charged particle therapy elements controlled by the controller include the injector 120, accelerator 132, and/or extraction 134 system. Elements optionally controlled in the injector system 120 include: injection of hydrogen gas into a negative ion source 310, generation of a high energy plasma within the negative ion source, filtering of the high energy plasma with a magnetic field, extracting a negative ion from the negative ion source, focusing the negative ion beam 319, and/or injecting a resulting positive ion beam 262 into the synchrotron 130. Elements optionally controlled in the accelerator 132 include: accelerator coils, applied magnetic fields in turning magnets, and/or applied current to correction coils in the synchrotron. Elements optionally controlled in the extraction system 134 include: radio-frequency fields in an extraction element and/or applied fields in an extraction process. By using the respiration sensor to control delivery of the charged particle beam to the tumor during a set period of the respiration cycle, the period of delivery of the charged particle to the tumor is adjustable to a varying respiration rate. Thus, if the patient breathes faster, the charged particle beam is delivered to the tumor more frequently and if the patient breathes slower, then the charged particle beam is delivered to the tumor less frequently. Optionally, the charged particle beam is delivered to the tumor with each breath of the patient regardless of the patient's changing respiration rate. This lies in stark contrast with a system where the charged particle beam delivers energy at a fixed time interval and the patient must adjust their respiration rate to match the period of the accelerator delivering energy and if the patient's respiration rate does not match the fixed period of the accelerator, then that accelerator cycle is not delivered to the tumor and the acceleration usage efficiency is reduced.

Typically, in an accelerator the current is stabilized. A problem with current stabilized accelerators is that the magnets used have memories in terms of both magnitude and amplitude of a sine wave. Hence, in a traditional system, in order to change the circulation frequency of the charged particle beam in a synchrotron, slow changes in current must be used. However, in a second example, the magnetic field controlling the circulation of the charged particles about the synchrotron is stabilized. The magnetic field is stabilized through use of: (1) magnetic field sensors 1650 sensing the magnetic field about the circulating charged particles and (2) a feedback loop through a controller or main controller 110 controlling the magnetic field about the circulating charged particles. The feedback loop is optionally used as a feedback control to the first winding coil 1250 and the second winding coil 1260. However, preferably the feedback loop is used to control the correction coils 1510, 1520, described supra. With the use of the feedback loop described herein using the magnetic field sensors, the frequency and energy level of the synchrotron are rapidly adjustable and the problem is overcome. Further, the use of the smaller correction coils 1510, 1520 allows for rapid adjustment of the accelerator compared to the use of the larger winding coils 1250, 1260, described supra. More particularly, the feedback control allows an adjustment of the accelerator energy from pulse to pulse in the synchrotron 130.

In this section, the first example yielded delivery of the charged particle beam during a particular period of the patient's respiration cycle even if the patient's respiration period is varying. In this section, the second example used a magnetic field sensor 1650 and a feedback loop to the correction coils 1510, 1520 to rapidly adjust the energy of the accelerator from pulse to pulse. In a third example, the respiration sensor of the first example is combined with the magnetic field sensor of the second example to control both the timing of the delivery of the charged particle beam from the accelerator and the energy of the charged particle beam from the accelerator. More particularly, the timing of the charged particle delivery is controlled using the respiration sensor, as described supra, and the energy of the charged particle beam is controlled using the magnetic field sensors and feedback loop, as described supra. Still more particularly, a magnetic field controller, such as the main controller 110, takes the input from the respiration sensor and uses the input as: (1) a feedback control to the magnetic fields controlling the circulating charged particles energy and (2) as a feedback control to time the pulse of the charged particle accelerator to the respiration cycle of the patient. This combination allows delivery of the charged particle beam to the tumor with each breath of the patient even if the breathing rate of the patient varies. In this manner, the accelerator efficiency is increased as the cancer therapy system does not need to lose cycles when the patient's breathing is not in phase with the synchrotron charged particle generation rate.

Figure 44:
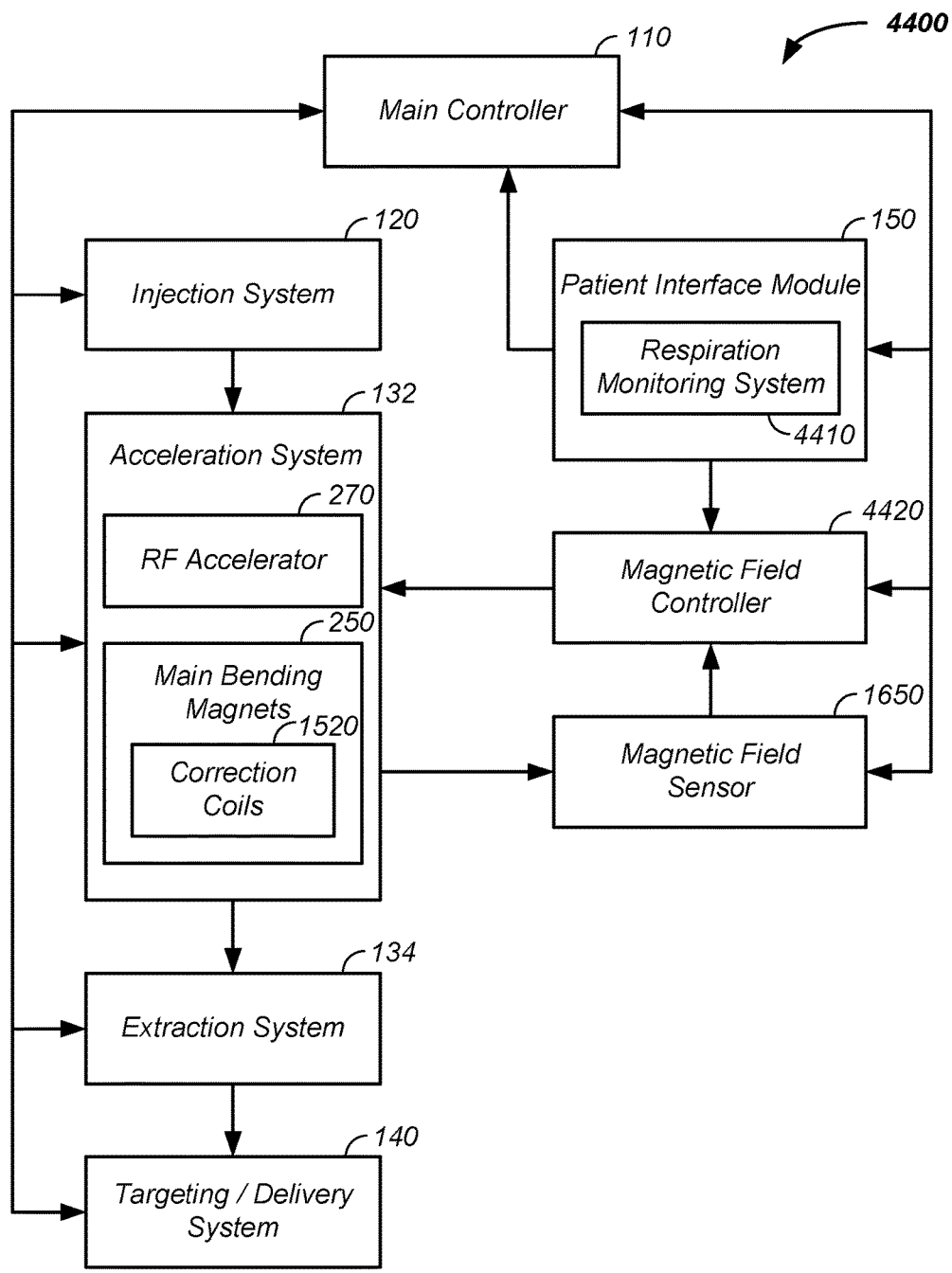
FIG. 44 shows particle field acceleration timed to a patient's respiration cycle.

Referring now to FIG. 44, the combined use of the respiration sensor and magnetic field sensor 4400 to deliver charged particles at varying energy and at varying time intervals is further described. The main controller 110 controls the injection system 120, charged particle acceleration system 132, extraction system 134, and targeting/delivery system 140. In this embodiment, the previously described respiration monitoring system 4410 of the patient interface module 150 is used as an input to a magnetic field controller 4420. A second input to the magnetic field controller 4420 is a magnetic field sensor 1650. In one case, the respiration rates from the respiration monitoring system 4410 are fed to the main controller 130, which controls the injection system 120 and/or components of the acceleration system 132 to yield a charged particle beam at a chosen period of the respiration cycle, as described supra. In a second case, the respiration data from the respiration monitoring system is used as an input to the magnetic field controller 4420. The magnetic field controller also receives feedback input from the magnetic field sensor 1650. The magnetic field controller thus times charged particle energy delivery to correlate with sensed respiration rates and delivers energy levels of the charged particle beam that are rapidly adjustable with each pulse of the accelerator using the feedback loop through the magnetic field sensor 1650.

Figure 45:
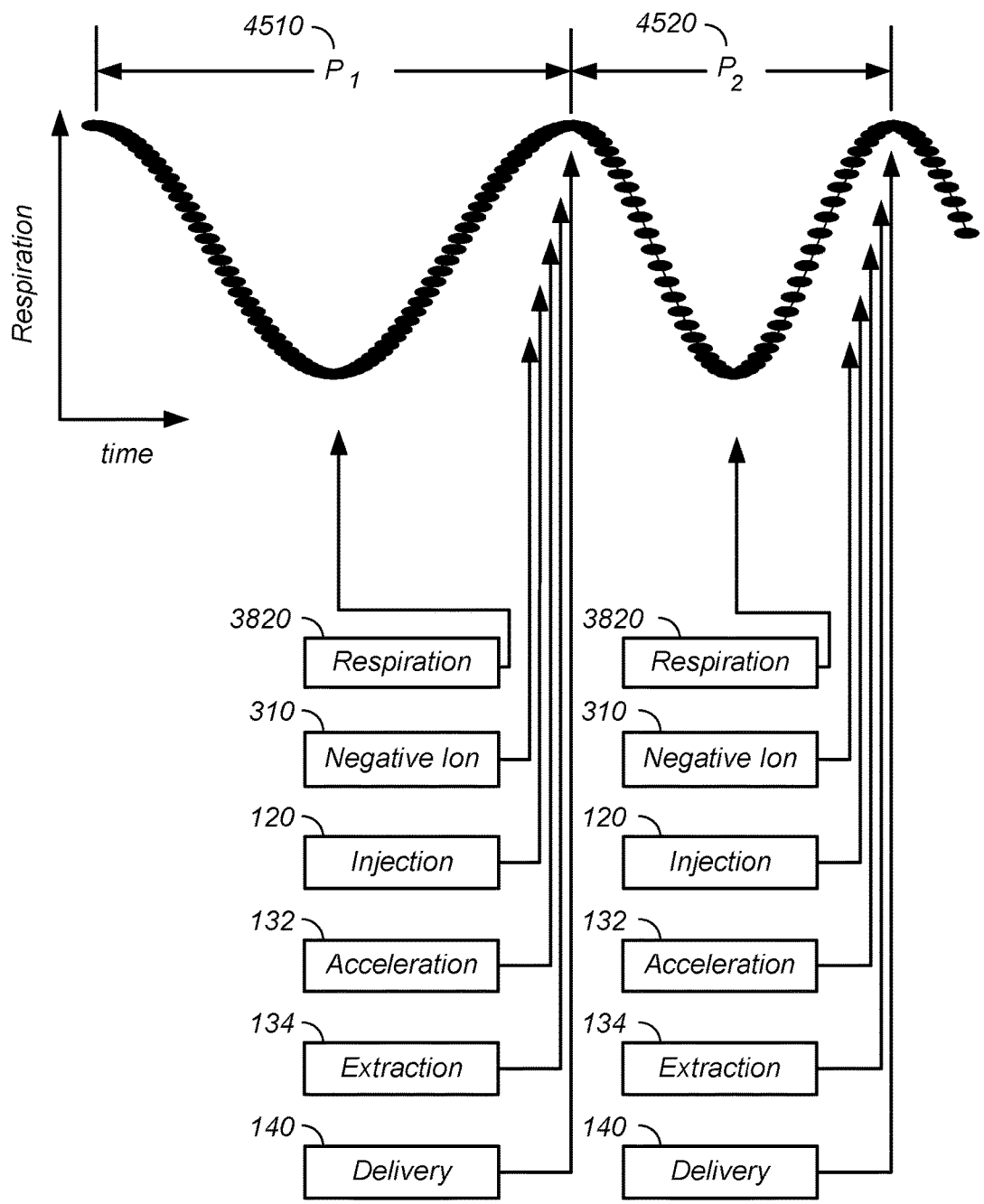
FIG. 45 illustrates adjustable particle field acceleration timing.

Referring still to FIG. 44 and now additionally referring to FIG. 45, a further example is used to clarify the magnetic field control using a feedback loop 4400 to change delivery times and/or periods of proton pulse delivery. In one case, a respiratory sensor 4410 senses the respiration cycle of the patient. The respiratory sensor sends the patient's respiration pattern or information to an algorithm in the magnetic field controller 4420, typically via the patient interface module 150 and/or via the main controller 110 or a subcomponent thereof. The algorithm predicts and/or measures when the patient is at a particular point in the respiration cycle, such as at the top or bottom of a breath. One or more magnetic field sensors 1650 are used as inputs to the magnetic field controller 4420, which controls a magnet power supply for a given magnetic, such as within a first turning magnet 1010 of a synchrotron 130. The control feedback loop is thus used to dial the synchrotron to a selected energy level and to deliver protons with the desired energy at a selected point in time, such as at a particular point in the respiration cycle. The selected point in the respiration cycle is optionally anywhere in the respiration cycle and/or for any duration during the respiration cycle. As illustrated in FIG. 45, the selected time period is at the top of a breath for a period of about 0.1, 0.5, 1 seconds. More particularly, the main controller 110 controls injection of hydrogen into the injection system, formation of the negative ion 310, controls extraction of negative ions from negative ion source 310, controls injection 120 of protons into the synchrotron 130, and/or controls acceleration of the protons in a manner that combined with extraction 134 delivers the protons 140 to the tumor at a selected point in the respiration cycle. Intensity of the proton beam is also selectable and controllable by the main controller 130 at this stage, as described supra. The feedback control from the magnetic field controller 4420 is optionally to a power or power supplies for one or both of the main bending magnet 250, described supra, or to the correction coils 1520 within the main bending magnet 250. Having smaller applied currents, the correction coils 1510, 1520 are rapidly adjustable to a newly selected acceleration frequency or corresponding charged particle energy level. Particularly, the magnetic field controller 4420 alters the applied fields to the main bending magnets or correction coils that are tied to the patient's respiration cycle. This system is in stark contrast to a system where the current is stabilized and the synchrotron delivers pulses with a fixed period. Preferably, the feedback of the magnetic field design coupled with the correction coils allows for the extraction cycle to match the varying respiratory rate of the patient, such as where a first respiration period 4510, $P_1$, does not equal a second respiration period 4520, $P_2$.

Figure 46:
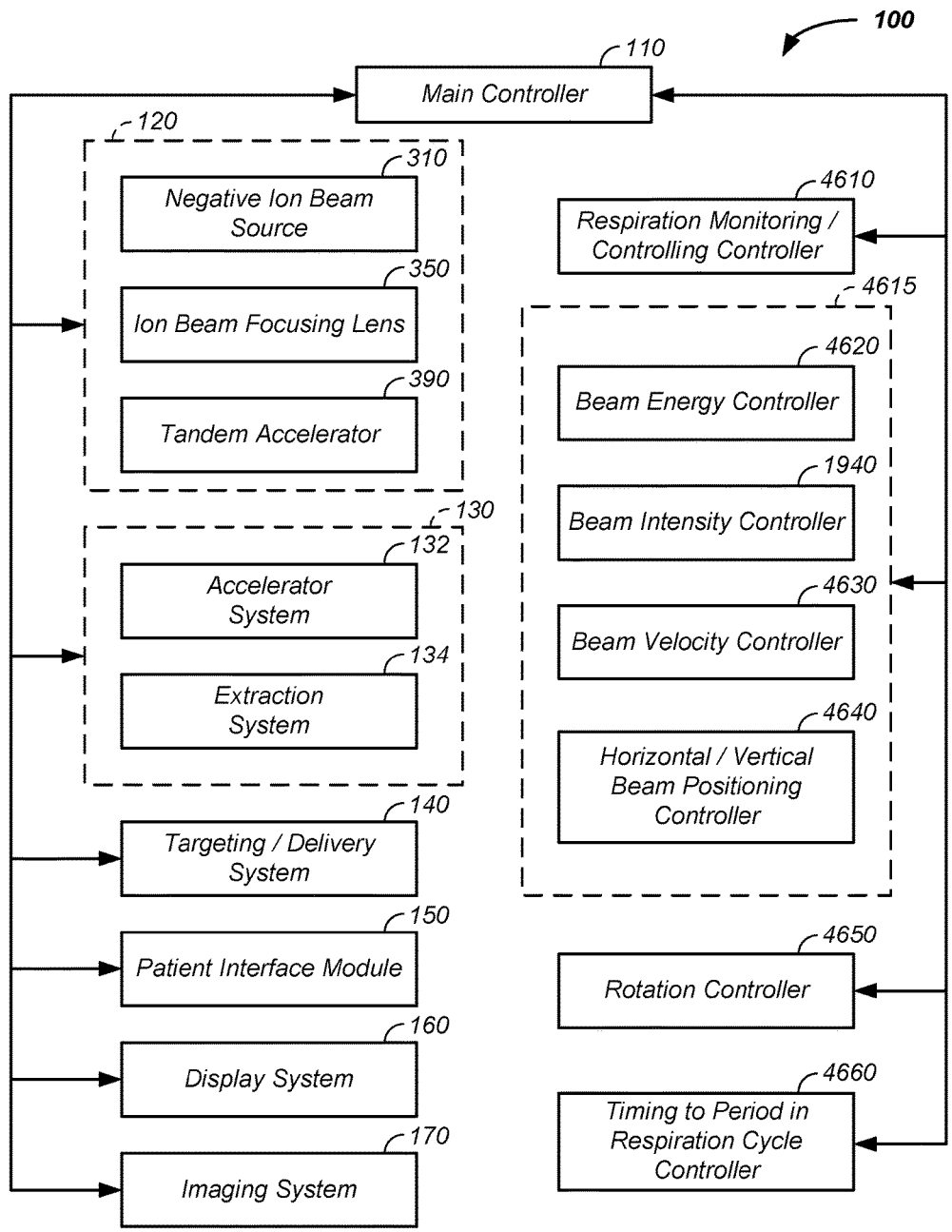
FIG. 46 illustrates charged particle cancer therapy controllers.

Referring now to FIG. 46, an example of a charged particle cancer therapy system 100 is provided. A main controller receives input from one, two, three, or four of a respiration monitoring and/or controlling controller 4610, a beam controller 4615, a rotation controller 4650, and/or a timing to a time period in a respiration cycle controller 4660. The beam controller 4615 preferably includes one or more or a beam energy controller 4620, the beam intensity controller 1940, a beam velocity controller 4630, and/or a horizontal/vertical beam positioning controller 4640. The main controller 110 controls any element of the injection system 120; the synchrotron 130; the scanning/targeting/delivery system 140; the patient interface module 150; the display system 160; and/or the imaging system 170. For example, the respiration monitoring/controlling controller 4610 controls any element or method associated with the respiration of the patient; the beam controller 4615 controls any of the elements controlling acceleration and/or extraction of the charged particle beam; the rotation controller 4650 controls any element associated with rotation of the patient 2130 or gantry; and the timing to a period in respiration cycle controller 4660 controls any aspects affecting delivery time of the charged particle beam to the patient. As a further example, the beam controller 4615 optionally controls any magnetic and/or electric field about any magnet in the charged particle cancer therapy system 100.

Computer Controlled Patient Repositioning

One or more of the patient positioning unit components and/or one of more of the patient positioning constraints are preferably under computer control. For example, the computer records or controls the position of the patient positioning elements 3315, such as via recording a series of motor positions connected to drives that move the patient positioning elements 3315. For example, the patient is initially positioned 3810 and constrained by the patient positioning constraints 3315. The position of each of the patient positioning constraints is recorded and saved by the main controller 110, by a sub-controller of the main controller 110, or by a separate computer controller. Then, imaging systems are used to locate the tumor 2120 in the patient 2130 while the patient is in the controlled position of final treatment. Preferably, when the patient is in the controlled position, multi-field imaging is performed, as described herein. The imaging system 170 includes one or more of: MRI's, X-rays, CT's, proton beam tomography, and the like. Time optionally passes at this point while images from the imaging system 170 are analyzed and a proton therapy treatment plan is devised. The patient optionally exits the constraint system during this time period, which may be minutes, hours, or days. Upon, and preferably after, return of the patient and initial patient placement into the patient positioning unit, the computer returns the patient positioning constraints to the recorded positions. This system allows for rapid repositioning of the patient to the position used during imaging and development of the multi-field charged particle irradiation treatment plan, which minimizes setup time of patient positioning and maximizes time that the charged particle beam system 100 is used for cancer treatment.

Reproducing Patient Positioning and Immobilization

In one embodiment, using a patient positioning and immobilization system 4000, a region of the patient 2130 about the tumor 2120 is reproducibly positioned and immobilized, such as with the motorized patient translation and rotation positioning system 2110 and/or with the patient positioning constraints 3315. For example, one of the above described positioning systems, such as (1) the semi-vertical partial immobilization system 3300; (2) the sitting partial immobilization system 3400; or (3) the laying position system 3500 is used in combination with the patient translation and rotation system 2110 to position the tumor 2120 of the patient 2130 relative to the proton beam path 268. Preferably, the position and immobilization system controls position of the tumor 2120 relative to the proton beam path 268, immobilizes position of the tumor 2120, and facilitates repositioning the tumor 2120 relative to the proton beam path 268 after the patient 2130 has moved away from the proton beam path 268, such as during development of the irradiation treatment plan 4345.

Preferably, the tumor 2120 of the patient 2130 is positioned in terms of 3-D location and in terms of orientation attitude. Herein, 3-D location is defined in terms of the x-, y-, and z-axes and orientation attitude is the state of pitch, yaw, and roll. Roll is rotation of a plane about the z-axis, pitch is rotation of a plane about the x-axis, and yaw is the rotation of a plane about the y-axis. Tilt is used to describe both roll and pitch. Preferably, the positioning and immobilization system controls the tumor 2120 location relative to the proton beam path 268 in terms of at least three of and preferably in terms of four, five, or six of: pitch, yaw, roll, x-axis location, y-axis location, and z-axis location.

Chair

The patient positioning and immobilization system 4000 is further described using a chair positioning example. For clarity, a case of positioning and immobilizing a tumor in a shoulder is described using chair positioning. Using the semi-vertical immobilization system 3300, the patient is generally positioned using the seat support 3320, knee support 3360, and/or foot support 3370. To further position the shoulder, a motor in the back support 3330 pushes against the torso of the patient. Additional arm support 3350 motors align the arm, such as by pushing with a first force in one direction against the elbow of the patient and the wrist of the patient is positioned using a second force in a counter direction. This restricts movement of the arm, which helps to position the shoulder. Optionally, the head support is positioned to further restrict movement of the shoulder by applying tension to the neck. Combined, the patient positioning constraints 3315 control position of the tumor 2120 of the patient 2130 in at least three dimensions and preferably control position of the tumor 2120 in terms of all of yaw, roll, and pitch movement as well as in terms of x-, y-, and z-axis position. For instance, the patient positioning constraints position the tumor 2120 and restricts movement of the tumor, such as by preventing patient slumping. Optionally, sensors in one or more of the patient positioning constraints 3315 record an applied force. In one case, the seat support senses weight and applies a force to support a fraction of the patient's weight, such as about 50, 60, 70, or 80 percent of the patient's weight. In a second case, a force applied to the neck, arm, and/or leg is recorded.

Generally, the patient positioning and immobilization system 4000 removes movement degrees of freedom from the patient 2130 to accurately and precisely position and control the position of the tumor 2120 relative to the X-ray beam path 3070, proton beam path 268, and/or an imaging beam path. Further, once the degrees of freedom are removed, the motor positions for each of the patient positioning constraints are recorded and communicated digitally to the main controller 110. Once the patient moves from the immobilization system 4000, such as when the irradiation treatment plan is generated 4350, the patient 2130 must be accurately repositioned in a patient repositioning system 4300 before the irradiation plan is implemented. To accomplish this, the patient 2130 sits generally in the positioning device, such as the chair, and the main controller sends the motor position signals and optionally the applied forces back to motors controlling each of the patient positioning constraints 3315 and each of the patient positioning constraints 3315 are automatically moved back to their respective recorded positions. Hence, re-positioning and re-immobilizing the patient 2130 is accomplished from a time of sitting to fully controlled position in less than about 10, 30, 60, 120, or 600 seconds.

Using the computer controlled and automated patient positioning system, the patient is re-positioned in the positioning and immobilization system 4300 using the recalled patient positioning constraint 3315 motor positions; the patient 2130 is translated and rotated using the patient translation and rotation system 2120 relative to the proton beam 268; and the proton beam 268 is scanned to its momentary beam position 269 by the main controller 110, which follows the generated irradiation treatment plan 4350.

Tomography

In one embodiment, the charged particle tomography apparatus is used to image a tumor in a patient.

In another embodiment, the charged particle tomography apparatus is used in combination with a charged particle cancer therapy system using common elements. For example, tomographic imaging of a cancerous tumor is performed using charged particles generated with an injector, accelerator, and guided with a delivery system that are part of the cancer therapy system, described supra.

In various embodiments, the tomography imaging system is optionally simultaneously operational with a charged particle cancer therapy system using common elements, allows tomographic imaging with rotation of the patient, is operational on a patient in an upright, semi-upright, and/or horizontal position, is simultaneously operational with X-ray imaging, and/or allows use of adaptive charged particle cancer therapy. Further, the common tomography and cancer therapy apparatus elements are optionally operational in a multi-axis and/or multi-field raster beam mode.

In conventional medical X-ray tomography, a sectional image through a body is made by moving one or both of an X-ray source and the X-ray film in opposite directions during the exposure. By modifying the direction and extent of the movement, operators can select different focal planes, which contain the structures of interest. More modern variations of tomography involve gathering projection data from multiple directions by moving the X-ray source and feeding the data into a tomographic reconstruction software algorithm processed by a computer. Herein, in stark contrast to known methods, the radiation source is a charged particle, such as a proton ion beam or a carbon ion beam. A proton beam is used herein to describe the tomography system, but the description applies to a heavier ion beam, such as a carbon ion beam. Further, in stark contrast to known techniques, herein the radiation source is preferably stationary while the patient is rotated.

Figure 47:
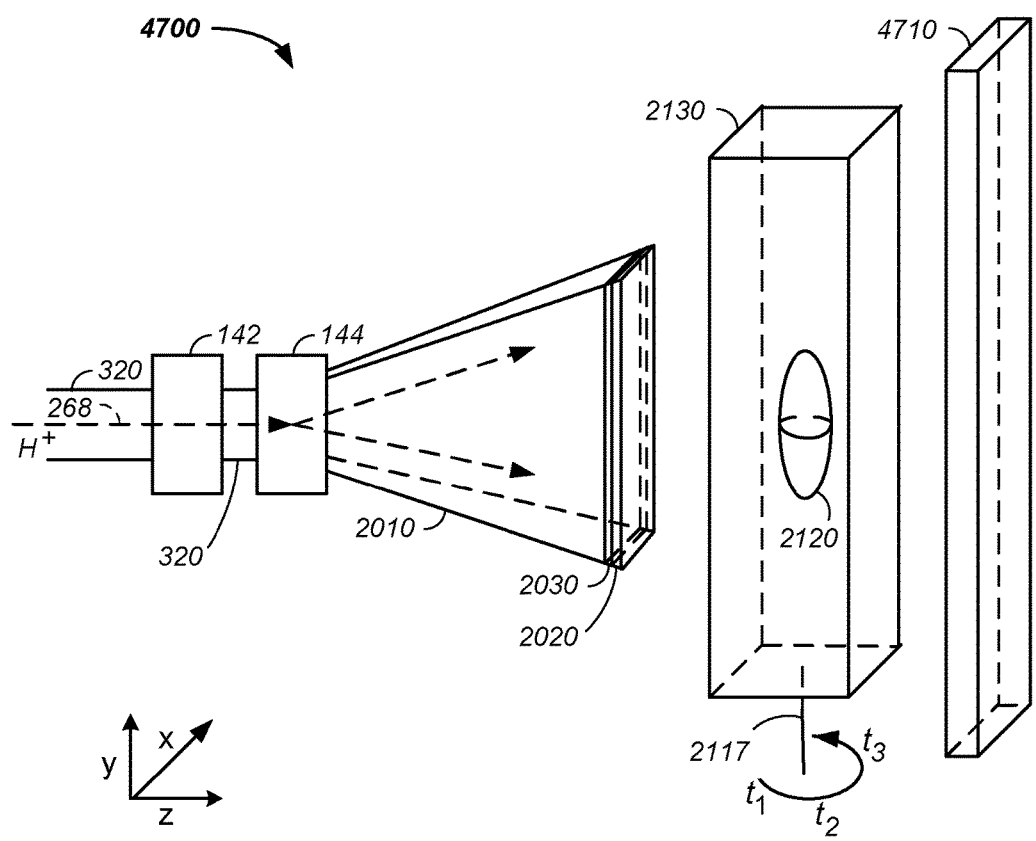
FIG. 47 illustrates a charged particle tomography system.

Referring now to FIG. 47, an example of a tomography apparatus is described. In one example, the tomography system 4700 uses elements in common with the charged particle beam system 100, including elements of one or more of the injection system 120, accelerator 130, targeting/delivery system 140, patient interface module 150, display system 160, and/or imaging system 170, such as the X-ray imaging system. Preferably, a scintillation plate 4710, such as a scintillating plastic is positioned behind the patient 2130 relative to the targeting/delivery system 140 elements. The charged particle beam system 100 as described has proven operation at up to and including 330 MeV, which is sufficient to send protons through the body and into contact with the scintillation material. The intensity or count of protons hitting the plate as a function of position is used to create an image. The patient 2130 is rotated 2117 about the y-axis and a new image is collected. Preferably, a new image is collected with about every one degree of rotation of the patient resulting in about 360 images that are combined into a tomogram using tomographic reconstruction software.

The tomographic reconstruction software uses overlapping rotationally varied images in the reconstruction. Optionally, a new image is collected at about every 2, 3, 4, 5, 10, 15, 30, or 45 degrees of rotation of the patient.

In one embodiment, a tomogram or an individual tomogram section image is collected at about the same time as cancer therapy occurs using the charged particle beam system. For example, an tomogram is collected and cancer therapy is subsequently performed: without the patient moving from the positioning systems, such as the above described semi-vertical partial immobilization system 3300, the sitting partial immobilization system 3400, or the a laying position 3500. In a second example, an individual tomogram slice is collected using a first cycle of the accelerator 130 and using a following cycle of the accelerator 130, the tumor 2120 is irradiated, such as within about 1, 2, 5, 10, 15 or 30 seconds. In a third case, about 2, 3, 4, or 5 tomogram slices are collected using 1, 2, 3, 4, or more rotation positions of the patient 2130 within about 5, 10, 15, 30, or 60 seconds of subsequent tumor irradiation therapy.

In another embodiment, the independent control of the tomographic imaging process and X-ray collection process allows simultaneous single and/or multi-field collection of X-ray images and tomographic images easing interpretation of multiple images. Indeed, the X-ray and tomographic images are optionally overlaid to from a hybrid X-ray/proton beam tomographic image as the patient is optionally in the same position for each image.

In still another embodiment, the tomogram is collected with the patient 2130 in the about the same position as when the patient's tumor is treated using subsequent irradiation therapy. For some tumors, the patient being positioned in the same upright or semi-upright position allows the tumor 2120 to be separated from surrounding organs or tissue of the patient 2130 better than in a laying position. Positioning of the scintillation plate 4710 behind the patient 2130 allows the tomographic imaging to occur while the patient is in the same upright or semi-upright position.

The use of common elements in the tomographic imaging and in the charged particle cancer therapy allows benefits of the cancer therapy, described supra, to optionally be used with the tomographic imaging, such as proton beam x-axis control, proton beam y-axis control, control of proton beam energy, control of proton beam intensity, timing control of beam delivery to the patient, rotation control of the patient, and control of patient translation all in a raster beam mode of proton energy delivery.

In yet still another embodiment, initially a three-dimensional tomographic proton based reference image is collected, such as with hundreds of individual rotation images of the tumor 2120 and patient 2130. Subsequently, just prior to proton treatment of the cancer, just a few 2-dimensional control tomographic images of the patient are collected, such as with a stationary patient or at just a few rotation positions, such as an image straight on to the patient, with the patient rotated about 45 degrees each way, and/or the patient rotated about 90 degrees each way about the y-axis. The individual control images are compared with the 3-dimensional reference image. An adaptive proton therapy is subsequently performed where: (1) the proton cancer therapy is not used for a given position based on the differences between the 3-dimensional reference image and one or more of the 2-dimensional control images and/or (2) the proton cancer therapy is modified in real time based on the differences between the 3-dimensional reference image and one or more of the 2-dimensional control images.

System Integration

Any of the systems and/or elements described herein are optionally integrated together and/or are optionally integrated with known systems.

Treatment Delivery Control System

Figure 48:
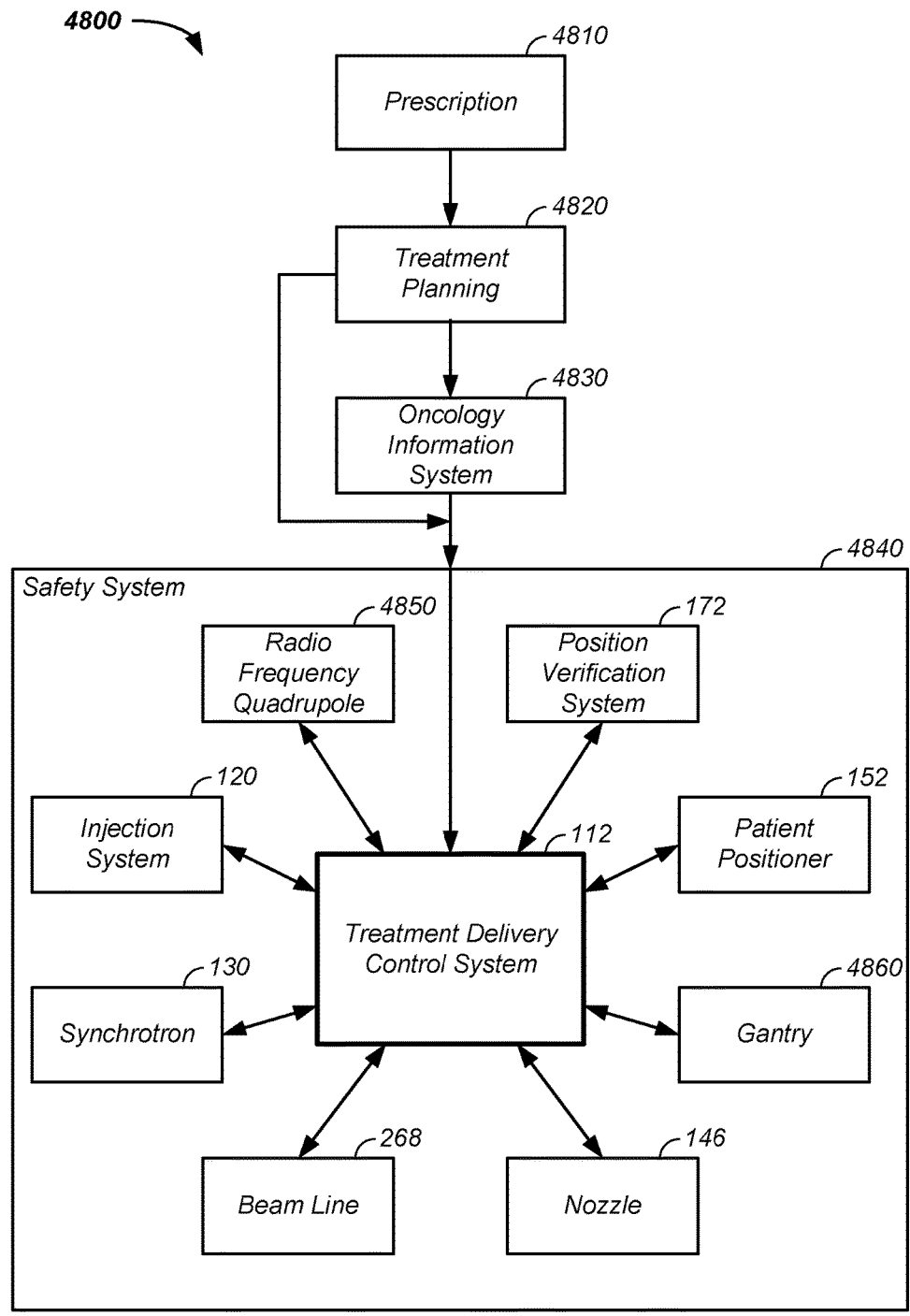
FIG. 48 illustrates a treatment delivery control system.

Referring now to FIG. 48, a centralized charged particle treatment system 4800 is illustrated. Generally, once a charged particle therapy plan is devised, a central control system or treatment delivery control system 112 is used to control sub-systems while reducing and/or eliminating direct communication between major subsystems. Generally, the treatment delivery control system 112 is used to directly control multiple subsystems of the cancer therapy system without direct communication between selected subsystems, which enhances safety, simplifies quality assurance and quality control, and facilitates programming. For example, the treatment delivery control system 112 directly controls one or more of: an imaging system, a positioning system, an injection system, a radio-frequency quadrupole system, a linear accelerator, a ring accelerator or synchrotron, an extraction system, a beam line, an irradiation nozzle, a gantry, a display system, a targeting system, and a verification system. Generally, the control system integrates subsystems and/or integrates output of one or more of the above described cancer therapy system elements with inputs of one or more of the above described cancer therapy system elements.

Still referring to FIG. 48, an example of the centralized charged particle treatment system 4800 is provided. Initially, a doctor, such as an oncologist, prescribes 4810 or recommends tumor therapy using charged particles. Subsequently, treatment planning 4820 is initiated and output of the treatment planning step 4820 is sent to an oncology information system 4830 and/or is directly sent to the treatment delivery system 112, which is an example of the main controller 110.

Still referring to FIG. 48, the treatment planning step 4820 is further described. Generally, radiation treatment planning is a process where a team of oncologist, radiation therapists, medical physicists, and/or medical dosimetrists plan appropriate charged particle treatment of a cancer in a patient. Typically, one or more imaging systems 170 are used to image the tumor and/or the patient, described infra. Planning is optionally: (1) forward planning and/or (2) inverse planning. Cancer therapy plans are optionally assessed with the aid of a dose-volume histogram, which allows the clinician to evaluate the uniformity of the dose to the tumor and surrounding healthy structures. Typically, treatment planning is almost entirely computer based using patient computed tomography data sets using multimodality image matching, image coregistration, or fusion.

Forward Planning

In forward planning, a treatment oncologist places beams into a radiotherapy treatment planning system including: how many radiation beams to use and which angles to deliver each of the beams from. This type of planning is used for relatively simple cases where the tumor has a simple shape and is not near any critical organs.

Inverse Planning

In inverse planning, a radiation oncologist defines a patient's critical organs and tumor and gives target doses and importance factors for each. Subsequently, an optimization program is run to find the treatment plan which best matches all of the input criteria.

Oncology Information System

Still referring to FIG. 48, the oncology information system 4830 is further described. Generally, the oncology information system 4830 is one or more of: (1) an oncology-specific electronic medical record, which manages clinical, financial, and administrative processes in medical, radiation, and surgical oncology departments; (2) a comprehensive information and image management system; and (3) a complete patient information management system that centralizes patient data; and (4) a treatment plan provided to the charged particle beam system 100, main controller 110, and/or the treatment delivery control system 112. Generally, the oncology information system 4830 interfaces with commercial charged particle treatment systems.

Safety System/Treatment Delivery Control System

Still referring to FIG. 48, the treatment delivery control system 112 is further described. Generally, the treatment delivery control system 112 receives treatment input, such as a charged particle cancer treatment plan from the treatment planning step 4820 and/or from the oncology information system 4830 and uses the treatment input and/or treatment plan to control one or more subsystems of the charged particle beam system 100. The treatment delivery control system 112 is an example of the main controller 110, where the treatment delivery control system receives subsystem input from a first subsystem of the charged particle beam system 100 and provides to a second subsystem of the charged particle beam system 100: (1) the received subsystem input directly, (2) a processed version of the received subsystem input, and/or (3) a command, such as used to fulfill requisites of the treatment planning step 4820 or direction of the oncology information system 4830. Generally, most or all of the communication between subsystems of the charged particle beam system 100 go to and from the treatment delivery control system 112 and not directly to another subsystem of the charged particle beam system 100. Use of a logically centralized treatment delivery control system has many benefits, including: (1) a single centralized code to maintain, debug, secure, update, and to perform checks on, such as quality assurance and quality control checks; (2) a controlled logical flow of information between subsystems; (3) an ability to replace a subsystem with only one interfacing code revision; (4) room security; (5) software access control; (6) a single centralized control for safety monitoring; and (7) that the centralized code results in an integrated safety system 4840 encompassing a majority or all of the subsystems of the charged particle beam system 100. Examples of subsystems of the charged particle cancer therapy system 100 include: a radio frequency quadrupole 4850, a radio frequency quadrupole linear accelerator, the injection system 120, the synchrotron 130, the accelerator system 132, the extraction system 134, any controllable or monitorable element of the beam line 268, the targeting/delivery system 140, the nozzle 146, a gantry 4860 or an element of the gantry 4860, the patient interface module 150, a patient positioner 152, the display system 160, the imaging system 170, a patient position verification system 172, any element described supra, and/or any subsystem element.

Still yet another embodiment includes any combination and/or permutation of any of the elements described herein.

The particular implementations shown and described are illustrative of the invention and its best mode and are not intended to otherwise limit the scope of the present invention in any way. Indeed, for the sake of brevity, conventional manufacturing, connection, preparation, and other functional aspects of the system may not be described in detail. Furthermore, the connecting lines shown in the various figures are intended to represent exemplary functional relationships and/or physical couplings between the various elements. Many alternative or additional functional relationships or physical connections may be present in a practical system.

In the foregoing description, the invention has been described with reference to specific exemplary embodiments; however, it will be appreciated that various modifications and changes may be made without departing from the scope of the present invention as set forth herein. The description and figures are to be regarded in an illustrative manner, rather than a restrictive one and all such modifications are intended to be included within the scope of the present invention. Accordingly, the scope of the invention should be determined by the generic embodiments described herein and their legal equivalents rather than by merely the specific examples described above. For example, the steps recited in any method or process embodiment may be executed in any order and are not limited to the explicit order presented in the specific examples. Additionally, the components and/or elements recited in any apparatus embodiment may be assembled or otherwise operationally configured in a variety of permutations to produce substantially the same result as the present invention and are accordingly not limited to the specific configuration recited in the specific examples.

Herein, any integral number is optionally at least the integral number or less than the integral number.

Herein, any integral number is optionally the number plus or minus 1, 2, 5, 10, or 20 percent of the integral number.

Benefits, other advantages and solutions to problems have been described above with regard to particular embodiments; however, any benefit, advantage, solution to problems or any element that may cause any particular benefit, advantage or solution to occur or to become more pronounced are not to be construed as critical, required or essential features or components.

As used herein, the terms "comprises", "comprising", or any variation thereof, are intended to reference a non-exclusive inclusion, such that a process, method, article, composition or apparatus that comprises a list of elements does not include only those elements recited, but may also include other elements not expressly listed or inherent to such process, method, article, composition or apparatus. Other combinations and/or modifications of the above-described structures, arrangements, applications, proportions, elements, materials or components used in the practice of the present invention, in addition to those not specifically recited, may be varied or otherwise particularly adapted to specific environments, manufacturing specifications, design parameters or other operating requirements without departing from the general principles of the same.

Although the invention has been described herein with reference to certain preferred embodiments, one skilled in the art will readily appreciate that other applications may be substituted for those set forth herein without departing from the spirit and scope of the present invention. Accordingly, the invention should only be limited by the Claims included below.

The invention claimed is:

1. An apparatus for treating a tumor of a patient using positively charged particles, comprising:
    a positively charged particle tomography imaging system; and
    a treatment delivery control system configured to control a plurality of sub-systems of a cancer therapy system, said plurality of sub-systems comprising:
    an accelerator system;
    an extraction system;
    a beam transport line configured to transport the positively charged particles;
    an irradiation nozzle; and
    a gantry,
    wherein a charged particle beam path sequentially passes through: at least part of an injector system, said accelerator system, said extraction system, said beam transport line, said irradiation nozzle, and at least part of said gantry,
    wherein said tomography imaging system uses all of said accelerator system, said extraction system, said beam transport line, said irradiation nozzle; and said gantry, said tomography imaging system used to generate a proton tomography image of the tumor for use in subsequent treatment of the tumor using said cancer therapy system.

2. The apparatus of claim 1, further comprising:
    an X-ray imaging system, under control of said treatment delivery control system, configured to generate an X-ray image of the tumor during use, said X-ray image overlaid with a proton beam image generated using a proton beam imaging system to form a hybrid X-ray-proton beam image.

3. The apparatus of claim 1, further comprising:
    said treatment delivery control system configured to control an imaging system, said imaging system comprising: a beam position verification layer, responsive to passage of the positively charged particles, positioned between said irradiation nozzle and the patient during use; and
    said beam position verification layer configured to indicate a location of the positively charged particles in said beam transport line between said irradiation nozzle and the patient during use.

4. The apparatus of claim 3, further comprising:
a patient positioning system configured to hold the patient in an upright position during an image collection time period of using an X-ray imaging system and using said proton beam imaging system, the patient not moving from said patient positioning system during said image collection time period.

5. The apparatus of claim 3, said treatment delivery control system further comprising:
control of multiple subsystems of said cancer therapy system without direct communication between said multiple subsystems, said multiple subsystems comprising all of: said accelerator system, said gantry, and an X-ray imaging system.

6. A method for treating a tumor of a patient using positively charged particles, comprising the steps of:
providing a positively charged particle tomography imaging system;
using a treatment delivery control system to control a plurality of sub-systems of a cancer therapy system, said plurality of sub-systems comprising:
an accelerator system;
an extraction system;
a beam transport line configured to transport the positively charged particles;
an irradiation nozzle; and
a gantry,
wherein a charged particle beam path sequentially passes through:
at least part of an injector system, said accelerator system, said extraction system, said beam transport line, said irradiation nozzle, and at least part of said gantry; and
said tomography imaging system using all of said accelerator system, said extraction system, said beam transport line, said irradiation nozzle; and said gantry to generate a proton tomography image of the tumor for use in subsequent treatment of the tumor using said cancer therapy system.

7. The method of claim 6, further comprising the steps of:
generating a three-dimensional reference image of the patient using said positively charged particle tomography imaging system using four to hundreds of rotation positions of the patient relative to the positively charged particles; and
adapting a radiation treatment plan for the tumor using a two-dimensional control image, collected while the patient is in a treatment position, through comparison of the two-dimensional control image and the three-dimensional reference image.

8. The method of claim 6, further comprising the steps of:
said treatment delivery control system controlling an imaging system; and
said imaging system determining a location of the positively charged particles in said beam transport line between said irradiation nozzle and the patient using a beam position verification layer positionally responsive to passage of the positively charged particles.

9. The method of claim 8, further comprising the step of:
said treatment delivery control system controlling multiple subsystems of said cancer therapy system without direct communication between said multiple subsystems, said multiple subsystems comprising all of: said accelerator system and an X-ray imaging system.

10. The method of claim 6, further comprising the step of:
replacing a specific subsystem of said plurality of subsystems controlled by said treatment delivery control system while only revising code to said specific subsystem.

* * * * *